(12) United States Patent
Zhang et al.

(10) Patent No.: US 10,036,059 B2
(45) Date of Patent: *Jul. 31, 2018

(54) COMPOSITIONS OF TOEHOLD PRIMER DUPLEXES AND METHODS OF USE

(71) Applicant: President and Fellows of Harvard College, Cambridge, MA (US)

(72) Inventors: David Yu Zhang, Houston, TX (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 706 days.

This patent is subject to a terminal disclaimer.

(21) Appl. No.: 14/553,165

(22) Filed: Nov. 25, 2014

(65) Prior Publication Data

US 2015/0152491 A1   Jun. 4, 2015

Related U.S. Application Data

(62) Division of application No. 13/882,231, filed as application No. PCT/US2011/058178 on Oct. 27, 2011, now Pat. No. 9,284,602.

(60) Provisional application No. 61/407,291, filed on Oct. 27, 2010.

(51) Int. Cl.
| | |
|---|---|
| C12Q 1/68 | (2018.01) |
| C07H 21/02 | (2006.01) |
| C12Q 1/6853 | (2018.01) |
| C12Q 1/6832 | (2018.01) |
| C12Q 1/6848 | (2018.01) |
| C12Q 1/686 | (2018.01) |

(52) U.S. Cl.
CPC ........... *C12Q 1/6853* (2013.01); *C07H 21/02* (2013.01); *C12Q 1/686* (2013.01); *C12Q 1/6832* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 6,033,851 | A | 3/2000 | Akio |
| 7,745,594 | B2 | 6/2010 | Seelig et al. |
| 7,799,522 | B2 | 9/2010 | Li et al. |
| 8,110,353 | B2 | 2/2012 | Zhang et al. |
| 8,815,507 | B2 | 8/2014 | Zhang |
| 9,284,602 | B2 | 3/2016 | Zhang et al. |
| 9,796,748 | B2 | 10/2017 | Schaus et al. |
| 2002/0127575 | A1 | 9/2002 | Hoke et al. |
| 2003/0165859 | A1 | 9/2003 | Nazarenko et al. |
| 2007/0072215 | A1 | 3/2007 | Seelig et al. |
| 2009/0011956 | A1 | 1/2009 | Yin et al. |
| 2009/0087838 | A1 | 4/2009 | Reif et al. |
| 2009/0191546 | A1 | 7/2009 | Reif et al. |
| 2009/0258353 | A1* | 10/2009 | Yoon ............... C12Q 1/686 435/6.11 |
| 2010/0047926 | A1 | 2/2010 | Dirks et al. |
| 2013/0224859 | A1 | 8/2013 | Bachelet et al. |
| 2013/0261019 | A1 | 10/2013 | Lin et al. |
| 2013/0274135 | A1 | 10/2013 | Zhang et al. |
| 2014/0066610 | A1 | 3/2014 | Schaus et al. |
| 2014/0213778 | A1 | 7/2014 | Yin et al. |
| 2014/0220655 | A1 | 8/2014 | Sun et al. |
| 2014/0303320 | A1 | 10/2014 | Schaus et al. |
| 2016/0153036 | A1 | 6/2016 | Chen et al. |

FOREIGN PATENT DOCUMENTS

| | | |
|---|---|---|
| EP | 0 851 033 A1 | 7/1998 |
| WO | WO 2007/047572 A2 | 4/2007 |
| WO | WO 2008/097929 A1 | 8/2008 |
| WO | WO 2009/019008 A1 | 2/2009 |
| WO | WO 2010/048002 A1 | 4/2010 |
| WO | WO 2010/065626 A1 | 6/2010 |
| WO | WO 2011/112534 A1 | 9/2011 |
| WO | WO 2012/058488 A1 | 5/2012 |
| WO | WO 2014/018675 A1 | 1/2014 |
| WO | WO 2014/074597 A1 | 5/2014 |
| WO | WO 2014/074648 A2 | 5/2014 |
| WO | WO 2014/078636 A1 | 5/2014 |

OTHER PUBLICATIONS

Li, Qingge, Guoyan Luan, Qiuping Guo, and Jixuan Liang. A new class of homogeneous nucleic acid probes based on specific displacement hybridization. Nucleic Acids Research 2002. 30(2): e5: pp. 1-9.*

Amicarelli et al., FLAG assay as a novel method for real-time signal generation during PCR: application to detection and genotyping of KRAS codon 12 mutations. Nucleic Acids Res. 2007;35(19):e131. Epub Oct. 11, 2007.

Andersen et al., Self-assembly of a nanoscale DNA box with a controllable lid. Nature. May 7, 2009;459(7243):73-6. doi: 10.1038/nature07971.

Ashford, Precision Nanoscale Car Parts Self-Assembled From DNA. Popular Science. Aug. 6, 2009. Available at http://www.popsci.com/scitech/article/2009-08/nano-origami-goes-3d-and-curvy. 3 pages.

Breslauer et al., Predicting DNA duplex stability from the base sequence. Proc Natl Acad Sci U S A. Jun. 1986;83(11):3746-50.

Cha et al., Mismatch amplification mutation assay (MAMA): application to the c-H-ras gene. PCR Methods Appl. Aug. 1992;2(1):14-20.

Cho et al., Applications of aptamers as sensors. Annu Rev Anal Chem (Palo Alto Calif). 2009;2:241-64. doi:10.1146/annurev.anchem.1.031207.112851.

Dirks et al., Thermodynamic Analysis of Interacting Nucleic Acid Strands. SIAM Rev. 2007;49(1):65-88.

(Continued)

*Primary Examiner* — Samuel C Woolwine
*Assistant Examiner* — Olayinka A Oyeyemi
(74) *Attorney, Agent, or Firm* — Wolf, Greenfield & Sacks, P.C.

(57) ABSTRACT

Provided herein are primers and primer systems having improved specificity and kinetics over existing primers, and methods of use thereof.

21 Claims, 25 Drawing Sheets

(56) References Cited

OTHER PUBLICATIONS

Dirks et al., Triggered amplification by hybridization chain reaction. PNAS. 2004;101: 15275-78.

Dobosy et al., RNase H-dependent PCR (rhPCR): improved specificity and single nucleotide polymorphism detection using blocked cleavable primers. BMC Biotechnol. Aug. 10, 2011;11:80. doi:10.1186/1472-6750-11-80.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Douglas et al., Self-assembly of DNA into nanoscale three-dimensional shapes. Nature. May 21, 2009;459(7245):414-8. Available in PMC Nov. 21, 2009.

Genot et al., Remote Toehold: A Mechanism for Flexible Control of DNA Hybridization Kinetics. J. Am. Chem. Soc. 2011:133(7):2177-82.

Gevensleben et al., Noninvasive detection of HER2 amplification with plasma DNA digital PCR. Clin Cancer Res. Jun. 15, 2013;19(12):3276-84. doi:10.1158/1078-0432.CCR-12-3768. Epub May 1, 2013.

Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.

Hall et al., Kinetic optimization of a protein-responsive aptamer beacon. Biotechnol Bioeng. Aug. 15, 2009;103(6):1049-59.

Han et al., Self-assembly with DNA origami. NSF NSE Grantees Conference presentation. Arlington, VA. Dec. 5-7, 2011.

Hotz, Gene Expression: Origami at the Molecular Level. The Wall Street Journal. Jun. 5, 2009. Available at http://www.wsj.com/articles/SB124413997181485425. 6 pages.

Kaboev et al., PCR hot start using primers with the structure of molecular beacons (hairpin-like structure). Nucleic Acids Res. Nov. 1, 2000;28(21):E94.

Krueger et al., Redesigning the architecture of the base pair: toward biochemical and biological function of new genetic sets. Chem Biol. Mar. 27, 2009;16(3):242-8.

Lang et al., Optimized allele-specific real-time PCR assays for the detection of common mutations in KRAS and BRAF. J Mol Diagn. Jan. 2011;13(1):23-8. doi:10.1016/j.jmoldx.2010.11.007. Epub Dec. 23, 2010.

Lebedev et al., Hot start PCR with heat-activatable primers: a novel approach for improved PCR performance. Nucleic Acids Res. Nov. 2008;36(20):e131. Epub Sep. 16, 2008.

Li et al., Genotyping with TaqMAMA. Genomics. Feb. 2004;83(2):311-20.

Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.

Liu et al., Pyrophosphorolysis-activated polymerization (PAP):application to allele-specific amplification. Biotechniques. Nov. 2000;29(5):1072-6, 1078, 1080 passim.

Lizardi et al., Mutation detection and single-molecule counting using isothermal rolling-circle amplification. Nat Genet. Jul. 1998;19(3):225-32.

Mann et al., A thermodynamic approach to PCR primer design. Nucleic Acids Res. Jul. 2009;37(13):e95. Epub Jun. 15, 2009.

McKeen et al., Synthesis of fluorophore and quencher monomers for use in scorpion primers and nucleic acid structural probes. Org Biomol Chem. Jul. 7, 2003;1(13):2267-75.

Milbury et al., Multiplex amplification coupled with COLD-PCR and high resolution melting enables identification of low-abundance mutations in cancer samples with low DNA content. J Mol Diagn. Mar. 2011;13(2):220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Morandi et al., Allele specific locked nucleic acid quantitative PCR (ASLNAqPCR):an accurate and cost-effective assay to diagnose and quantify KRAS and BRAF mutation. PLoS One. 2012;7(4):e36084. doi: 10.1371/journal.pone.0036084. Epub Apr. 30, 2012.

Morlan et al., Mutation detection by real-time PCR: a simple, robust and highly selective method. PLoS One. 2009;4(2):e4584. doi:10.1371/journal.pone.0004584. Epub Feb. 25, 2009.

Newton et al., Analysis of any point mutation in DNA. The amplification refractory mutation system (ARMS). Nucleic Acids Res. Apr. 11, 1989;17(7):2503-16.

Orum et al., Single base pair mutation analysis by PNA directed PCR clamping. Nucleic Acids Res. Nov. 25, 1993;21(23):5332-6.

Petersen et al., LNA: a versatile tool for therapeutics and genomics. Trends Biotechnol. Feb. 2003;21(2):74-81.

Pinzani et al., BRAFV600E detection in melanoma is highly improved by COLD-PCR. Clin Chim Acta. May 12, 2011;412(11-12):901-5. doi:10.1016/j.cca.2011.01.014. Epub Jan. 22, 2011.

Reif et al., Complexity of Graph Self-assembly in Accretive Systems and Self-destructible Systems. Lecture Notes on Computer Science. 2006;3892:257-74.

Rothemund, Folding DNA to create nanoscale shapes and patterns. Nature. Mar. 16, 2006;440:297-302.

Saiki et al., Primer-directed enzymatic amplification of DNA with a thermostable DNA polymerase. Science. Jan. 29, 1988;239(4839):487-91.

Santalucia Jr et al., The thermodynamics of DNA structural motifs. Annu Rev Biophys Biomol Struct. 2004;33:415-40.

Seeman, An overview of structural DNA nanotechnology. Mol Biotechnol. Nov. 2007;37(3):246-57. Epub Jul. 12, 2007.

Seyama et al., A novel blocker-PCR method for detection of rare mutant alleles in the presence of an excess amount of normal DNA. Nucleic Acids Res. May 25, 1992;20(10):2493-6.

Shih et al., Knitting complex weaves with DNA origami. Current Opinion in Structural Biology. Jun. 2010;20(3):276-82. Author manuscript available in PMC Jun. 1, 2011.

Tulpan et al., Free energy estimation of short DNA duplex hybridizations. BMC Bioinformatics. Feb. 24, 2010;11:105. doi:10.1186/1471-2105-11-105.

Tyagi et al., Molecular beacons: probes that fluoresce upon hybridization. Nat Biotechnol. Mar. 1996;14(3):303-8.

Winfree et al., Design and self-assembly of two-dimensional DNA crystals. Nature. Aug. 6, 1998;394(6693):539-44.

Yin et al., Programming biomolecular self-assembly pathways. Nature. Jan. 17, 2008;451(7176):318-22. doi: 10.1038/nature06451.

Yin et al., Programming DNA tube circumferences. Science. Aug. 8, 2008;321(5890):824-6.

Zadeh et al., NUPACK: Analysis and design of nucleic acid systems. J Comput Chem. Jan. 15, 2011;32(1):170-3. doi:10.1002/jcc.21596.

Zhang et al., A DNA-Origami chip platform for label-free SNP genotyping using toehold-mediated strand displacement. Small. Sep. 6, 2010;6(17):1854-8.

Zhang et al., Integrating DNA strand-displacement circuitry with DNA tile self-assembly. Nat Commun. 2013;4:1965.

Zhang et al., Control of DNA strand displacement kinetics using toehold exchange. J Am Chem Soc. Dec. 2, 2009;131(47):17303-14.

Zhang et al., Dynamic DNA nanotechnology using strand-displacement reactions. Nat Chem. Feb. 2011;3(2):103-13. doi: 10.1038/nchem.957.

Zhang et al., Optimizing the specificity of nucleic acid hybridization. Nat Chem. Jan. 22, 2012;4(3):208-14. doi: 10.1038/nchem.1246.

Zhang, Cooperative Hybridization of Oligonucleotides. J. Am. Chem. Soc. 2011;133 (4):1077-86.

Zhang, Dynamic DNA Strand Displacement Circuits. Doctoral Thesis, California Institute of Technology. May 2010.

Zhou et al., Enrichment and detection of rare alleles by means of snapback primers and rapid-cycle PCR. Clin Chem. May 2010;56(5):814-22. doi: 10.1373/clinchem.2009.142034. Epub Mar. 18, 2010.

(56) References Cited

OTHER PUBLICATIONS

Zhou et al., Rare allele enrichment and detection by allele-specific PCR, competitive probe blocking, and melting analysis. BioTechniques. May 2011;50(5):311-8.

* cited by examiner

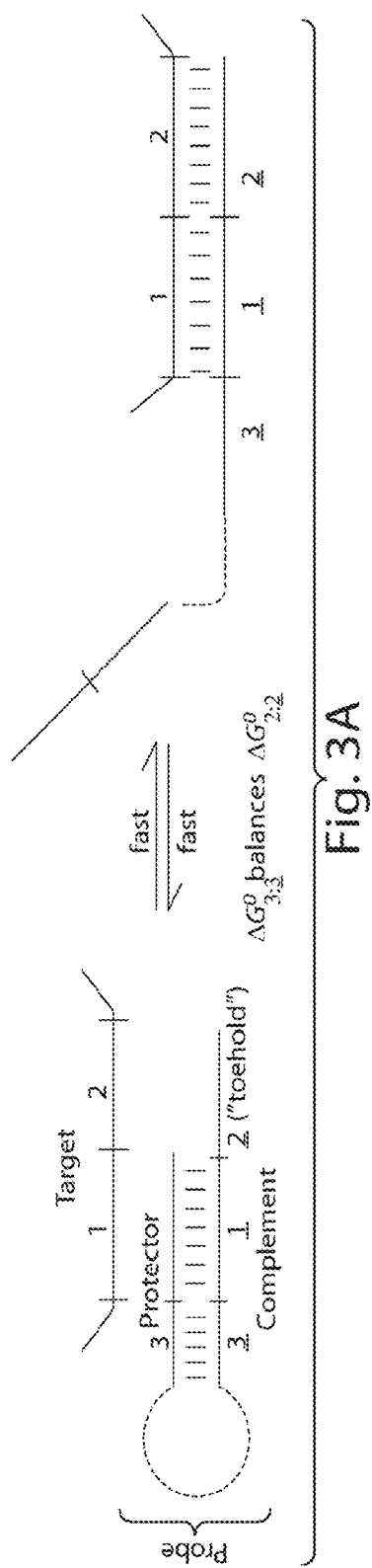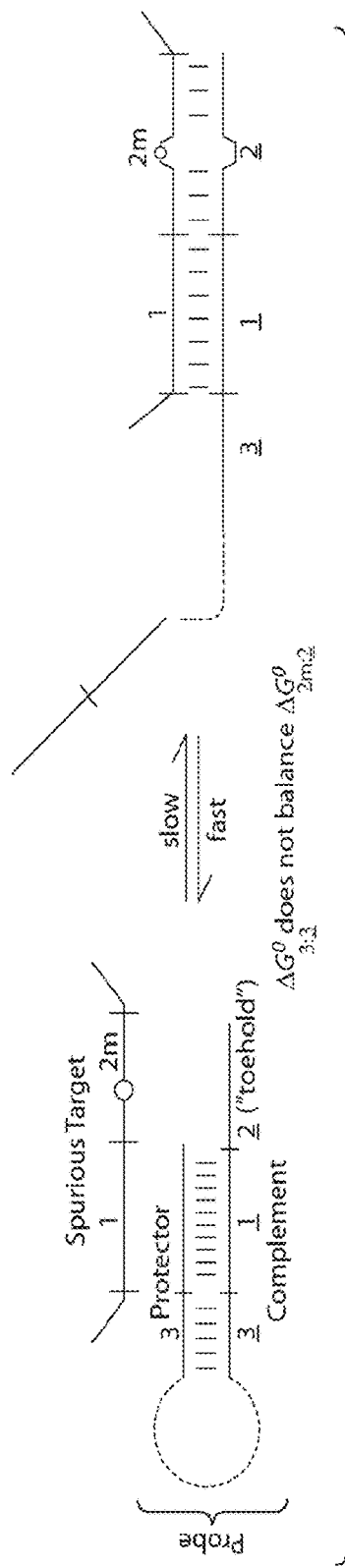

SEQUENCE LISTING

<160> NUMBER OF SEQ ID NOS: 149

<210> SEQ ID NO 1
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 1
attcagacat tcaataccct acgtctcca                               29

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
tcgtcaccat tcaataccct ac                                      22

<210> SEQ ID NO 3
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 3
agcagtggta agttatggga tgcagaggt                               29

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
cattcaatac cctactagat gt                                      22

<210> SEQ ID NO 5
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 5
taagtcggta agttatggga tgatctaca                               29

<210> SEQ ID NO 6
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 6
tggagacgta gggtattgaa tgaggttttt tcctcattca atacccctac         49

<210> SEQ ID NO 7
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 7
cattcaatac cctactagtt ttttctagta gggtattgaa tgtctgaat          49

<210> SEQ ID NO 8

<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 8
ttacattcaa taccctacgt ctccatga                                      28

<210> SEQ ID NO 9
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 9
cgtctccaac cttttttggt tggagacgta gggtattgaa tgaggttttt tcctcattca    60
a                                                                   61

<210> SEQ ID NO 10
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 10
cgtctccaac c                                                        11

<210> SEQ ID NO 11
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 11
ggttggagac gtagggtatt gaatgaggtt ttttcctcat tcaa                    44

<210> SEQ ID NO 12
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 12
cctcattcaa                                                          10

<210> SEQ ID NO 13
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 13
cgtctccaac cttttttggt tggaagacgt agggtattga atgagg                  46

<210> SEQ ID NO 14
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 14
ggagtaagtt atgggatgca gaggttgg                                    28

<210> SEQ ID NO 15
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 15
cgtctccatt tttttggaga cgtagggtat tgaatgtttt ttcattcaa              49

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
cattcaatac cctacgtctc ca                                          22

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
cattcaatac cctacgtatc ca                                          22

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
tcgacaccat tcaataccct ac                                          22

<210> SEQ ID NO 19
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 19
agctgtggta agttatggga tgcagaggt                                   29

<210> SEQ ID NO 20
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 20
gatcgacact cattcaatac cctacgtctc acgatc                           36

<210> SEQ ID NO 21

<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 21
ttgcatccac tcattcaata cc                                            22

<210> SEQ ID NO 22
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 22
aacgtaggtg agtaagttat gggatgcag                                     29

<210> SEQ ID NO 23
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 23
aacgtaggtg agtaagttat gggatgcaga gtgct                              35

<210> SEQ ID NO 24
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 24
gatcgacact cattcattac cctacgtcaa acttga                             36

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
cactcattca ataccctacg tc                                            22

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
tgaggtagta gtttgtacag tt                                            22

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
ttaatgctaa tcgtgatagg gt                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 28
cacttgatac aagcttacca tc                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 29
caagaacaga tgtaccatca ca                                              22

<210> SEQ ID NO 30
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 30
ugagguagua guuugacagu u                                               21

<210> SEQ ID NO 31
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 31
uuuaugauug agguaguagu uug                                             23

<210> SEQ ID NO 32
<211> LENGTH: 27
<212> TYPE: RNA
<213> ORGANISM: Artificial Sequence
<220> FEATURE:
<223> OTHER INFORMATION: Synthetic Oligonucleotide

<400> SEQUENCE: 32
uacuaacucc aucaucaaac augucaa                                         27

<210> SEQ ID NO 33
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 33
tgcatccact cattcaatac c                                               21

<210> SEQ ID NO 34
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 34
gcatccactc attcaatacc                                                   20

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 35
catccactca ttcaatacc                                                    19

<210> SEQ ID NO 36
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 36
cactcattca atacc                                                        15

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
atgattgagg tagtagtttg                                                   20

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 38
tgattgaggt agtagtttg                                                    19

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
aggatttaat gctaatcgtg                                                   20

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 40
ggatttaatg ctaatcgtg                                                    19
```

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
ctcatcactt gatacaagct                                           20

<210> SEQ ID NO 42
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 42
tcatcacttg atacaagct                                            19

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
cgttccaaga acagatgtac                                           20

<210> SEQ ID NO 44
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 44
gttccaagaa cagatgtac                                            19

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 45
gactcattca ataccctacg tc                                        22

<210> SEQ ID NO 46
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 46
cactctttca ataccctacg tc                                        22

<210> SEQ ID NO 47
<211> LENGTH: 22
<212> TYPE: DNA
<213> ORGANISM: Artificial Sequence
<220> FEATURE:

<223> OTHER INFORMATION: Synthetic Oligonucleotide

<400> SEQUENCE: 47
cactcattca ttaccctacg tc                                    22

<210> SEQ ID NO 48
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 48
cactcattca ctaccctacg tc                                    22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
cactcattca gtaccctacg tc                                    22

<210> SEQ ID NO 50
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 50
cactcattca taccctacgt c                                     21

<210> SEQ ID NO 51
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 51
cactcattca aataccctac gtc                                   23

<210> SEQ ID NO 52
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 52
cactcattca tataccctac gtc                                   23

<210> SEQ ID NO 53
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 53
cactcattca cataccctac gtc                                   23

```
<210> SEQ ID NO 54
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 54
cactcattca gataccctac gtc                                              23

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 55
cactcattca ataccgtacg tc                                               22

<210> SEQ ID NO 56
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 56
tcaggtagta gtttgtacag tt                                               22

<210> SEQ ID NO 57
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 57
tgaggttgta gtttgtacag tt                                               22

<210> SEQ ID NO 58
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 58
tgaggtagta gattgtacag tt                                               22

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 59
tgaggtagta gtttgttcag tt                                               22

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligonucleotide
```

<400> SEQUENCE: 60
tgaggtagta gtttgtccag tt                                          22

<210> SEQ ID NO 61
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 61
tgaggtagta gtttgtgcag tt                                          22

<210> SEQ ID NO 62
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 62
tgaggtagta gtttgtcagt t                                           21

<210> SEQ ID NO 63
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 63
tgaggtagta gtttgtaaca gtt                                         23

<210> SEQ ID NO 64
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 64
tgaggtagta gtttgttaca gtt                                         23

<210> SEQ ID NO 65
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 65
tgaggtagta gtttgtgaca gtt                                         23

<210> SEQ ID NO 66
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 66
tgaggtagta gtttgtcaca gtt                                         23

<210> SEQ ID NO 67
<211> LENGTH: 22

```
<212> TYPE: DNA
<213> ORGANISM: Artificial Sequence
<220> FEATURE:
<223> OTHER INFORMATION: Synthetic Oligonucleotide

<400> SEQUENCE: 67
tttatgctaa tcgtgatagg gt                                              22

<210> SEQ ID NO 68
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 68
ttaatgcaaa tcgtgatagg gt                                              22

<210> SEQ ID NO 69
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 69
ttaatgcgaa tcgtgatagg gt                                              22

<210> SEQ ID NO 70
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 70
ttaatgccaa tcgtgatagg gt                                              22

<210> SEQ ID NO 71
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 71
ttaatgcaat cgtgataggg t                                               21

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 72
ttaatgcata atcgtgatag ggt                                             23

<210> SEQ ID NO 73
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 73
```
ttaatgctta atcgtgatag ggt                23

<210> SEQ ID NO 74
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 74
ttaatgcgta atcgtgatag ggt                23

<210> SEQ ID NO 75
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 75
ttaatgccta atcgtgatag ggt                23

<210> SEQ ID NO 76
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 76
ttaatgctaa tcctgatagg gt                 22

<210> SEQ ID NO 77
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 77
ttaatgctaa tcgtgattgg gt                 22

<210> SEQ ID NO 78
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 78
cacatgatac aagcttacca tc                 22

<210> SEQ ID NO 79
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 79
cacttgattc aagcttacca tc                 22

<210> SEQ ID NO 80
<211> LENGTH: 22
<212> TYPE: DNA
<213> ORGANISM: Artificial Sequence

```
<220> FEATURE:
<223> OTHER INFORMATION: Synthetic Oligonucleotide

<400> SEQUENCE: 80
cacttgatac aaggttacca tc                                          22

<210> SEQ ID NO 81
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 81
cacttgatac aagcttacga tc                                          22

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 82
cacttgatac aagcttacaa tc                                          22

<210> SEQ ID NO 83
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 83
cacttgatac aagcttacta tc                                          22

<210> SEQ ID NO 84
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 84
cacttgatac aagcttacat c                                           21

<210> SEQ ID NO 85
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 85
cacttgatac aagcttaccc atc                                         23

<210> SEQ ID NO 86
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 86
cacttgatac aagcttacgc atc                                         23
```

```
<210> SEQ ID NO 87
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 87
cacttgatac aagcttacac atc                                            23

<210> SEQ ID NO 88
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 88
cacttgatac aagcttactc atc                                            23

<210> SEQ ID NO 89
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 89
catgaacaga tgtaccatca ca                                             22

<210> SEQ ID NO 90
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 90
caagaactga tgtaccatca ca                                             22

<210> SEQ ID NO 91
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 91
caagaacaga tgaaccatca ca                                             22

<210> SEQ ID NO 92
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 92
caagaacaga tgcaccatca ca                                             22

<210> SEQ ID NO 93
<211> LENGTH: 22
<212> TYPE: DNA
<213> ORGANISM: Artificial Sequence
<220> FEATURE:
<223> OTHER INFORMATION: Synthetic Oligonucleotide
```

<400> SEQUENCE: 93
caagaacaga tggaccatca ca                                        22

<210> SEQ ID NO 94
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 94
caagaacaga tgaccatcac a                                         21

<210> SEQ ID NO 95
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 95
caagaacaga tgataccatc aca                                       23

<210> SEQ ID NO 96
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 96
caagaacaga tgttaccatc aca                                       23

<210> SEQ ID NO 97
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 97
caagaacaga tgctaccatc aca                                       23

<210> SEQ ID NO 98
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 98
caagaacaga tggtaccatc aca                                       23

<210> SEQ ID NO 99
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 99
caagaacaga tgtaccaaca ca                                        22

<210> SEQ ID NO 100

```
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 100
cactcattca atacectacg tctttt                                          26

<210> SEQ ID NO 101
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 101
cactcattca atacectacg tc                                              22

<210> SEQ ID NO 102
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 102
tttatgattg aggtagtagt ttg                                             23

<210> SEQ ID NO 103
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 103
tactaactcc atcatcaaac atgtcaa                                         27

<210> SEQ ID NO 104
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 104
tttaggattt aatgctaatc gtg                                             23

<210> SEQ ID NO 105
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 105
tcctaaatta cgattagcac tatccca                                         27

<210> SEQ ID NO 106
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 106
```
tttcgtccca agaacagatg tac                                        23

<210> SEQ ID NO 107
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 107
gcagggttct tgtctacatg gtagtgt                                    27

<210> SEQ ID NO 108
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 108
ttttgcatcc actcattcaa tacc                                       24

<210> SEQ ID NO 109
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 109
acgtaggtga gtaagttatg ggatgcag                                   28

<210> SEQ ID NO 110
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 110
tttgcatcca ctcattcaat acc                                        23

<210> SEQ ID NO 111
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 111
cgtaggtgag taagttatgg gatgcag                                    27

<210> SEQ ID NO 112
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 112
ggacgttgat atgggacgta gggtattgaa tgagtg                          36

<210> SEQ ID NO 113
<211> LENGTH: 61
<212> TYPE: DNA

<213> ORGANISM: Artificial Sequence
<220> FEATURE:
<223> OTHER INFORMATION: Synthetic Oligonucleotide

<400> SEQUENCE: 113
gcttaagcct tcactattca atgtatgaga ataaaccctc ctctgttaga ggctaagtac    60
t    61

<210> SEQ ID NO 114
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 114
cgtcgctcgg tttgcttctg catggagggt gaggactttt atacacaggg aagcgagctc    60

<210> SEQ ID NO 115
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 115
tgaggtagta gtttgtacag ttgagaagtt aggttg    36

<210> SEQ ID NO 116
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 116
caacctaact tctcaactgt acaaactact acctca    36

<210> SEQ ID NO 117
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 117
gagctcgctt ccctgtgtat aaaagtcctc accctccatg cagaagcaaa ccgagcgacg    60

<210> SEQ ID NO 118
<211> LENGTH: 61
<212> TYPE: DNA
<213> ORGANISM: Artificial Sequence
<220> FEATURE:
<223> OTHER INFORMATION: Synthetic Oligonucleotide

<400> SEQUENCE: 118
agtacttagc ctctaacaga ggagggttta ttctcataca ttgaatagtg aaggcttaag    60
c    61

<210> SEQ ID NO 119
<211> LENGTH: 36
<212> TYPE: DNA
<213> ORGANISM: Artificial Sequence
<220> FEATURE:
<223> OTHER INFORMATION: Synthetic Oligonucleotide

```
<400> SEQUENCE: 119
cactcattca ataccctacg tcccatatca acgtcc                                36

<210> SEQ ID NO 120
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 120
ggacgttgat atgggacgtc gggtattgaa tgagtg                                36

<210> SEQ ID NO 121
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 121
tgacctaatg ctaactcgtg tcgctctgcg gcttc                                 35

<210> SEQ ID NO 122
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 122
tctacttgac gtatacggtc tagctgccac ggagg                                 35

<210> SEQ ID NO 123
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 123
tgtggtagta gtttgtacag ttgagaagtt aggttg                                36

<210> SEQ ID NO 124
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 124
caacctaact tctcaactgt acaaactact accaca                                36

<210> SEQ ID NO 125
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 125
cctccgtggc agctagaccg tatacgtcaa gtaga                                 35

<210> SEQ ID NO 126
```

```
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 126
gaagccgcag agcgacacga gttagcatta ggtca                               35

<210> SEQ ID NO 127
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 127
cactcattca atacccgacg tcccatatca acgtcc                              36

<210> SEQ ID NO 128
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 128
gacgtagggt attgaatgag tg                                             22

<210> SEQ ID NO 129
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 129
aactgtacaa actactacct ca                                             22

<210> SEQ ID NO 130
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 130
ggtcagacgt agggtattga atgagtg                                        27

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
tcaataccct acgtctgacc                                                20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
```
tcaataccct acgtctgacc                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
gtagtttgta cagttagtcg                                              20

<210> SEQ ID NO 134
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 134
gagtggacgt agggtattga atgagtggac gtcgggtatt gaatgagtg              49

<210> SEQ ID NO 135
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 135
gacgtagggt attaaatgag tggacgtagg gtactgaatg agtg                   44

<210> SEQ ID NO 136
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 136
tgaggtagta gtttgtatag tttgaggtag tactttgtac agtt                   44

<210> SEQ ID NO 137
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 137
tgtggtagta gtttgtacag tttgaggtag tagtttgtac agtttgagg              49

<210> SEQ ID NO 138
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 138
cctcaaactg tacaaactac tacctcaaac tgtacaaact actaccaca              49

<210> SEQ ID NO 139
<211> LENGTH: 44
<212> TYPE: DNA

<213> ORGANISM: Artificial Sequence
<220> FEATURE:
<223> OTHER INFORMATION: Synthetic Oligonucleotide

<400> SEQUENCE: 139
aactgtacaa agtactacct caaactatac aaactactac ctca        44

<210> SEQ ID NO 140
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 140
cactcattca gtaccctacg tccactcatt taatacccta cgtc        44

<210> SEQ ID NO 141
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 141
cactcattca atacccgacg tccactcatt caatacccta cgtccactc        49

<210> SEQ ID NO 142
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 142
gagtggacgt cgggtattga atgagtggac gtagggtatt gaatgagtg        49

<210> SEQ ID NO 143
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 143
gacgtagggt attaaatgag tggacgtagg gtactgaatg agtg        44

<210> SEQ ID NO 144
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 144
tgaggtagta gtttgtatag tttgaggtag tactttgtac agtt        44

<210> SEQ ID NO 145
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 145
tgaggtagta gtttgtacag tttgtggtag tagtttgtac agtttgagg        49

```
<210> SEQ ID NO 146
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 146
cctcaaactg tacaaactac tacctcaaac tgtacaaact actaccaca            49

<210> SEQ ID NO 147
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 147
aactgtacaa agtactacct caaactatac aaactactac ctca                 44

<210> SEQ ID NO 148
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 148
cactcattca gtaccctacg tccactcatt taatacccta cgtc                 44

<210> SEQ ID NO 149
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 149
cactcattca atacccgacg tccactcatt caatacccta cgtccactc             49
```

COMPOSITIONS OF TOEHOLD PRIMER DUPLEXES AND METHODS OF USE

RELATED APPLICATIONS

This application is a divisional application of U.S. application Ser. No. 13/882,231, filed Jul. 1, 2013, which is a national stage filing under 35 U.S.C. § 371 of international application number PCT/US2011/058178, filed Oct. 27, 2011, which was published under PCT Article 21(2) in English and claims priority under 35 U.S.C. § 119(e) from U.S. provisional application Ser. No. 61/407,291, filed Oct. 27, 2010, the entire contents of all of which are incorporated by reference herein.

GOVERNMENT SUPPORT

This invention was made with Government support under OD007292 awarded by National Institutes of Health, under N00014-11-1-0914 and N00014-10-1-0827 awarded by U.S. Department of Defense, Office of Naval Research, and under CCF 1054898 awarded by National Science Foundation. The Government has certain rights in the invention.

FIELD OF INVENTION

The embodiments described herein relate to partially double-stranded nucleic acid primers and their use in, for example, nucleic acid synthesis methods.

BACKGROUND OF INVENTION

Nucleic acids are vital information carriers of biology, and the detection, amplification, and identification of nucleic acids has formed the basis for a vast sector of biotechnology. In particular, methods such as the polymerase chain reaction (PCR) (Saiki et al. *Science* 239, 487-491 (1988)) have been used all over the world as a reliable means of amplifying DNA, while reverse transcriptase methods have been used to probe the transcriptome. The operation of DNA polymerase, RNA polymerase, and reverse transcriptase typically uses a short oligonucleotide fragment known as a primer to direct the portion of a long target to be replicated or transcribed.

Although the specificity of nucleic acid hybridization is frequently sufficient to direct enzymatic activity for most target sequences, targets with repetitive sequence, secondary structure, and high G/C content are difficult to amplify with high yield. Furthermore, high backgrounds of other nucleic acids can frequently lead to incorrect amplification, such as in the case of single copy human genome amplification. Finally, multiplexed amplification, such as from a DNA chip pool, can be difficult to achieve due to the large number of orthogonal amplification reactions that must occur simultaneously. Similar problems exist for transcription and for reverse transcription.

SUMMARY OF INVENTION

The hybridization of nucleic acids is specific at the single nucleotide level. For example, cytosine preferentially binds to guanine, and adenine preferentially binds to thymine or uracil. However, for nucleic acid molecules composed of many nucleotides, the specificity of hybridization is reduced, and nucleic acids with near complementary sequences will bind almost as strongly as perfect complementary sequences. Given a heterogeneous mixture of target nucleic acid of interest ("targets") and nucleic acids with sequences that differ from the target by, for example, one nucleotide ("spurious targets"), a significant portion of primers complementary to the target will hybridize instead to spurious targets.

Because the correct targets bind with a slightly higher affinity to a primer having a complementary sequence, given enough time, correct targets will eventually displace spurious targets in binding to a complementary primer. Though, this process is very slow, and would take months at the nanomolar concentrations typical of many experimental systems.

In order to mitigate the propensity of complementary primers binding to spurious targets it is often necessary to operate nucleic acid primer-based experimental systems near the melting temperature of the primer/target complex. Because this melting temperature is generally much higher than the temperature at which most biological systems naturally operate, this high temperature requirement precludes the experimental system from operating under normal biological conditions. Additionally, because the melting temperature will vary from target to target, the requisite narrow temperature range for such experimental systems restricts the simultaneous use of multiple primers to detect a plurality of targets.

Provided herein are primers (e.g., primer duplexes and hairpin primer duplexes) that, in embodiments, are able to rapidly bind to nucleic acid targets with high specificity at a broad range of temperatures. These primers may be used, for example, in nucleic acid synthesis reactions (e.g., PCR), microarray analyses, imaging methods, and single nucleotide polymorphism (SNP) analyses. The primers may also be used in nucleic acid detection assays where they function primarily as "probes". Accordingly, regardless of the application, the primers of the invention may be referred herein to interchangeably as "probes". Regardless of the application (or method of use), the primers of the invention overcome problems commonly experienced when specific hybridization is required in the presence of spurious targets, and more particularly when such spurious targets are present in excess.

The primers provided herein possess several unique properties that facilitate their use in combination with enzymes that act upon nucleic acids. First, the primers are thermodynamically designed to bind with high specificity to only their intended targets, and they show high discrimination against even single-nucleotide changes. Second, the specificity of the primers enables PCR, transcription, and reverse transcription of traditionally difficult targets, such as those having significant sequence repetition, secondary structure, and/or high G/C content. The high degree of specificity that can be achieved with these primers further enables accurate processing even in high nucleic acid backgrounds such as single-copy human genome amplification. Third, the partially double-stranded nature of the primers means that they are unlikely to interact with each other, and consequently they are amenable to highly multiplexed replication, transcription, and/or reverse transcription reactions. Finally, the hybridization of these primers to targets is relatively robust to temperature and salinity, and therefore the primers may be of significantly greater length than standard primers, which in turn provides further enhanced specificity and primer design flexibility.

In some embodiments, the nucleic acid primers discussed here are rationally designed so that the standard free energy for hybridization (e.g., theoretical standard free energy) between the specific target nucleic acid molecule and the primer is close to zero, while the standard free energy for hybridization between a spurious target (even one differing from the specific (actual) target by as little as a single nucleotide) and the primer is high enough to make their binding unfavorable by comparison. The inventors accomplished this by designing a primer having (a) a "toehold" single-stranded target specific region, (b) a "branch migration" double-stranded target specific region, and (c) a "balance" double-stranded target non-specific region.

In some embodiments, the primer may be comprised of a single strand that self hybridizes to form double-stranded regions. In some embodiments, the primer may be comprised of two strands. As an example of the latter embodiment, the primers is comprised of a first or complement strand and a second or protector strand. The complement strand, as its name implies, is partially complementary to the target of interest and will hybridize to the target. The protector strand, on the other hand, is designed to not hybridize to the target and rather to compete with the target (or spurious target) for binding of the complement.

The "toehold" region is present in the complement strand, is complementary to a target sequence and not complementary to a protector region. The "balance" region in the complement strand (i.e., the complement balance region) is complementary to part of the protector (i.e., to the protector balance region) and not complementary to target sequence. The hybridization energy of toehold to target is matched or nearly matched to the hybridization energy of complement balance region to protector balance region (adjusting for various other thermodynamic considerations). The sequence of the balance region is rationally designed to achieve this matching under desired conditions of temperature and primer concentration. As a result, the equilibrium for the actual target and primer rapidly approaches 50% target:primer:protector:primer (or whatever ratio is desired), while equilibrium for the spurious target and primer greatly favors protector:primer. The abundant free primer in the presence of specific target facilitates its highly sensitive and specific detection.

In some embodiments, the nucleic acid primers discussed here are designed so that the concentration-adjusted free energy for hybridization between the specific target nucleic acid molecule and the primer is close to zero, while the concentration-adjusted standard free energy for hybridization between a spurious target and the primer is high enough to make their binding unfavorable by comparison. "Concentration-adjusted free energy," as used herein, refers to $\Delta G°+(\Delta n)RT \ln(c)$, where R is the universal gas constant, T is temperature in Kelvins, c is concentration of the primer, and $\Delta n$ is the change in the number of molecules through the course of the reaction ($\Delta n=-1$ for standard hybridization, $\Delta n=0$ for two-stranded primer hybridization.

Aspects of the invention therefore provide the primer compositions comprising the primers, compositions comprising the complement and protector strands (for example in kits), methods of making the primers, and methods of using the primers in assays or reactions including without limitation nucleic acid synthesis and/or detection assays or reactions.

Thus, in one aspect, the invention provides a partially double-stranded primer comprised of (a) first nucleic acid strand (also referred to herein as a complement strand) and second nucleic acid strand (also referred to herein as a protector strand), wherein the first and second strands when hybridized to each other are arranged into (1) a double-stranded target-non-specific (balance) region, (2) a double-stranded target-specific (branch migration) region, and (3) a single-stranded target-specific (toehold) region contributed to by the first nucleic acid strand, wherein the double-stranded target-non-specific region has a standard free energy approximately equal to the standard free energy for the single-stranded target-specific region bound to a target nucleic acid. The partially double-stranded primer may comprise one or more double-stranded target-non-specific regions, one or more double-stranded target-specific regions, and/or one or more single-stranded target-specific regions. In some embodiments, the partially double-stranded primer may comprise one or two double-stranded target-non-specific (balance) regions, one or more double-stranded target-specific (branch migration) regions, and/or one or more single-stranded target-specific (toehold) regions.

In some embodiments, the second nucleic acid strand comprises a non-extendable nucleotide at its 3' end and/or the first nucleic acid strand comprises a non-natural nucleotide at or near the 3' end of its target-non-specific region. In some embodiments, the non-extendable nucleotide is a non-natural nucleotide or a dideoxy nucleotide. In some embodiments, the non-natural nucleotide is iso-C, iso-G or deoxyuridine. These examples are intended as non-limiting.

In some embodiments, the double-stranded target non-specific region is about 4-20 nucleotides in length. The double-stranded target non-specific region may be longer than 20 nucleotides, such as for example 4-21 nucleotides in length. In some embodiments, it may be about 12-192 nucleotides in length.

In some embodiments, the single stranded target specific region is about 4-20 nucleotides in length. The single stranded target specific region may be longer than 20 nucleotides, such as for example 4-21 nucleotides in length. In some embodiments, it may be about 12-192 nucleotides in length.

In some embodiments, the double-stranded target non-specific region and the single stranded target specific region have similar or identical proportions of A/T nucleotides (and typically similar or identical proportions of G/C nucleotides). In some embodiments, the first and second nucleic acid strands are comprised of DNA or RNA or a combination thereof.

In another aspect, the invention provides a single-stranded primer that partially self-hybridizes to form (1) a double-stranded target-non-specific region, (2) a double-stranded target-specific region, (3) single-stranded target-specific region, and (4) a hairpin loop region, wherein the one or more double-stranded target-non-specific region has a concentration-adjusted standard free energy approximately equal to the concentration-adjusted standard free energy for the one or more single-stranded target-specific region bound to a target nucleic acid.

In another aspect, the invention provides a composition comprising the any of the afore-mentioned primers. The composition may further comprise a carrier such as a buffer, optionally comprising a preservative, one or more salts, etc. The composition may also comprise an excess of single-stranded protector strands, wherein each protector strand comprises a protector balance region and a protector branch migration region. The single stranded protector strands may each comprise a non-extendable and/or non-naturally occurring nucleotide, preferably at its 3' end.

In another aspect, the invention provides a system comprising a nucleic acid target, a polymerase, and any of the foregoing primers. In some embodiments, the primer is a partially double-stranded primer comprising a first and a second nucleic acid strand arranged into (1) a double-stranded target-non-specific region, (2) a double-stranded target-specific region, and (3) a single-stranded target-specific region contributed to by the first nucleic acid strand.

In some embodiments, the nucleic acid target is a single-stranded. In some embodiments, the nucleic acid target is DNA or RNA. In some embodiments, the nucleic acid target comprises repetitive sequence, secondary structure and/or high GC content. In some embodiments, the nucleic acid target is present in a plurality of different nucleic acids. In some embodiments, the nucleic acid target is present as a single copy or in low copy (e.g., less than 0.001%, less than 0.01%, less than 0.1%, or less than 1%) in a plurality of different nucleic acids.

In some embodiments, the system comprises a plurality of any of the foregoing primers such as a plurality of different partially double-stranded primers. In some embodiments, the system comprises at least two of the foregoing primers, such as at least two partially double-stranded primers, which together can be used to amplify a region of the nucleic acid target.

In another aspect, the invention provides a composition comprising the any of the afore-mentioned systems. The composition may further comprise a carrier such as a buffer, optionally comprising a preservative, one or more salts, one or more enzymes such as a polymerase, nucleotides suitable for nucleic acid synthesis, etc. The composition may also comprise an excess of single-stranded protector strands, wherein each protector strand comprises a protector balance region and a protector branch migration region. The single stranded protector strands may each comprise a non-extendable and/or non-naturally occurring nucleotide, preferably at its 3' end.

In another aspect, the invention provides a method comprising contacting any of the foregoing primers, including any of the foregoing partially double-stranded primers to a sample, and detecting hybridization of the primer to a target in the sample.

In some embodiments, the primer such as the partially double-stranded primer is labeled with a detectable moiety. In some embodiments, the detectable moiety comprises a fluorophore or a radioisotope.

The target will typically be a nucleic acid. In some embodiments, the target is a single-stranded nucleic acid. In some embodiments, the target is DNA or RNA. In some embodiments, the target is a nucleic acid that comprises repetitive sequence, secondary structure and/or high GC content. In some embodiments, the target is present in a plurality of different nucleic acids. In some embodiments, the target is present as a single copy or in low copy (e.g., less than 0.001%, less than 0.01%, less than 0.1%, or less than 1%) in a plurality of different nucleic acids.

In some embodiments, this and other methods described herein are performed at a temperature below the melting temperature of the complement strand-target complex. In some embodiments, this and other methods described herein are performed at a temperature between and including room temperature up to and including 50° C., or up to and including 40° C., or up to and including 30° C. In some embodiments, this and other methods described herein are performed at about 37° C. In some embodiments, this and other methods described herein are performed in an excess of protector strand that comprises a protector balance region and a protector branch migration region and that is identical to the protector strand in the partially double-stranded primer. In this and other methods described herein, the primer may be any of the foregoing primers including the partially double-stranded primers.

In another aspect, the invention provides a method comprising hybridizing a single-stranded target-specific (toe-hold) region of a first (complement) strand of any of the foregoing partially double-stranded primers to a nucleic acid target, thereby dissociating the first strand of the primer from the second (protector) strand of the primer, and extending the first strand at its 3' end, in a target-complementary manner, in the presence of a polymerase.

In another aspect, the invention provides a method comprising performing a nucleic acid synthesis reaction in the presence of a nucleic acid target, a polymerase, and one or more of the foregoing partially double-stranded primers.

In some embodiments, the nucleic acid synthesis reaction is a nucleic acid amplification reaction. In some embodiments, the nucleic acid amplification reaction is polymerase chain reaction (PCR). In some embodiments, the nucleic acid synthesis reaction is a transcription reaction. In some embodiments, the transcription reaction is a reverse transcription reaction.

In some embodiments, two partially double-stranded primers are used.

In another aspect, the invention provides a method of performing a multiplexed nucleic acid amplification reaction comprising amplifying multiple unique nucleic acid molecules using any of the foregoing primers including the partially double-stranded primer.

In another aspect, the invention provides a kit comprising one or more (including a plurality) of any of the foregoing partially double-stranded primers, and one or more nucleic acid synthesis reagents such as enzymes, nucleotides, salts, EDTA, a buffer, etc.

In some embodiments, the one or more nucleic acid synthesis reagents is selected from the group consisting of a buffer, nucleotides, and a polymerase.

In some embodiments, the kit further comprises an excess of protector strand that is identical to the protector strand comprised in the primer.

In some embodiments, the kit further comprises instructions for use.

In another aspect, the invention provides a kit comprising a first single-stranded (complement) nucleic acid in a first container, and a second single-stranded (protector) nucleic acid that is complementary to a region of the first single-stranded nucleic acid, in a second container, wherein, when the first and second single-stranded nucleic acids are hybridized to each other, a partially double-stranded nucleic acid is formed that comprises (1) a double-stranded target-non-specific region, (2) a double-stranded target-specific region, and (3) a single-stranded target-specific region contributed to by the first nucleic acid, wherein the first single-stranded nucleic acid comprises a non-natural nucleotide and/or the second single-stranded nucleic acid comprises a non-extendable nucleotide at its 3' end.

In some embodiments, the kit further comprises instructions for use. In some embodiments, the kit further comprises one or more nucleic acid synthesis reagents such as those recited above. In some embodiments, the one or more nucleic acid synthesis reagents is selected from the group consisting of a buffer, nucleotides, and a polymerase.

In some embodiments, the protector strand is provided in the kit in an amount (e.g., a molar amount) that is greater than the amount (e.g., a molar amount) of complement strand in the kit.

In some embodiments of the foregoing aspects and inventions, particularly those relating to two strand primers, the nucleotide sequence of the primer is selected such that: $|\Delta G_1° - \Delta G_2° - \Delta G_3°| \leq \Delta G_R°$, wherein: $\Delta G_1°$ is the standard free energy of hybridization of the protector balance region to the complement balance region; $\Delta G_2°$ is the standard free energy of hybridization of the protector balance region to the sequence immediately adjacent in the first direction to the target nucleic acid sequence, if any; $\Delta G_3°$ is the standard free energy of hybridization of the toehold region to the second target nucleic acid sequence; and $\Delta G_R°$ is 3.5 kcal/mol.

In one aspect, provided herein is a primer duplex system comprising a complement strand and a protector strand, wherein the protector strand comprises a nucleic acid having: a protector branch migration region having a first end, a second end, and a sequence that corresponds to a first target nucleic acid sequence having a first end and a second end, wherein the first end of the protector branch migration region and the first end of the first target nucleic acid sequence are either both 5' or else both 3'; and a protector balance region immediately adjacent to the first end of the protector branch migration region having a sequence that does not correspond to sequence immediately adjacent to the first end of the first target nucleic acid sequence, if any; and the complement primer comprises a nucleic acid having: a complement branch migration region having a first end and a second end, and a sequence that is complementary to the protector branch migration region, wherein the first end of the complement branch migration region and the first end of the first target nucleic acid sequence are either both 5' or else both 3'; toehold region that is: immediately adjacent to the first end of the complement branch migration region; and complementary to a second target nucleic acid sequence that is immediately adjacent to the second end of the first target nucleic acid sequence; and a complement balance region that: is immediately adjacent to the second end of the complement branch migration region; is complementary to the protector balance region; and has a sequence such that: $|\Delta_1°-\Delta G_2°-\Delta G_3°|\leq \Delta G_R°$, wherein: $\Delta G_1°$ is the standard free energy of hybridization of the protector balance region to the complement balance region; $\Delta G_2°$ is the standard free energy of hybridization of the protector balance region to the sequence immediately adjacent in the first direction to the target nucleic acid sequence, if any; $\Delta G_3°$ is the standard free energy of hybridization of the toehold region to the second target nucleic acid sequence; and $\Delta G_R°$ is 3.5 kcal/mol.

In another aspect, provided herein is a primer duplex system comprising a nucleic acid having a protector strand, a hairpin region and a complement strand, wherein: the protector strand comprises a protector branch migration region and a protector balance region, wherein: the protector branch migration region has: a first end; a second end; and a sequence that corresponds to a first target nucleic acid sequence having a first end and a second end, wherein the first end of the protector branch migration region and the first end of the first target nucleic acid sequence are either both 5' or else both 3'; and the protector balance region has: a first end; a second end immediately adjacent to the first end of the protector branch migration region; and a sequence that does not correspond to sequence immediately adjacent to the first end of the first target nucleic acid sequence, if any; the hairpin region comprises: a first end; and a second end immediately adjacent to the first end of the protector balance region; and the complement strand comprises a complement balance region, a complement branch migration region, and a toehold region, wherein: the complement balance region has: a first end; a second end immediately adjacent to the first end of the hairpin region; and a sequence that is complementary to the protector balance region; the comple-ment branch migration region has: a first end; a second end immediately adjacent to the first end of the complement balance region; and a sequence that is complementary to the protector branch migration region, wherein the first end of the complement branch migration region and the first end of the first target nucleic acid sequence are either both 5' or else both 3'; the toehold region is: immediately adjacent to the first end of the complement branch migration region; and complementary to a second target nucleic acid sequence that is immediately adjacent to the second end of the first target nucleic acid sequence; and the complement balance region has a sequence such that: $|\Delta G_1-\Delta G_2°-\Delta G_3°+\Delta G_4°+RT\ln(c)|\leq \Delta G_R°$, wherein: $\Delta G_1°$ is the standard free energy of hybridization of the protector balance region to the complement balance region; $\Delta G_2°$ is the standard free energy of hybridization of the protector balance region to the sequence immediately adjacent in the first direction to the target nucleic acid sequence, if any; and $\Delta G_3°$; is the standard free energy of hybridization of the toehold region to the second target nucleic acid sequence; $\Delta G_4°$ is the standard free energy of confinement of the hairpin region; R is the ideal gas constant; T is the temperature at which the primer duplex system is to be used; c is the concentration at which the primer duplex system is to be used; and $\Delta G_R°$ is 3.5 kcal/mol.

In yet another aspect, provided herein system having, in 3' to 5' order, a first protector strand, a first hairpin region, a complement strand, a second hairpin region and a second protector strand, wherein: the first protector strand comprises: a first protector branch migration region having a sequence that corresponds to a first target nucleic acid sequence; and a first protector balance region that: is immediately 5' to the first protector branch migration region; and has a sequence that does not correspond to sequence immediately 5' to the first target nucleic acid sequence, if any; the first hairpin region is immediately 5' to the first protector balance region; the complement strand comprises: a first complement balance region that: is immediately 5' to the first hairpin region; and has a sequence complementary to the sequence of the first protector balance region; a first complement branch migration region that: is immediately 5' to the first complement balance region; and has a sequence complementary to a first protector branch migration region; a toehold region that: is immediately 5' to the first complement branch migration region; and has a sequence that is complementary to a second target nucleic acid sequence that is immediately 3' to the first target nucleic acid sequence; a second complement branch migration region that: is immediately 5' to the toehold region; and has a sequence complementary to a third target nucleic acid sequence that is immediately 3' to the second target nucleic acid sequence; a second complement balance region that: is immediately 5' to the second complement branch migration region; has a sequence that is not complementary to sequence immediately 3' to the third target nucleic acid sequence, if any; the second hairpin region is immediately 5' to the second complement balance region; and the second protector strand comprises: a second protector balance region that: is immediately 5' to the second hairpin region; and has a sequence complementary to the second complement balance region; and a second protector branch migration region that: is immediately 5' to the second protector balance region; and has a sequence complementary to the second complement branch migration region; wherein the first complement balance region and the second complement balance region have sequences such that: $|\Delta G_1°-\Delta G_2°+\Delta G_3°-\Delta G_4°-\Delta G_5°+\Delta G_6°+RT\ln(c)|\leq \Delta G_R°$, wherein: $\Delta G_1+$ is the standard free energy of hybridization of the first protector balance region to the first complement balance region; $\Delta G_2°$ is the standard free energy of hybridization of the first complement balance region to the sequence immediately 5' to the first target nucleic acid sequence, if any; $\Delta G_3°$ is the standard free energy of hybridization of the second protector balance region to the second complement balance region; $\Delta G_4°$ is the standard free energy of hybridization of the second complement balance region to the sequence immediately 3' to the third target nucleic acid sequence, if any; $\Delta G_5°$ is the standard free energy of hybridization of the toehold region to the second target nucleic acid sequence; $\Delta G_6°$ is the standard free energy of confinement of the first hairpin region; $\Delta G_7°$ is the standard free energy of confinement of the second hairpin region; R is the ideal gas constant; T is the temperature at which the primer duplex system is to be used; and c is the concentration at which the primer duplex system is to be used; and $\Delta G_R°$ is 3.5 kcal/mol.

In still another aspect, provided herein is a primer duplex system comprising a hairpin primer and a protector strand, wherein: the hairpin primer comprises a nucleic acid having: a first protector strand having: a first protector branch migration region having a sequence that corresponds to a first target nucleic acid sequence; and a first protector balance region that: is immediately 5' to the first protector branch migration region; and has a sequence that does not correspond to sequence immediately 5' to the first target nucleic acid sequence, if any; a hairpin region immediately 5' to the first protector balance region; a complement strand having: a first complement balance region that: is immediately 5' to the first hairpin region; and has a sequence complementary to the sequence of the first protector balance region; a first complement branch migration region that: is immediately 5' to the first complement balance region; and has a sequence complementary to a first protector branch migration region; a toehold region that: is immediately 5' to the first complement branch migration region; and has a sequence that is complementary to a second target nucleic acid sequence that is immediately 3' to the first target nucleic acid sequence; a second complement branch migration region that: is immediately 5' to the toehold region; and has a sequence complementary to a third target nucleic acid sequence that is immediately 3' to the second target nucleic acid sequence; a second complement balance region that: is immediately 5' to the second complement branch migration region; has a sequence that is not complementary to sequence immediately 3' to the third target nucleic acid sequence, if any; and the protector comprises a nucleic acid having: a second protector strand having: a second protector balance region that has a sequence complementary to the second complement balance region; and a second protector branch migration region that: is immediately 5' to the second protector balance region; and has a sequence complementary to the second complement branch migration region; wherein the first complement balance region and the second complement balance region have sequences such that: $|\Delta G_1° - \Delta G_2° + \Delta G_3° - \Delta G_4° - \Delta G_5° + \Delta G_6°| \leq \Delta G_R°$, wherein: $\Delta G_1°$ is the standard free energy of hybridization of the first protector balance region to the first complement balance region; $\Delta G_2°$ is the standard free energy of hybridization of the first complement balance region to the sequence immediately 5' to the first target nucleic acid sequence, if any; $\Delta G_3°$ is the standard free energy of hybridization of the second protector balance region to the second complement balance region; $\Delta G_4°$ is the standard free energy of hybridization of the second complement balance region to the sequence immediately 3' to the third target nucleic acid sequence, if any; $\Delta G_5°$ is the standard free energy of hybridization of the toehold region to the second target nucleic acid sequence; $\Delta G_6°$ is the standard free energy of confinement of the hairpin region; and $\Delta G_R°$ is 3.5 kcal/mol.

In a further aspect, provided herein is a primer duplex system comprising a protector strand and a hairpin primer, wherein: the protector strand comprises a nucleic acid having: a first protector strand having: a first protector branch migration region having a sequence that corresponds to a first target nucleic acid sequence; and a first protector balance region that: is immediately 5' to the first protector branch migration region; and has a sequence that does not correspond to sequence immediately 5' to the first target nucleic acid sequence, if any; the hairpin primer comprises a nucleic acid having: a complement strand having: a first complement balance region that has a sequence complementary to the sequence of the first protector balance region; a first complement branch migration region that: is immediately 5' to the first complement balance region; and has a sequence complementary to a first protector branch migration region; a toehold region that: is immediately 5' to the first complement branch migration region; and has a sequence that is complementary to a second target nucleic acid sequence that is immediately 3' to the first target nucleic acid sequence; a second complement branch migration region that: is immediately 5' to the toehold region; and has a sequence complementary to a third target nucleic acid sequence that is immediately 3' to the second target nucleic acid sequence; a second complement balance region that: is immediately 5' to the second complement branch migration region; has a sequence that is not complementary to sequence immediately 3' to the third target nucleic acid sequence, if any; a hairpin region immediately 5' to the second complement balance region; and a second protector strand having: a second protector balance region that: is immediately 5' to the second hairpin region; and has a sequence complementary to the second complement balance region; and a second protector branch migration region that: is immediately 5' to the second protector balance region; and has a sequence complementary to the second complement branch migration region; wherein the first complement balance region and the second complement balance region have sequences such that: $|\Delta G_1° - \Delta G_2° + \Delta G_3° - -\Delta G_4° - \Delta G_5° + \Delta G_6°| \leq \Delta G_R°$, wherein: $\Delta G_1°$ is the standard free energy of hybridization of the first protector balance region to the first complement balance region; $\Delta G_2°$ is the standard free energy of hybridization of the first complement balance region to the sequence immediately 5' to the first target nucleic acid sequence, if any; $\Delta G_3°$ is the standard free energy of hybridization of the second protector balance region to the second complement balance region; $\Delta G_4°$ is the standard free energy of hybridization of the second complement balance region to the sequence immediately 3' to the third target nucleic acid sequence, if any; and $\Delta G_5°$ is the standard free energy of hybridization of the toehold region to the second target nucleic acid sequence; $\Delta G_6°$ is the standard free energy of confinement of the hairpin region; and $\Delta G_R°$ is 3.5 kcal/mol.

In another aspect, provided herein is a primer duplex system comprising a first protector strand, a complement strand and a second protector strand, wherein: the first protector strand comprises a nucleic acid having: a first protector branch migration region having a sequence that corresponds to a first target nucleic acid sequence; and a first protector balance region that: is immediately 5' to the first protector branch migration region; and has a sequence that does not correspond to sequence immediately 5' to the first target nucleic acid sequence, if any; the complement strand comprises a nucleic acid having: a first complement balance region that: is immediately 5' to the first hairpin region; and has a sequence complementary to the sequence of the first protector balance region; a first complement branch migration region that: is immediately 5' to the first complement balance region; and has a sequence complementary to a first protector branch migration region; a toehold region that: is immediately 5' to the first complement branch migration region; and has a sequence that is complementary to a second target nucleic acid sequence that is immediately 3' to the first target nucleic acid sequence; a second complement branch migration region that: is immediately 5' to the toehold region; and has a sequence complementary to a third target nucleic acid sequence that is immediately 3' to the second target nucleic acid sequence; a second complement balance region that: is immediately 5' to the second complement branch migration region; has a sequence that is not complementary to sequence immediately 3' to the third target nucleic acid sequence, if any; and the second protector strand comprises: a second protector balance region that has a sequence complementary to the second complement balance region; and a second protector branch migration region that: is immediately 5' to the second protector balance region; and has a sequence complementary to the second complement branch migration region; wherein the first complement balance region and the second complement balance region have sequences such that: $|\Delta G_1°-\Delta G_2°+\Delta G_3°-\Delta G_4°-\Delta G_5°-RT \ln(c)| \leq \Delta G_R°$, wherein: $\Delta G_1°$ is the standard free energy of hybridization of the first protector balance region to the first complement balance region; $\Delta G_2°$ is the standard free energy of hybridization of the first complement balance region to the sequence immediately 5' to the first target nucleic acid sequence, if any; $\Delta G_3°$ is the standard free energy of hybridization of the second protector balance region to the second complement balance region; $\Delta G_4°$ is the standard free energy of hybridization of the second complement balance region to the sequence immediately 3' to the third target nucleic acid sequence, if any; and $\Delta G_5°$ is the standard free energy of hybridization of the toehold region to the second target nucleic acid sequence; R is the ideal gas constant; T is the temperature at which the primer duplex system is to be used; c is the concentration at which the primer duplex system is to be used; and $\Delta G_R°$ is 3.5 kcal/mol.

In yet another aspect, provided herein is a primer duplex system comprising, in 3' to 5' order, a first protector strand, a first hairpin region, a complement strand, a second hairpin region and a second protector strand, wherein: the first protector strand has a sequence that corresponds to a first target nucleic acid sequence; the first hairpin region is immediately 5' of the first protector strand; the complement strand comprises: a first complement branch migration region that: is immediately 5' of the first hairpin region; and has a sequence complementary to the sequence of the first protector strand; a toehold region that: is immediately 5' of the first complement branch migration region; and has a sequence complementary to a second target nucleic acid sequence that is immediately 3' of the first target nucleic acid sequence; and a second complement branch migration region that: is immediately 5' of the toehold region; and has a sequence complementary to a third target nucleic acid sequence that is immediately 3' of the second nucleic acid sequence; the second hairpin region is immediately 5' of the second complement branch migration region; and the second protector strand has a sequence that is complementary to the sequence of the second complement branch migration region.

In any one of the foregoing aspects, $\Delta G_R°$ may be 2.0 kcal/mol, 1.0 kcal/mol, or 0.5 kcal/mol; and/or c may be about 10 nM; and/or T may be about 293 K or about 338 K; and/or the toehold region may be between 4 and 20 nucleotides in length, between about 4 and 15 nucleotides in length, or between about 4 and 10 nucleotides in length; and/or the first end of the protector branch migration region may be 5' or 3'; and/or the primer duplex system may further comprise a functionalized fluorescent group or dye; and/or the primer duplex system may be immobilized on a solid support; and/or the hairpin region may be no greater than 20 nucleotides in length or no greater than 10 nucleotides in length; and/or the sequence of the hairpin region may be selected from the group consisting of a poly-adenosine sequence, poly-deoxyadenosine sequence, a poly-5'-methyluridine sequence, a poly-thymidine sequence, a poly-guanosine sequence, a poly-deoxyguanosine sequence, a poly-cytidine sequence, a poly-deoxycytidine sequence, a poly-uridine sequence, and a poly-deoxyuridine sequence; and/or the first target nucleic acid sequence and/or the second target nucleic acid sequence may be sequences that naturally occur in an organism or a virus; and/or the first target nucleic acid sequence and/or the second target nucleic acid sequence may be sequences that naturally occur in a micro-RNA.

In one aspect, provided herein is a method of detecting a target nucleic acid in a sample comprising: contacting a target nucleic acid with a primer duplex system of any one of the embodiments described herein; and detecting the formation of a complex between the target nucleic acid and at least a part of the primer duplex system. In some embodiments, the primer duplex system further comprises a functionalized fluorescent group or dye. In some embodiments, the primer duplex system is immobilized on a solid support. In some embodiments, the contacting occurs in a cell. In some embodiments, the target nucleic acid is a nucleic acid that naturally occurs in an organism or a virus. In some embodiments, the target nucleic acid is a micro-RNA.

In another aspect, provided herein is a method of amplifying a sequence contained within a target nucleic acid comprising: forming a solution comprising: a target nucleic acid; a primer duplex system of any one of the embodiments described herein; and reagents for performing an amplification reaction; and incubating the solution under conditions such that a sequence contained within the target nucleic acid is amplified. In some embodiments, the target nucleic acid is a nucleic acid that naturally occurs in an organism or a virus.

These and other aspects and embodiments of the invention will be explained in greater detail herein.

BRIEF DESCRIPTION OF DRAWINGS

FIGS. 1A, 1B, 2A, 2B, 3A, 3B, 4-8, 9A, and 9B depict exemplary nucleic acid probe systems.

DETAILED DESCRIPTION OF INVENTION

Figure 1A:
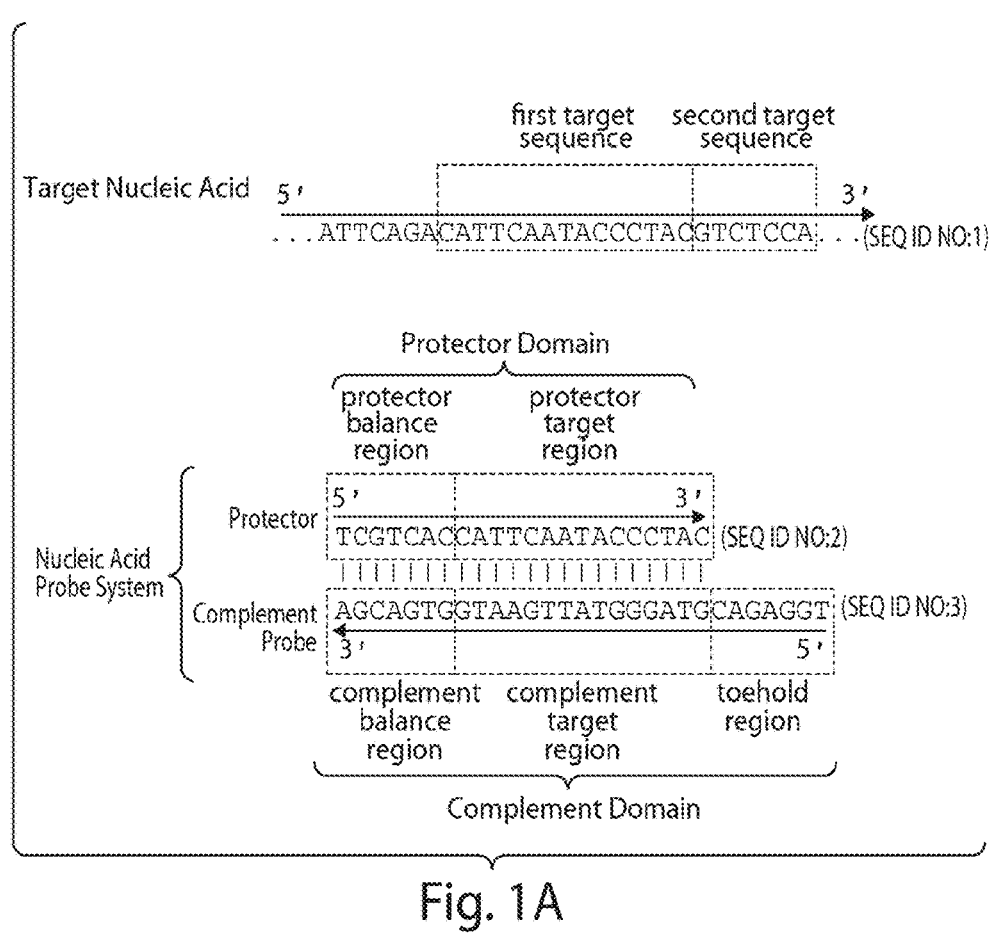

A significant challenge in probe-based nucleic acid assays is that nucleic acids having sequences similar to that of a target will hybridize to the target's complement with strong thermodynamics and fast kinetics. However, as described herein, the kinetics and thermodynamics of strand displacement reactions can be partially decoupled, so that reactions that are only slightly thermodynamically favorable or even unfavorable can nonetheless have kinetics as fast as the hybridization of two complementary strands. The compositions and methods described herein take advantage of this decoupling mechanism to provide nucleic acid probe systems with improved specificity and kinetics.

Provided herein are highly specific nucleic acid probe systems and methods of using such probe systems. In certain embodiments, the nucleic acid probe systems described herein comprise complement probes having regions complementary to a target sequence that are protected from hybridization to spurious targets by protector regions complementary to a portion of the complement probes. The free energy of the binding reaction between the target and the protected probe is finely controlled via the rationally designed bases of one or more balancing regions, which have sequences that do not correspond to the target nucleic acid sequence or its complement. In certain embodiments, a protector and a complement probe form regions on a single nucleic acid molecule and are separated from one another by one or more nucleic acid hairpins.

The methods and compositions described herein possess several unique properties that facilitate their use in hybridization assays. First, the nucleic acid probe systems described herein reliably convert small sequence differences between targets and spurious targets into large differences in binding affinity and reaction rates between hybridization of the target vs. spurious target with the probe. Second, the nucleic acid probe systems described herein can be designed to operate at any of a wide range of temperatures and salt concentrations, and can therefore function reliably under many different experimental conditions. Third, use of the nucleic acid probe systems described herein can result in hybridization reactions that are kinetically fast even at room temperature, which facilitates rapid and high-throughput analysis of nucleic acids. Fourth, the nucleic acid probe systems described herein are rationally designed, and therefore are unlikely to interact unfavorably or in unexpected ways with other biomolecules.

Accordingly, provided herein are primer compositions, methods of making such compositions, and methods of their use. The embodiments described herein are premised in part on the discovery that primer (e.g., a pair of partially hybridized primers, or a single self-hybridizing primer) that are partially double-stranded and partially single-stranded, when used in a nucleic acid synthesis reaction for example, are able to discriminate between fully complementary targets and those having one or more mismatches (i.e., spurious targets). As demonstrated herein, the primer duplexes described herein are superior to standard primers in, for example, PCR reactions using spurious targets such as those having quasi-repetitive sequences.

The primer duplexes herein comprise a single-stranded region referred to herein as a "toehold" from which the primer duplex initiates binding to a target, a double-stranded "balance region" which spontaneously dissociates so that a single primer strand does not complete hybridization (along the full length of the primer) to the target, and a double-stranded branch migration region, in between the toehold and balance regions, which is fully complementary to a target nucleic acid sequence. Mechanistically, it is thought that hybridization to a target begins at the toehold and continues along the length of the complement strand until the primer is no longer "double-stranded". This assumes complementarity between the target and the branch region as well. As used herein, a nucleic acid "region" or "domain" is a consecutive stretch of nucleotides of any length. When nucleotide mismatches exist between the "target" and the complement strand, displacement of the second strand (i.e., the protector strand) is thermodynamically unfavorable and the association between the complement strand and the "target" is reversed. It is to be understood that in this latter description, the "target" is actually a spurious target since it comprises nucleotide differences or mismatches from the complement strand.

Because the standard free energy favors a complete match (fully complementary) between the target sequence of the nucleic acid and branch migration plus toehold regions of the primer rather than a mismatch (e.g., single nucleotide change), the first (complement) strand of the primer will bind stably to a target in the absence of a mismatch but not in the presence of a mismatch. If a mismatch exists between the first (complement) strand of the primer and the target, the primer duplex prefers to reform via newly exposed single-stranded balance regions. In this way, the frequency of beginning a nucleic acid synthesis reaction at an incorrect position in a target (or in a sample, for that matter) is reduced. This type of discrimination is typically not possible using the standard single-stranded primers of the prior art because in those reactions there is no competing nucleic acid strand (such as the protector strand) to which a mismatched primer strand would prefer to bind. In some embodiments, the primers described herein may be significantly longer than conventional primers (e.g., those used for polymerase chain reaction (PCR) amplification) because the instant primers rely on the presence of a competing, protector strand for specificity rather than on melting temperature to discriminate between complementary and mismatched sequences. Accordingly, the instant primers may be selected and used in a manner that is temperature independent.

The primer duplexes described herein therefore improve specificity of for example nucleic acid synthesis reactions and, in some embodiments, allow for a greater degree of multiplexing of primers. Preliminary experiments, the results of which are provided herein, show that the PCR yield of quasi-repetitive targets can be significantly improved using the primer duplexes provided herein as compared to standard primers (e.g., 75% vs. 30%). The primer duplexes described herein also provide for specific nucleic acid detection and amplification from a heterogeneous population of nucleic acids, such as for example, detecting and amplifying a bacterial DNA from a sample comprised of human DNA, which has broad applicability in detection of rare organisms such as biowarfare agents.

Primer Duplexes

As used herein, the primers of the invention may be referred to as "primer duplexes" to covey that they may be provided and/or exist in a conformation in which they comprise double-stranded regions. Accordingly, the terms "primer" and "primer duplex" may be used interchangeably.

Figure 1B:
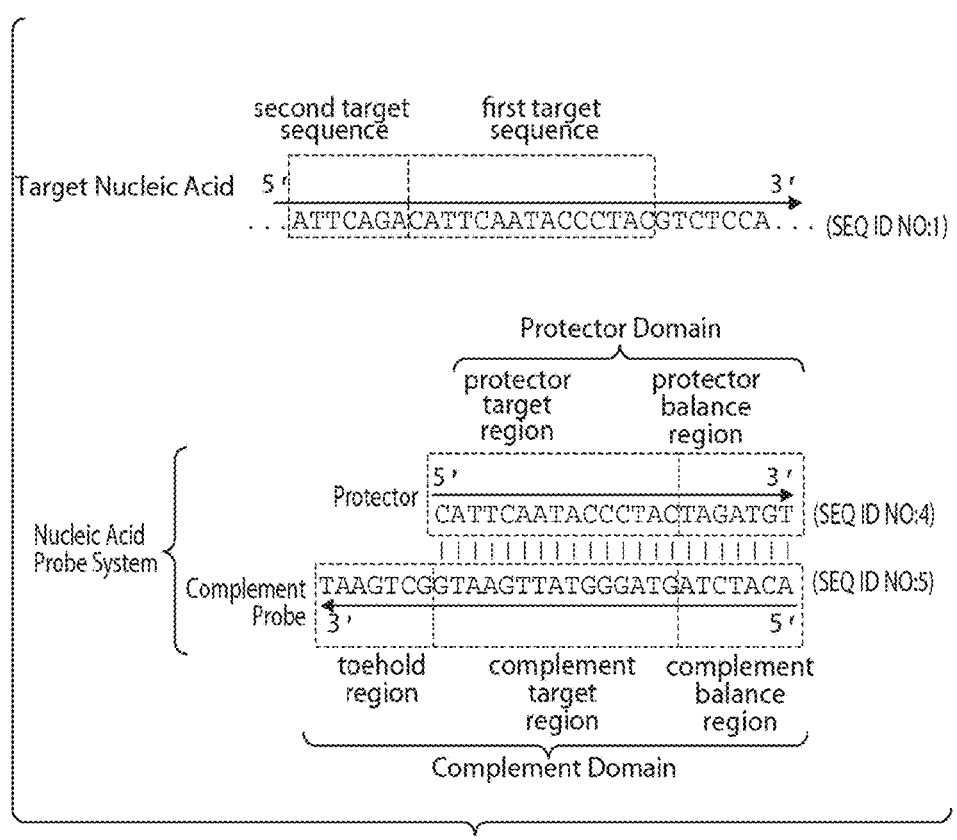
Figure 2A:
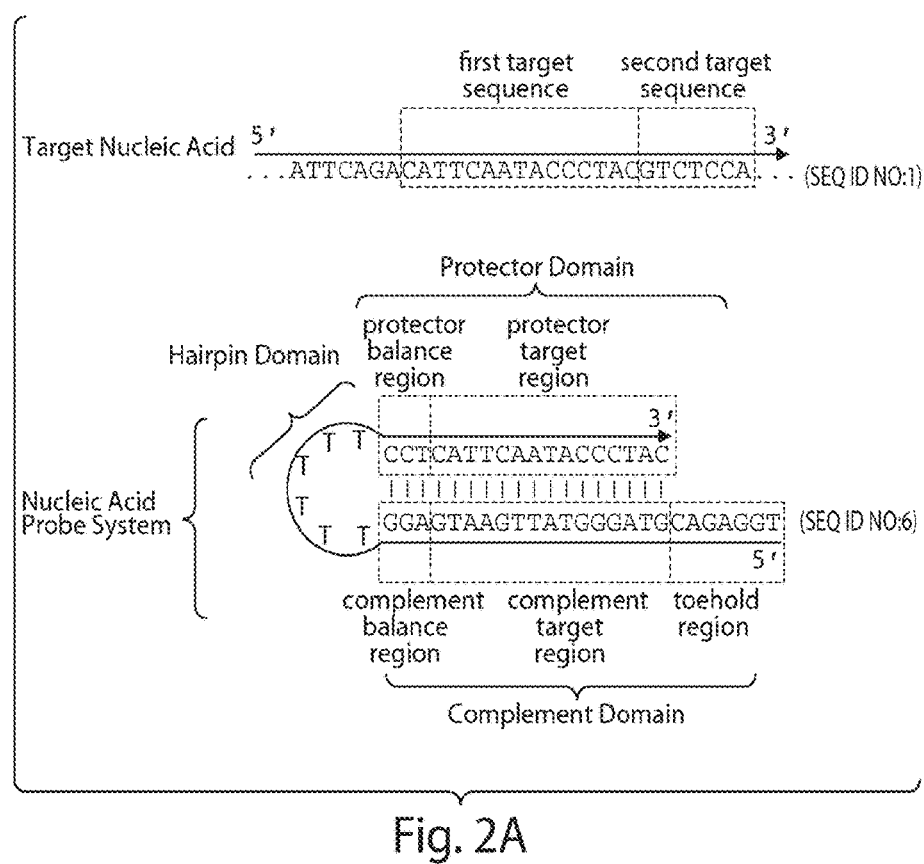
Figure 2B:
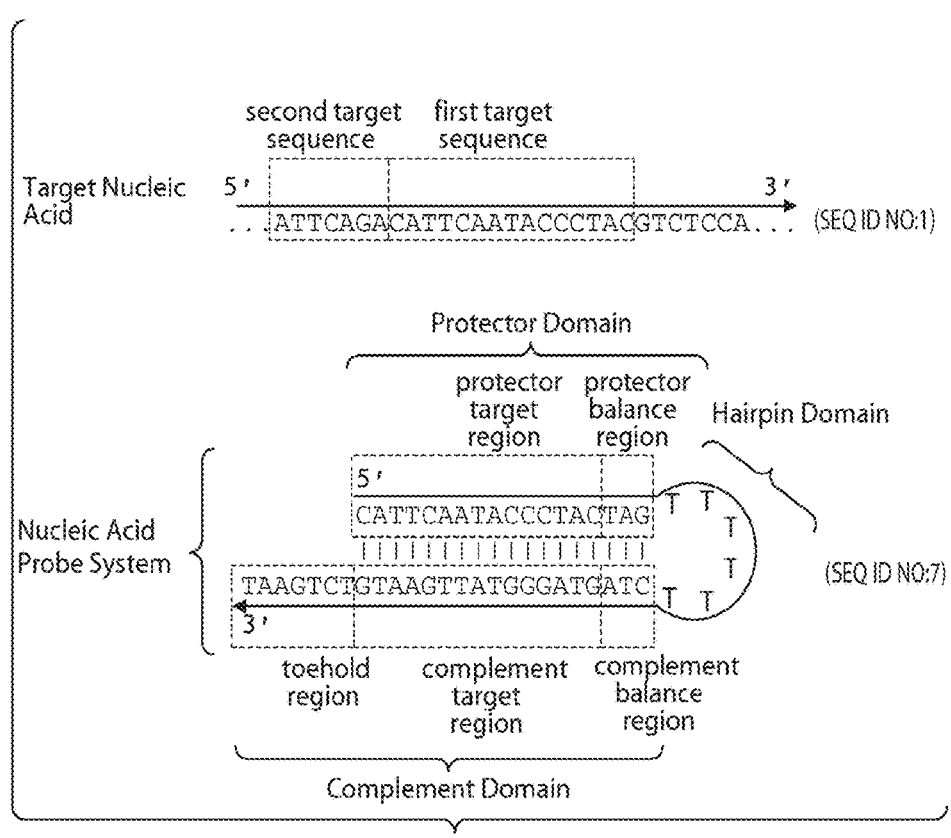

The primer duplexes provide improved specificity and kinetics over existing primers. A "primer duplex" herein refers to a primer comprising a first strand (referred to herein as a "complement strand") and a second strand (referred to herein as a "protector strand") partially complementary to the first strand. In some embodiments, the complement strand and the protector strand are separate single-stranded nucleic acid molecules (FIGS. 1A and 1B). In other embodiments, the complement strand and the protector strand are connected to each other and separated by a hairpin region to form contiguous regions of a single nucleic acid molecule (FIGS. 2A and 2B). As used herein, a "hairpin region" is a single-stranded loop of nucleotides connecting two double-stranded regions of a nucleic acid. The general structure of exemplary primer duplexes is illustrated in the Figures and described herein. It is to be understood that, in most instances, when reference is made to a complement region or a protector region (or vice versa), each region is typically within a single "primer duplex" (or a single primer system). For example, a complement balance region in a primer of the invention is complementary to a protector balance region in the same primer such that a complement balance region of one primer of the invention does not hybridize to a protector balance region of different physically separate primer.

In embodiments in which the primer of the invention consists of only a single strand, the complement "strand" may be referred to as the complement region, and the protector "strand" may be referred to as the protector region.

In certain embodiments, the complement strand (or region) comprises a toehold region, a complement branch migration region, and a complement balance region, while the protector strand (or region) comprises a protector branch migration region and a protector balance region. As used herein, a nucleic acid "region" is a consecutive stretch of nucleotides of any length. Toehold and branch migration regions are each designed to be complementary to, and thus "base-pair" with (e.g., hybridize to), adjacent regions in a target nucleic acid. A region of a complement strand that base-pairs with a region in a target nucleic acid is referred to as a "target-specific" region. Balance regions are designed to be not complementary to, and thus to not base-pair with, a target nucleic acid. Balance regions therefore are referred to as "target-non-specific" regions. In certain aspects, when the complement strand (or region) and the protector strand (or region) are hybridized to each other (are double-stranded), a primer duplex is formed. Thus, in some aspects, a primer duplex comprises a target-specific single-stranded toehold region, a target-specific double-stranded branch migration region, and a target-non-specific double-stranded balance region (FIGS. 1A and 1B). In some instances, the primer duplex may also comprise a hairpin loop, as described in greater detail below.

The primer duplexes described herein may be designed to hybridize specifically with a target nucleic acid. The efficacy of a primer, for example, in a nucleic acid amplification reaction, depends on the specificity, efficiency, and fidelity of the primer. Typical nucleic acid primers often bind to spurious targets with a thermodynamic and kinetic profile comparable to that of the same primer binding to its intended, specific target nucleic acid, except between the melting temperatures of the mismatched duplex and the perfectly hybridized duplex. Accordingly, mismatched and perfect duplexes can be distinguished by their melting temperatures. The primers of the invention, in contrast, distinguish between spurious and true target in a relatively temperature-independent manner.

A "spurious target" herein refers to a nucleic acid molecule that differs from a target nucleic acid molecule by at least one nucleotide within the region hybridizing to the complement strand. For example, TCGACGGGG is a spurious target, if the target is TCGAAGGGG. In certain embodiments, a spurious target comprises at least 2, at least 3, at least 4, or more nucleotide changes relative to the target. Primer binding to spurious targets reduces the fidelity (accuracy) of, e.g., nucleic acid amplification. The primer duplexes presented herein are designed to alter the standard free energy of strand displacement with spurious targets, permitting discrimination between correct targets and spurious targets, including spurious targets that differ from a correct target by only one nucleotide. As described herein, the protector strand is responsible for altering the standard free energy to allow the complement strand to discriminate between correct and spurious targets.

The primers described herein are rationally designed to facilitate strand displacement reactions with finely tuned kinetics and thermodynamics such that kinetics and thermodynamics of strand displacement reactions are partially decoupled. As a result of this decoupling, reactions only slightly thermodynamically favorable or even unfavorable can nonetheless have kinetics as fast as the hybridization of two complementary strands.

For example, at 37° C. and 1 M $Na^+$, the concentration-adjusted standard free energy for hybridization of a primer to a perfectly complementary (correct or specific) target (i.e., 100% nucleotide match) is between 1.9 kcal/mol and 6.6 kcal/mol more favorable than the concentration-adjusted standard free energy for hybridization of the same primer to a spurious target for every nucleotide that the spurious target differs from the intended target. In certain embodiments, the present primer duplexes use toehold exchange strand displacement reactions to translate this 1.9 to 6.6 kcal/mol difference in concentration-adjusted standard free energy to an optimal discrimination between the target and spurious targets. An example of the thermodynamics/kinetics of primer duplex binding to a target nucleic acid is described as follows in reference to FIGS. 3A and 3B.

For purposes of this example, the target nucleic acid has at least two regions, (1) and (2). In certain embodiments, region (1) may be about 10 to about 200 (including 14-200 or 20-200) nucleotides long, while region 2 may be smaller, for example, about 4 to about 20 nucleotides long. As used herein, the terms "nucleotide" and "bases" are used interchangeably. The protector strand includes a protector branch migration region adjacent to a protector balance region (3). The protector branch migration region corresponds to target region 1, while the protector balance region (3) does not correspond to region (1) or region (2) or any region immediately 5' of the target regions. A nucleic acid sequence, domain or region is "immediately adjacent to", "immediately 5'" or "immediately 3'" to another sequence if the two sequences are part of the same nucleic acid molecule and if no bases separate the two sequences. The complement strand includes a complement balance region (3), a complement branch migration region (1), and a toehold region (2). The complement balance region (3) is complementary to the protector balance region (3), the complement branch migration region (1) is complementary to the protector branch migration region and target region (1) (i.e., the protector branch migration region and the target region (1) are identical in sequence and this both bind to the complement branch migration region (1), and the toehold region (2) is complementary to target region (2).

In certain embodiments, the balance region is designed so that its concentration-adjusted standard free energy ($\Delta G_{3:3}°$) is the same or about the same as the concentration-adjusted standard free energy for the toehold region bound to target region (2) ($\Delta G_{2:2}°$). In some instances, for a 10 nanomolar (nM) primer used in a reaction at 37° C., $|\Delta G_{2:2}°|$ and $|\Delta G_{3:3}°|$ (the vertical bars denoting absolute value) should each be less than about 11.3 kcal/mol to ensure dissociation of the full protector strand from the target.

In some embodiments, when the primer duplex interacts with a specific (correct) target nucleic acid molecule (FIG. 3A), the dissociation of (3):(3) and the association of (2):(2) balance one another, and the (1):(1) hybridization thermodynamics are identical for the target nucleic acid and for the protector strand interacting with the complement strand. The total free energy change between the two states is relatively small (e.g., about 1 kcal/mol), and the reaction quickly (e.g., less than a minute) reaches an equilibrium of about 50:50. In certain embodiments, the balance region may be designed to have standard free energy very close to that of the toehold region binding to target region 2, so that the equilibrium balance is, for example, 60:40 or 70:30. In some embodiments, the design of the balance region may also take into account other contributors to free energy change during the reaction, such as hybridization between the protector balance region and upstream target sequences (which in some instances is negligible), confinement of a hairpin (if present), intended temperature of use, and intended primer concentration.

In some embodiments, when the primer duplex instead interacts with a spurious target nucleic acid molecule (FIG. 3B), the dissociation of (3):(3) and the association of (2m):(2) are not balanced because spurious target region (2m) is not fully complementary to the toehold region. The equilibrium is consequently shifted to the state in which the primer duplex does not bind the spurious target.

Explained another way, in some instances, the free energy of the complement strand bound to the protector strand is $\Delta G_{3:3}° + \Delta G_{1:1}°$ (ignoring contribution from the optional hairpin region and other considerations), which balances the free energy of the complement strand bound to specific target, $\Delta G_{2:2}° + \Delta G_{1:1}°$. In this example, this is because the balance region (3) of the primer duplex has been designed to have a concentration-adjusted standard free energy equal to (or approximately equal to) that of target region (2). When the primer duplex interacts with a spurious target having a single-nucleotide (base) change in target region (2m), the system's free energy $\Delta G_{2m:2}° + \Delta G_{1:1}°$ is less negative than that of the primer duplex, and therefore disfavored in equilibrium.

As used herein, the term "approximately equal to" in reference to standard free energy means that the first referenced free energy is within 10% of the second referenced free energy. In some embodiments, a first free energy that is approximately equal to a second free energy is within about +3 kcal/mol to about −3 kcal/mol of the second free energy. It is to be understood that the differences between the first and second true energies may be less than or about 1 kcal/mol, less than or about 2 kcal/mol, less than or about 3 kcal/mol, less than or about 3.5 kcal/mol, or more, in some embodiments.

Although FIG. 3B illustrates a single nucleotide change corresponding to region (2)/(2m) of a target nucleic acid molecule, the present primer duplexes can also discriminate between a specific target and a spurious target having a nucleotide change in region (1). When the spurious target has a single-base change in target region 1, then the primer duplex's standard free energy after binding becomes $\Delta G_{2:2}° + \Delta G_{1m:1}°$, where $\Delta G_{1m:1}°$ is the standard free energy of the mismatched target region (1) binding to the primer duplex's complement region (1). Because of the single-base change, the primer duplex's free energy is less negative than $\Delta G_{3:3}° + \Delta G_{1:1}°$ (free energy of complement primer bound to protector), so equilibrium is shifted to the state in which the primer duplex does not bind the spurious target region. Standard free energies can be calculated theoretically based on the knowledge in the art and the teachings provided herein.

Complement and Protector Strands, Regions or Domains

The complement domains of the nucleic acid probe systems described herein each include a plurality of regions, including a toehold region and one or more complement target regions. Both the toehold region and the one or more complement target regions have nucleic acid sequences that are complementary to nucleic acid sequences of the target nucleic acid. The toehold region and the complement target region are therefore able to base-pair with and therefore form a complex with a sequence of a target nucleic acid when the nucleic acid probe system is contacted with a target nucleic acid under appropriate hybridization conditions. The complement domains may also include one or more complement balance regions. The one or more complement balance regions are rationally designed. Thus, the sequences of the one or more complement balance regions are not designed to be complementary to a target nucleic acid sequence.

A toehold region is complementary to (and thus hybridizes to) a sequence in the target nucleic acid molecule; however, a toehold region does not hybridize to a protector strand. Thus, when the complement strand is hybridized to the target nucleic acid molecule, the toehold region is also hybridized to the target nucleic acid molecule, but when the complement strand is hybridized to the protector strand, the toehold region remains single-stranded. A toehold region may be positioned at the 3' end or the 5' end of the complement strand (e.g., is an extension of the 3' end or 5' end of the complement strand).

In certain embodiments, a toehold region is about 4 nucleotides to about 20 nucleotides in length, about 4 nucleotides to about 15 nucleotides in length, or about 4 nucleotides to about 10 nucleotides in length. In some embodiments, a toehold region is 4, 5, 6, 7, 8, 9, 10, 11, 12, 13, 14, 15, 16, 17, 18, 19, or 20 nucleotides in length. In some embodiments, the toehold region is greater than 20 nucleotides in length, including for example less than or about 25, 30, 35, 40, 45, 50, 55, 60, 65, 70, 75, 80, 85, 90, 95, 100 or more nucleotides.

The complement branch migration region is complementary to a sequence in the target nucleic acid molecule and to the protector branch migration region. Thus, when the complement strand hybridizes to a target nucleic acid molecule, the complement branch migration region hybridizes to the target nucleic acid. When the complement strand hybridizes to its protector strand, the complement branch migration region hybridizes to the protector branch migration region.

In certain embodiments, a branch migration region is no more than 200, 100, 75, 50, 40, 30, 25 or 20 nucleotides in length. In some embodiments, a branch migration region is about 10 nucleotides to about 200 nucleotides in length. In certain embodiments, a branch migration region is about 10 nucleotides to about 150 nucleotides, about 10 nucleotides to about 100 nucleotides, or about 10 nucleotides to about 50 nucleotides in length. In particular embodiments, a branch migration region is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleotides in length. In particular embodiments, a branch migration region may be more than 200 nucleotides in length, depending on the target nucleic acid molecule of interest.

The balance regions of a complement strand and a protector strand are complementary to each other (i.e., form a double-stranded nucleic acid) but are non-complementary to the target of interest (i.e., neither forms a double-stranded nucleic acid with the target). Thus, when a complement strand hybridizes to a target nucleic acid molecule, the complement balance region does not hybridize to the target nucleic acid molecule. When the complement strand hybridizes to its protector strand, the complement balance region hybridizes to the protector balance region.

The design of the balance region is dependent on the design of the toehold region. In some embodiments, the balance region is designed such that the thermodynamic profile of the balance region is comparable to that of the toehold region. In some embodiments, the thermodynamic profile is based on a theoretic model, using for example, Mfold software available at the bioinfo website of RPI. The number and/or nature of nucleotides within a balance region is comparable to that of the toehold region. For example, if a toehold region is comprised of 40% A and T nucleotides and 60% G and C nucleotides, then the balance region should also be comprised of 40% A and T nucleotides and 60% G and C nucleotides. In embodiments, the balance region is designed such that no more than three consecutive nucleotides are complementary to a sequence on the target nucleic acid to avoid binding of the balance region to the target nucleic acid.

In some embodiments, the length of a balance region is short enough so that the complement and protector spontaneously dissociate from each other. In some embodiments, a balance region is about 4 nucleotides to about 20 nucleotides in length, about 4 nucleotides to about 15 nucleotides in length, or about 4 nucleotides to about 10 nucleotides in length. In some embodiments, a balance region is 4, 5, 6, 7, 8, 9, 10, 11, 12, 13, 14, 15, 16, 17, 18, 19, or 20 nucleotides in length. In some embodiments, a balance region is greater than 20 nucleotides, including for example less than about 25, 30, 35, 40, 45, 50, 55, 60, 65, 70, 75, 80, 85, 90, 95, 100 or more nucleotides. In some embodiments, the number of consecutive nucleotides that are complementary to a nucleotide sequence within the target nucleic acid may be greater than three provided that the balance region does not bind to the target nucleic acid.

In some embodiments, for example those where the primer duplex contains two separate nucleic acid strands, the design of a balance region does not depend on the concentration of the primer duplex or the temperature at which the primer duplex is formed/used. In some embodiments, a balance region is designed such that the standard free energy for the reaction in which the protector strand is displaced from the complement strand by the target nucleic acid molecule is close to zero kcal/mol. As used herein, "close to zero" means the standard free energy for the reaction is within 3.5 kcal/mol from 0 kcal/mol. In certain embodiments, the standard free energy of this displacement reaction is within 3.5, 3.0, 2.5, 2.0, 0.9, 0.8, 0.7, 0.6, 0.5, 0.4, 0.3, 0.2, or 0.1 kcal/mol of zero kcal/mol.

In other embodiments, for example those where the primer duplexes is formed by a single nucleic acid molecule (e.g., a hairpin region separating the complement strand (or region or domain) and the protector strand (or region or domain)), the design of a balance region will be dependent on the primer duplex concentration as well as reaction temperature. In such embodiments, a balance region is designed so that the standard free energy for the reaction in which the protector strand is displaced from the complement strand by the target nucleic acid plus RT ln(c) is close to zero kcal/mol, where R is the universal gas constant (0.0019858775(34) kcal/mol·K), T is the temperature at which the primer duplex is used, and c is the concentration at which primer duplex is used. In some embodiments, the temperature at which the primer duplexes are used is about 273 K (0° C.), 277 K, 283 K, 288 K, 293K, 298 K, 303 K, 308 K, 313 K, 318 K, 323 K, 328 K, 333 K, 338 K, 343 K, 348 K, 353 K, 358 K or 363 K (90° C.). In some embodiments the concentration (c) at which the primer duplexes are used is about 1 nM, 2 nM, 3 nM, 4 nM, 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 125 nM, 150 nM, 175 nM, 200 nM, 225 nM, 250 nM, 300 nM, 350 nM, 400 nM, 450 nM, 500 nM, 600 nM, 700 nM, 800 nM, 900 nM or 1 µM. In certain embodiments, the standard free energy of this displacement reaction plus RT ln(c) is within 3.5, 3.0, 2.5, 2.0, 0.9, 0.8, 0.7, 0.6, 0.5, 0.4, 0.3, 0.2, or 0.1 kcal/mol of zero kcal/mol.

In some embodiments, a primer duplex may include one or more hairpin regions that connect the complement strand to the protector strand. In certain embodiments, the hairpin region of a primer duplex can be of any length. In some embodiments, the hairpin region is more than 30, 25, 20, 19, 18, 17, 16, 15, 14, 13, 12, 11, 10, 9, 8, 7, 6, 5, 4 or 3 nucleotides in length. In some embodiments, the sequence of the hairpin is not complementary to a sequence of the target nucleic acid molecule.

In certain embodiments, the hairpin region has a poly-mononucleotide sequence, such as a poly-adenosine sequence, poly-deoxyadenosine sequence, a poly-5'-methyluridine sequence, a poly-thymidine sequence, a poly-guanosine sequence, a poly-deoxyguanosine sequence, a poly-cytidine sequence, a poly-deoxycytidine sequence, a poly-uridine sequence or a poly-deoxyuridine sequence.

The primer duplex described herein may be one of at least two orientations. For example, in one orientation, the toehold region is located at the 5' end, immediately adjacent to the complement branch migration region (i.e., no intervening nucleotides between the two regions), and the complement balance region is located at the 3' end, immediately adjacent to the complement branch migration region. In this orientation, the protector balance region is at the 5' end of the protector strand, immediately adjacent to the protector branch migration region (FIG. 1A). In another orientation, the toehold region is located at the 3' end, immediately adjacent to the complement branch migration region, and the complement balance region is located at the 5' end, immediately adjacent to the complement branch migration region. In this orientation, the protector balance region is at the 3' end of the protector strand, immediately adjacent to the protector branch migration region (FIG. 1B).

Regardless of orientation, the sequence of the complement balance region is such that such that:

$$|\Delta G_1° - \Delta G_2° - \Delta G_3°| \leq \Delta G_R°,$$

where:
- $\Delta G_1°$ is the standard free energy of hybridization of the protector balance region to the complement balance region;
- $\Delta G_2°$ is the standard free energy of hybridization of the protector balance region to the sequence immediately adjacent in the first direction to the target nucleic acid sequence, if any;
- $\Delta G_3°$ is the standard free energy of hybridization of the toehold region to the second target nucleic acid sequence; and
- $\Delta G_R°$ is 3.5 kcal/mol.

In some embodiments, a primer duplex comprises a complement strand longer than the protector, the difference in length being dependent on the length of the toehold region of the complement strand. The lengths of the primers are designed such that hybridization of the complement to the target of interest has a standard free energy ($\Delta G°$) close to zero. Release of the protector strand (from the primer duplex) ensures that this hybridization reaction is entropically neutral and robust to concentration. As a result, in some embodiments, this reaction at room temperature (e.g., about 25° C. or about 298 K) parallels the specificity of hybridization achieved at near melting temperature across many conditions.

As intended herein, a $\Delta G°$ (change in standard free energy) "close to zero" refers to an absolute value (amount) less than or about 1 kcal/mol, less than or about 2 kcal/mol, less than or about 3 kcal/mol, or less than or about 3.5 kcal/mol. In some embodiments, the standard free energy of a balance region or toehold region is >−1 kcal/mol to <1 kcal/mol >−3 kcal/mol to <3 kcal/mol or >−3.5 kcal/mol to <3.5 kcal/mol.

The primer duplexes may be prepared at a ratio of protector strand to complement strand of about 2:1 to about 5:1. In some embodiments, the ratio of protector strand to complement strand is about 2:1, about 3:1, about 4:1, or about 5:1. In some embodiments, the ratio of protector strand to complement strand is 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.2:1, 4.3:1, 4.4:1, 4.5:1, 4.6:1, 4.7:1, 4.8:1, 4.9:1, or 5:1. The primer duplexes may also be used together with excess protector strand in any of the assays or reactions described herein. The protector strand may be in about equal to or more than 2-, 5-, 10-, 20-, 50-, 100-, or 500-fold molar excess relative to the primer.

Hairpin Primer Duplex Systems (e.g., Single-Stranded Systems)

In certain embodiments, a primer duplex includes a single nucleic acid that comprises a complement region or domain, a hairpin region, and a protector region or domain. In some embodiments, the complement domain hybridizes to the protector domain, forming a primer duplex having in intervening hairpin-loop region. Like other primer systems disclosed here, such hairpin primer systems are designed to specifically hybridize to a target nucleic acid molecule. Herein, a "hairpin primer duplex system" or a "hairpin system" includes a complement balance region, a complement branch migration region, a toehold region, a protector balance region, and a protector branch migration region. As described above, a complement balance region is complementary to a protector balance region; a complement branch migration region is complementary to a protector branch migration region and a target nucleic acid region; and a toehold region is complementary to a target nucleic acid region. A protector branch migration region corresponds to a target nucleic acid region and is complementary to a complement branch migration region. Because the hairpin primer duplex systems described herein are formed by a single nucleic acid molecule, the design of the complement balance region will be dependent on the temperature and concentration at which the primer system is to be used, as described herein. It is to be understood that though the sequence of the target nucleic acid molecule may be used to describe the characteristics of the primer systems, in some embodiments, the target nucleic acid itself may or may not be a component of the primer system (e.g., two-stranded or single-stranded systems).

For primer duplexes having a hairpin region, the standard free energy of the confinement of the hairpin region may be considered when determining the standard free energy for the reaction in which the protector strand is displaced from the complement strand by the target nucleic acid. Approximate values for the standard free energy of hairpin confinement for hairpins of various sizes are provided in Table 1 (from SantaLucia and Hicks, *Annu. Rev. Biophys. Biomol. Struct.*, 33:414-440, (2004)).

| Hairpin Size | $\Delta G°$ of Hairpin Confinement |
|---|---|
| 3 nt | 3.5 kcal/mol |
| 4 nt | 3.5 kcal/mol |
| 5 nt | 3.3 kcal/mol |
| 6 nt | 4.0 kcal/mol |
| 7 nt | 4.2 kcal/mol |
| 8 nt | 4.3 kcal/mol |
| 9 nt | 4.5 kcal/mol |
| 10 nt | 4.6 kcal/mol |
| 12 nt | 5.0 kcal/mol |
| 14 nt | 5.1 kcal/mol |
| 16 nt | 5.3 kcal/mol |
| 18 nt | 5.5 kcal/mol |
| 20 nt | 5.7 kcal/mol |
| 25 nt | 6.1 kcal/mol |
| 30 nt | 6.3 kcal/mol |

The standard free energy of the confinement of the hairpin regions having lengths not provided in Table 1 (e.g., a length of n) can be estimated using the following equation:

$$\Delta G° \text{ (loop-}n) = \Delta G° \text{ (loop-}x) + 2.44 RT \ln(n/x)$$

where $\Delta G°$ (loop−n) is the unknown standard free energy of the confinement of a hairpin region of n nucleotides in length, $\Delta G°$ (loop−x) is the known standard free energy of the confinement of a hairpin region of n nucleotides in length (e.g., as provided in Table 1), R is the ideal gas constant, and T is the temperature at which the primer duplex is to be used. Additional information on the calculation of standard free energies of hairpin region confinement is provided in SantaLucia and Hicks, id., which is hereby incorporated by reference in its entirety.

The hairpin primer duplex systems described herein may be one of at least two orientations. For example, in one orientation shown in FIG. 2A, the toehold region is located at the 5' end of the nucleic acid molecule. The 5' end of the complement branch migration region is immediately adjacent to the 3' end of the toehold region; the 5' end of the complement balance region is immediately adjacent to the 3' end of the complement branch migration region; the 5' end of the hairpin region is immediately adjacent to the 3' end of the complement balance region; the 5' end of the protector balance region is immediately adjacent to the 3' end of the hairpin region; and the 5' end of the protector branch migration region is immediately adjacent to the 3' end of the protector balance region. In this orientation, when the nucleic acid molecule is subjected to conditions that permit annealing, the hairpin region forms a loop that extends from the complement balance region and the protector balance region. In another orientation shown in FIG. 2B, the toehold region is located at the 3' end of the nucleic acid molecule. The 3' end of the complement branch migration region is immediately adjacent to the 5' end of the toehold region; the 3' end of the complement balance region is immediately adjacent to the 5' end of the complement branch migration region; the 3' end of the hairpin region is immediately adjacent to the 5' end of the complement balance region; the 3' end of the protector balance region is immediately adjacent to the 5' end of the hairpin region; and the 3' end of the protector branch migration region is immediately adjacent to the 5' end of the protector balance region.

Regardless of orientation, the complement balance region of the hairpin primer duplex system has a sequence such that:

$$|\Delta G_1^\circ - \Delta G_2^\circ - \Delta G_3^\circ + \Delta G_4^\circ + RT\ln(c)| \leq \Delta G_R^\circ,$$

where:
- $\Delta G_1^\circ$ is the standard free energy of hybridization of the protector balance region to the complement balance region;
- $\Delta G_2^\circ$ is the standard free energy of hybridization of the protector balance region to the sequence immediately adjacent in the first direction to the target nucleic acid sequence, if any; and
- $\Delta G_3^\circ$ is the standard free energy of hybridization of the toehold region to the second target nucleic acid sequence;
- $\Delta G_4^\circ$ is the standard free energy of confinement of the hairpin region;
- R is the ideal gas constant;
- T is the temperature at which the primer system is to be used;
- c is the concentration at which the primer system is to be used; and
- $\Delta G_R^\circ$ is 3.5 kcal/mol.

Other Primer Systems

Additional primer systems are depicted in FIGS. 4-7. Each of these primer systems include a complement domain and two protector domains. The complement domain has a single toehold region that is flanked by two complement branch migration regions and two complement balance regions. Each of the protector domains include a protector branch migration region that has a sequence complementary to the sequence of one of the complement branch migration regions, and a protector balance region that has a sequence that is complementary to the sequence of one of the complement balance regions. The difference between the primer systems of FIGS. 4-7 is in the number and location of the hairpin regions, which in turn affects the design of the complement balance regions. Like the other primer systems disclosed here, these primer systems are designed to specifically hybridize to a target nucleic acid. Though the sequence of the target nucleic acid is used to describe the characteristics of a primer system, in some embodiments, the target nucleic acid is not a component of a primer system.

Figure 4:
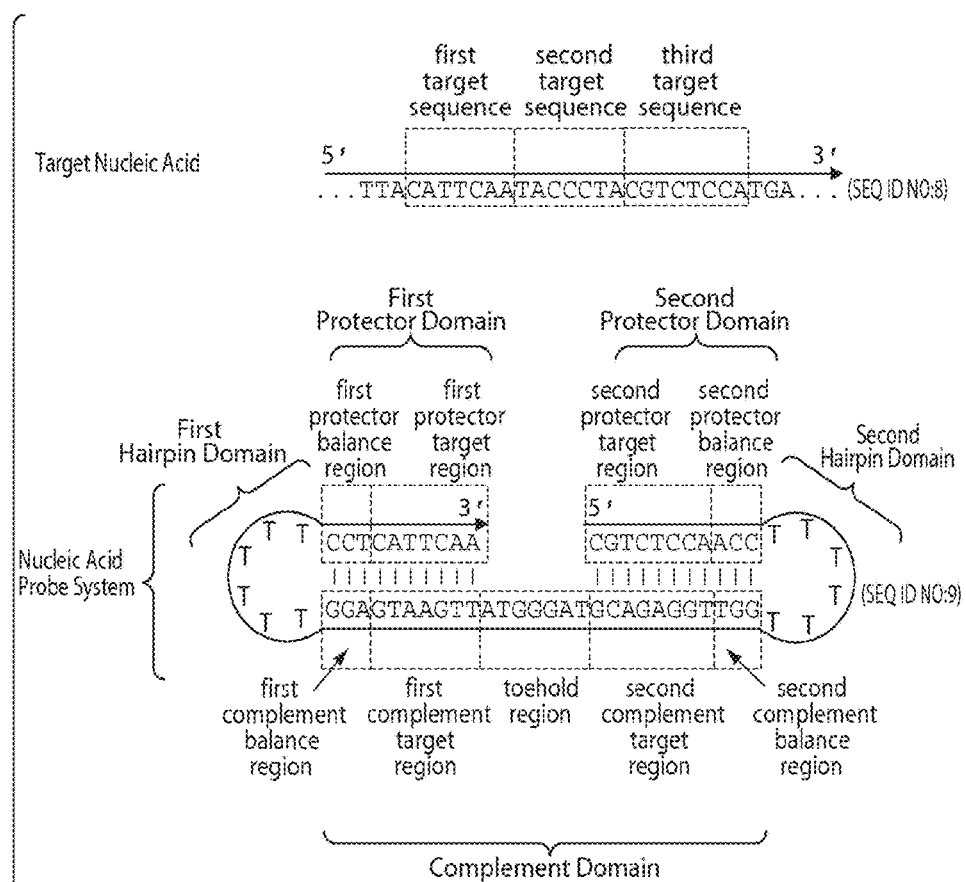

As depicted in FIG. 4, a primer system may have, in 3' to 5' order, a first protector domain, a first hairpin region, a complement domain, a second hairpin region and a second protector domain.

In such embodiments, the first protector domain includes a first protector branch migration region and a first protector balance region. The first protector branch migration region has a sequence that corresponds to a first target nucleic acid sequence. The first protector balance region is immediately 5' to the first protector branch migration region and has a sequence that does not correspond to sequence immediately 5' to the first target nucleic acid sequence, if any, on the target nucleic acid.

In this embodiment, the first hairpin region is immediately 5' to the first protector balance region.

The complement domain of such target nucleic acids comprises a first complement balance region, a first complement branch migration region, a toehold region, a second complement branch migration region and a second complement balance region. The first complement balance region is immediately 5' to the first hairpin region and has a sequence complementary to the sequence of the first protector balance region. The first complement branch migration region is immediately 5' to the first complement balance region and has a sequence complementary to a first protector branch migration region. The toehold region is immediately 5' to the first complement branch migration region and has a sequence that is complementary to a second target nucleic acid sequence that is immediately 3' to the first target nucleic acid sequence on the target nucleic acid. The second complement branch migration region is immediately 5' to the toehold region and has a sequence complementary to a third target nucleic acid sequence that is immediately 3' to the second target nucleic acid sequence on the target nucleic acid. The second complement balance region is immediately 5' to the second complement branch migration region and has a sequence that is not complementary to sequence immediately 3' to the third target nucleic acid sequence, if any, on the target nucleic acid.

In such embodiments, the second hairpin region is immediately 5' to the second complement balance region.

In this embodiment the second protector domain includes a second protector balance region and a second protector branch migration region. The second protector balance region is immediately 5' to the second hairpin region and has a sequence complementary to the second complement balance region. The second protector branch migration region is immediately 5' to the second protector balance region and has a sequence complementary to the second complement branch migration region.

According to this embodiment, the first complement balance region and the second complement balance region have sequences such that:

$$\Delta G_1^\circ - \Delta G_2^\circ + \Delta G_3^\circ - \Delta G_4^\circ - \Delta G_5^\circ + \Delta G_6^\circ + \Delta G_7^\circ + RT\ln(c)| \leq \Delta G_R^\circ,$$

where:
- $\Delta G_1^\circ$ is the standard free energy of hybridization of the first protector balance region to the first complement balance region;
- $\Delta G_2^\circ$ is the standard free energy of hybridization of the first complement balance region to the sequence immediately 5' to the first target nucleic acid sequence, if any;
- $\Delta G_3^\circ$ is the standard free energy of hybridization of the second protector balance region to the second complement balance region;

$\Delta G_4^\circ$ is the standard free energy of hybridization of the second complement balance region to the sequence immediately 3' to the third target nucleic acid sequence, if any;

$\Delta G_5^\circ$ is the standard free energy of hybridization of the toehold region to the second target nucleic acid sequence;

$\Delta G_6^\circ$ is the standard free energy of confinement of the first hairpin region;

$\Delta G_7^\circ$ is the standard free energy of confinement of the second hairpin region;

R is the ideal gas constant;

T is the temperature at which the primer system is to be used; and c is the concentration at which the primer system is to be used; and $\Delta G_R^\circ$ is 3.5 kcal/mol.

Figure 5:
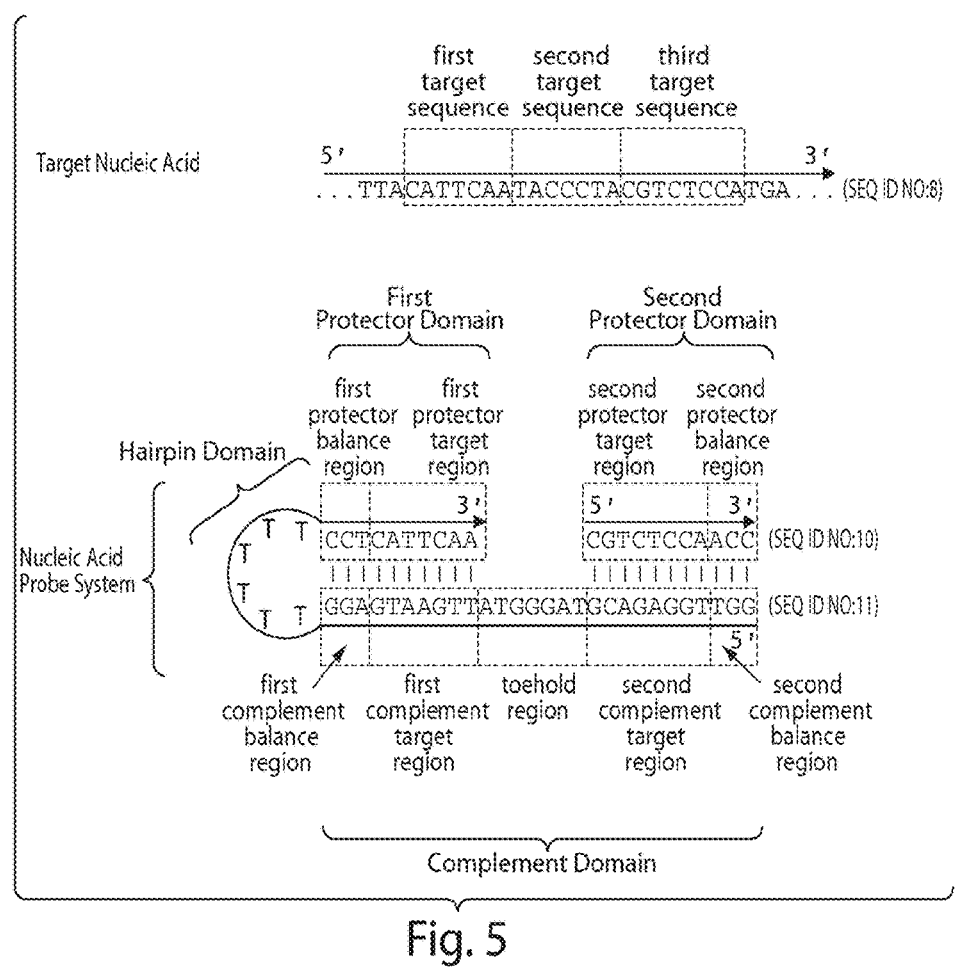

As depicted in FIG. 5, in certain embodiments, a primer system may have a hairpin primer and a protector, where the hairpin primer is a nucleic acid that includes a first protector domain, a first hairpin region, a complement domain and the protector is a nucleic acid that includes a second protector domain.

In such embodiments, the first protector domain includes a first protector branch migration region and a first protector balance region. The first protector branch migration region has a sequence that corresponds to a first target nucleic acid sequence. The first protector balance region is immediately 5' to the first protector branch migration region and has a sequence that does not correspond to sequence immediately 5' to the first target nucleic acid sequence, if any, on the target nucleic acid.

In this embodiment, the hairpin region is immediately 5' to the first protector balance region.

The complement domain of such target nucleic acids comprises a first complement balance region, a first complement branch migration region, a toehold region, a second complement branch migration region and a second complement balance region. The first complement balance region is immediately 5' to the hairpin region and has a sequence complementary to the sequence of the first protector balance region. The first complement branch migration region is immediately 5' to the first complement balance region and has a sequence complementary to a first protector branch migration region. The toehold region is immediately 5' to the first complement branch migration region and has a sequence that is complementary to a second target nucleic acid sequence that is immediately 3' to the first target nucleic acid sequence on the target nucleic acid. The second complement branch migration region is immediately 5' to the toehold region and has a sequence complementary to a third target nucleic acid sequence that is immediately 3' to the second target nucleic acid sequence on the target nucleic acid. The second complement balance region is immediately 5' to the second complement branch migration region and has a sequence that is not complementary to sequence immediately 3' to the third target nucleic acid sequence, if any, on the target nucleic acid.

In this embodiment, the second protector domain includes a second protector balance region and a second protector branch migration region. The second protector balance region has a sequence complementary to the second complement balance region. The second protector branch migration region is immediately 5' to the second protector balance region and has a sequence complementary to the second complement branch migration region.

According to this embodiment, the first complement balance region and the second complement balance region have sequences such that:

$$|\Delta G_1^\circ - \Delta G_2^\circ + \Delta G_3^\circ - \Delta G_4^\circ - \Delta G_5^\circ + \Delta G_6^\circ| \leq \Delta G_R^\circ,$$

where:

$\Delta G_1^\circ$ is the standard free energy of hybridization of the first protector balance region to the first complement balance region;

$\Delta G_2^\circ$ is the standard free energy of hybridization of the first complement balance region to the sequence immediately 5' to the first target nucleic acid sequence, if any;

$\Delta G_3^\circ$ is the standard free energy of hybridization of the second protector balance region to the second complement balance region;

$\Delta G_4^\circ$ is the standard free energy of hybridization of the second complement balance region to the sequence immediately 3' to the third target nucleic acid sequence, if any;

$\Delta G_5^\circ$ is the standard free energy of hybridization of the toehold region to the second target nucleic acid sequence;

$\Delta G_6^\circ$ is the standard free energy of confinement of the hairpin region; and $\Delta G_R^\circ$ is 3.5 kcal/mol.

Figure 6:
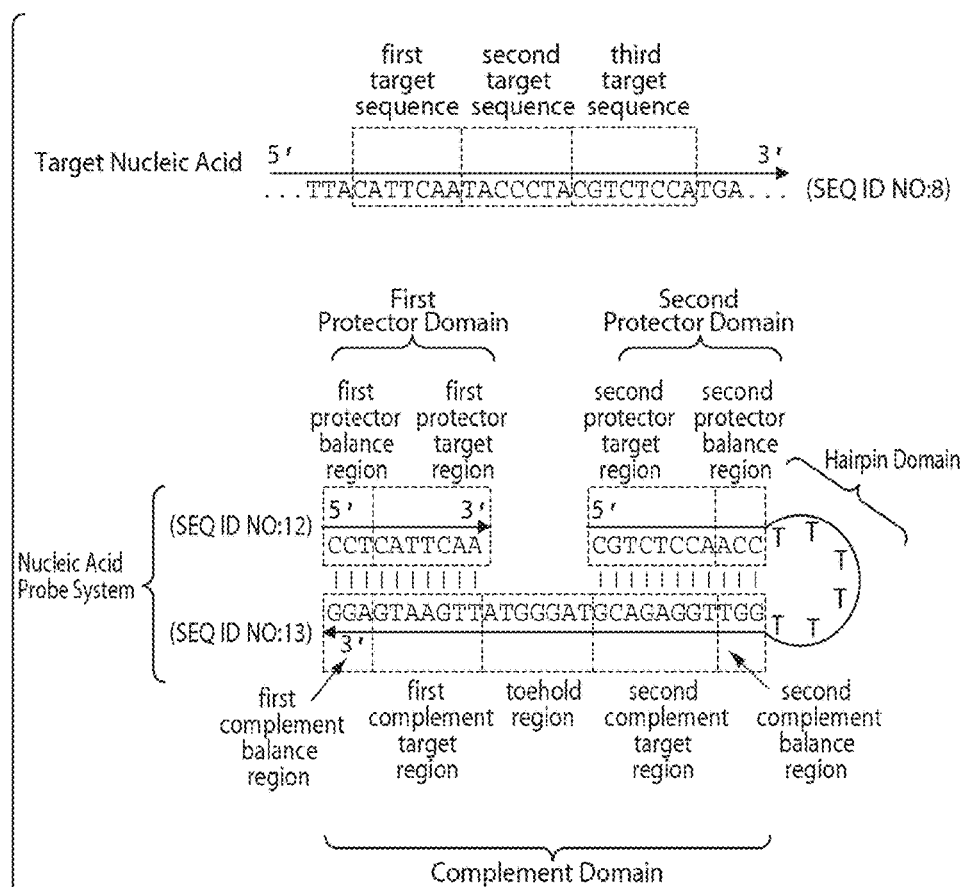

As depicted in FIG. 6, in certain embodiments a primer system may have a protector and a hairpin primer, where the protector is a nucleic acid that includes a first protector domain and the hairpin primer is a nucleic acid that includes a complement domain, hairpin region and a second protector domain.

In such embodiments, the first protector domain includes a first protector branch migration region and a first protector balance region. The first protector branch migration region has a sequence that corresponds to a first target nucleic acid sequence. The first protector balance region is immediately 5' to the first protector branch migration region and has a sequence that does not correspond to sequence immediately 5' to the first target nucleic acid sequence, if any, on the target nucleic acid.

The complement domain of such target nucleic acids comprises a first complement balance region, a first complement branch migration region, a toehold region, a second complement branch migration region and a second complement balance region. The first complement balance region has a sequence complementary to the sequence of the first protector balance region. The first complement branch migration region is immediately 5' to the first complement balance region and has a sequence complementary to a first protector branch migration region. The toehold region is immediately 5' to the first complement branch migration region and has a sequence that is complementary to a second target nucleic acid sequence that is immediately 3' to the first target nucleic acid sequence on the target nucleic acid. The second complement branch migration region is immediately 5' to the toehold region and has a sequence complementary to a third target nucleic acid sequence that is immediately 3' to the second target nucleic acid sequence on the target nucleic acid. The second complement balance region is immediately 5' to the second complement branch migration region and has a sequence that is not complementary to sequence immediately 3' to the third target nucleic acid sequence, if any, on the target nucleic acid.

According to such embodiments, the hairpin region is immediately 5' to the second complement balance region.

In this embodiment the second protector domain includes a second protector balance region and a second protector branch migration region. The second protector balance region is immediately 5' to the hairpin region and has a sequence complementary to the second complement balance region. The second protector branch migration region is immediately 5' to the second protector balance region and has a sequence complementary to the second complement branch migration region.

According to this embodiment, the first complement balance region and the second complement balance region have sequences such that:

$$|\Delta G_1° - \Delta G_2° + \Delta G_3° - \Delta G_4° - \Delta G_5° + \Delta G_6°| \le \Delta G_R°,$$

where:
- $\Delta G_1°$ is the standard free energy of hybridization of the first protector balance region to the first complement balance region;
- $\Delta G_2°$ is the standard free energy of hybridization of the first complement balance region to the sequence immediately 5' to the first target nucleic acid sequence, if any;
- $\Delta G_3°$ is the standard free energy of hybridization of the second protector balance region to the second complement balance region;
- $\Delta G_4°$ is the standard free energy of hybridization of the second complement balance region to the sequence immediately 3' to the third target nucleic acid sequence, if any; and
- $\Delta G_5°$ is the standard free energy of hybridization of the toehold region to the second target nucleic acid sequence;
- $\Delta G_6°$ is the standard free energy of confinement of the hairpin region; and
- $\Delta G_R°$ is 3.5 kcal/mol.

Figure 7:
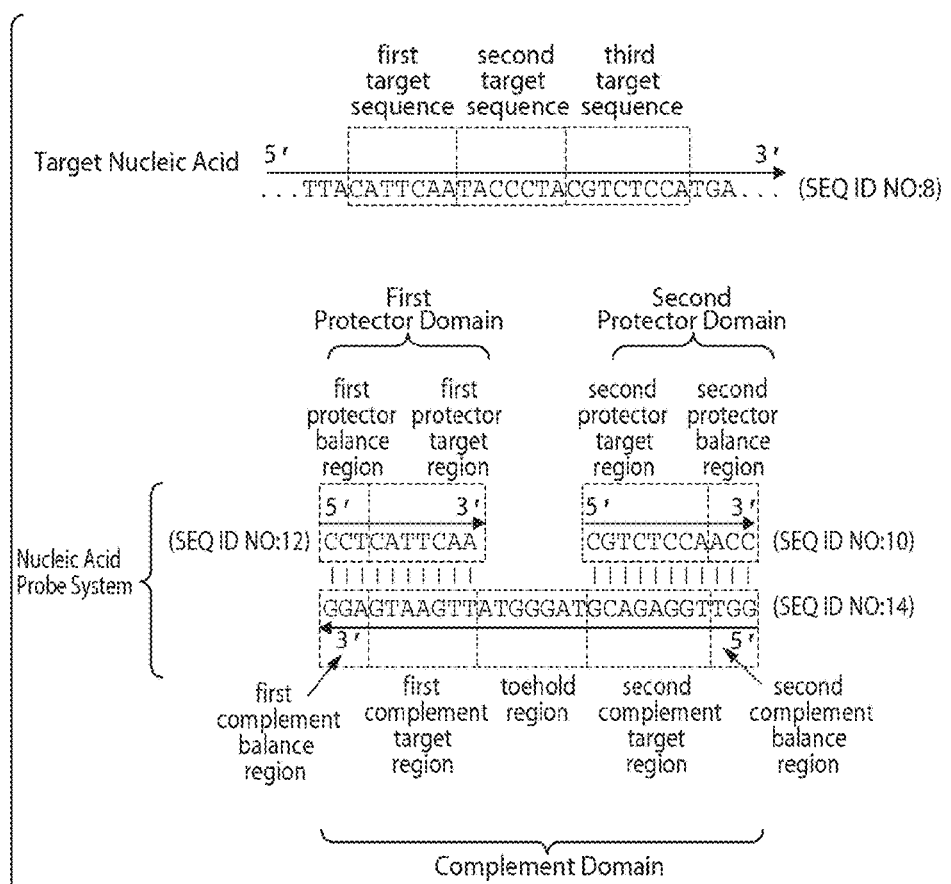

As depicted in FIG. 7, in certain embodiments a primer system may have a first protector, a complement primer and a second protector, where the first protector is a nucleic acid that includes a first protector domain, the complement primer is a nucleic acid that includes a complement domain, and the second protector is a nucleic acid that includes a second protector domain.

In such embodiments, the first protector domain includes a first protector branch migration region and a first protector balance region. The first protector branch migration region has a sequence that corresponds to a first target nucleic acid sequence. The first protector balance region is immediately 5' to the first protector branch migration region and has a sequence that does not correspond to sequence immediately 5' to the first target nucleic acid sequence, if any, on the target nucleic acid.

The complement domain of such target nucleic acids comprises a first complement balance region, a first complement branch migration region, a toehold region, a second complement branch migration region and a second complement balance region. The first complement balance region has a sequence complementary to the sequence of the first protector balance region. The first complement branch migration region is immediately 5' to the first complement balance region and has a sequence complementary to a first protector branch migration region. The toehold region is immediately 5' to the first complement branch migration region and has a sequence that is complementary to a second target nucleic acid sequence that is immediately 3' to the first target nucleic acid sequence on the target nucleic acid. The second complement branch migration region is immediately 5' to the toehold region and has a sequence complementary to a third target nucleic acid sequence that is immediately 3' to the second target nucleic acid sequence on the target nucleic acid. The second complement balance region is immediately 5' to the second complement branch migration region and has a sequence that is not complementary to sequence immediately 3' to the third target nucleic acid sequence, if any, on the target nucleic acid.

In this embodiment the second protector domain includes a second protector balance region and a second protector branch migration region. The second protector balance region has a sequence complementary to the second complement balance region. The second protector branch migration region is immediately 5' to the second protector balance region and has a sequence complementary to the second complement branch migration region.

According to this embodiment, the first complement balance region and the second complement balance region have sequences such that:

$$|\Delta G_1° - \Delta G_2° + \Delta G_3° - \Delta G_4° - \Delta G_5° - RT \ln(c)| \le \Delta G_R°,$$

where:
- $\Delta G_1°$ is the standard free energy of hybridization of the first protector balance region to the first complement balance region;
- $\Delta G_2°$ is the standard free energy of hybridization of the first complement balance region to the sequence immediately 5' to the first target nucleic acid sequence, if any;
- $\Delta G_3°$ is the standard free energy of hybridization of the second protector balance region to the second complement balance region;
- $\Delta G_4°$ is the standard free energy of hybridization of the second complement balance region to the sequence immediately 3' to the third target nucleic acid sequence, if any; and
- $\Delta G_5°$ is the standard free energy of hybridization of the toehold region to the second target nucleic acid sequence;
- R is the ideal gas constant;
- T is the temperature at which the primer system is to be used;
- c is the concentration at which the primer system is to be used; and
- $\Delta G_R°$ is 3.5 kcal/mol.

Primer Duplex Systems Lacking Balance Domains

In some embodiments, primer systems may lack balance domains. Such nucleic acids will hybridize with a target nucleic acid with fast kinetics if the target nucleic acid has a sequence complementary to the sequence of the toehold region of the primer system, but with slow kinetics if the target nucleic is mutated so that it does not contain a sequence complementary to the toehold region of the primer system. Such primer systems are therefore useful, for example, for locating difference and/or mutations in nucleic acid targets using kinetic discrimination.

Figure 8:
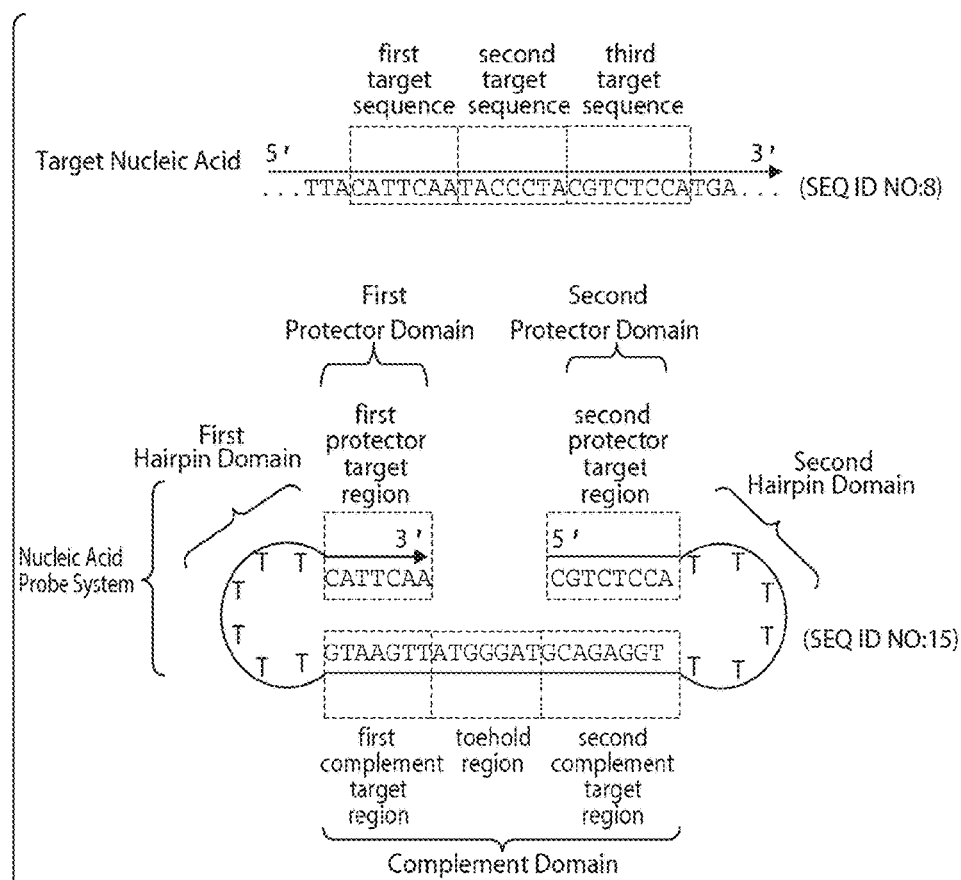

As depicted in FIG. 8, in certain embodiments a primer system may include a nucleic acid having, in 3' to 5' order, a first protector domain, a first hairpin region, a complement domain, a second hairpin region and a second protector domain. The first protector domain of such primer systems has a sequence that corresponds to a first target nucleic acid sequence. The first hairpin region is immediately 5' of the first protector domain. The complement domain has a first complement branch migration region, a toehold region and a second complement branch migration region. The first complement branch migration region is immediately 5' of the first hairpin region and has a sequence complementary to the branch migration sequence of the first protector domain. The toehold region is immediately 5' of the first complement branch migration region and has a sequence complementary to a second target nucleic acid sequence that is immediately 3' of the first target nucleic acid sequence on the target nucleic acid molecule. The second complement branch migration region is immediately 5' of the toehold region and has a sequence complementary to a third target nucleic acid sequence that is immediately 3' of the second nucleic acid sequence. The second hairpin region is immediately 5' of the second complement branch migration region. The second protector domain has a sequence that is complementary to the sequence of the second complement branch migration region.

Primer Modifications Generally

Each primer described herein may be comprised of DNA, RNA, or analogs thereof, and/or combinations thereof. In certain embodiments, a primer comprises one or more non-natural nucleotides. The incorporation of non-natural nucleotides in the primers can further augment the performance of the primer duplexes. In particular, the protector strand, while not intended to serve to initiate transcription, may happen to be complementary to other regions of the target or other background molecules, and may spuriously initiate replication/transcription. To prevent this, the use of a non-natural nucleotide or a dideoxy nucleotide at the 3' end of the second protector strand may serve to prevent unintended priming by that strand. Examples of non-natural nucleotides include, but are not limited to, iso-C, iso-G, deoxyuridine (see also Krueger et al. *Chem. Biol.* 16:242-48 (2009), the teachings which relating to non-natural nucleotides are incorporated by reference herein).

In some embodiments, for example, in a polymerase chain reaction (PCR) where a repeated primed enzymatic function is used, the extended complement strand can become a target for subsequent primer hybridization. To preserve the specificity of primer hybridization for subsequent rounds of amplification, a balance region of a primer cannot be replicated. Introducing a non-natural nucleotide at the interface between the branch migration and balance regions of the complement strand, for example, may prevent the balance region from being replicated.

In certain embodiments, the primers described herein serve as starting points for polymerase extensions. To facilitate analysis of amplified (nucleic acid) fragments, labeled primers can also be used in PCR reactions. Labeled primers are those that are coupled (or conjugated) to a detectable moiety. Examples include fluorescent dyes, radioactive labels, and identifiable metals, nucleic acid sequences, and proteins. When a reaction is carried out with fluorescently labeled primers, amplicons (nucleic acid products) with a fluorescent label may be generated.

The primers described herein can be synthesized by any method known in the art (see, e.g., Ogilvie et al. *J. Amer. Chem. Soc.* 99 (23): 7741-7743; Reese, C. B. *Tetrahedron* 34(21): 3143 (1978); Efimov et al. *Nucleic Acids Res.* 11(23): 8369-8387 (1983); Garegg et al. *Tetrahedron Lett.* 27(34): 4051 (1986); Beaucage et al. *Tetrahedron* 48(12): 2223 (1992); Efimov et al. *Nucleosides, Nucleotides & Nucleic Acids* 26 (8-9): 1087-93 (2007), incorporated herein by reference).

Target Nucleic Acid Molecules

A "target" can be a single-stranded (ss) or double-stranded (ss) nucleic acid. Target nucleic acids can be, for example, DNA, RNA, or the DNA product of RNA subjected to reverse transcription. In some embodiments, a target may be a mixture (chimera) of DNA and RNA. In other embodiments, a target comprises artificial nucleic acid analogs, for example, peptide nucleic acids (Nielsen et al. *Science* 254(5037): 1497-500 (1991)) or locked nucleic acids (Alexei et al. *Tetrahedron* 54(14): 3607-30 (1998)). In some embodiments, a target may be naturally occurring (e.g., genomic DNA) or it may be synthetic (e.g., from a genomic library). As used herein, a "naturally occurring" nucleic acid sequence is a sequence that is present in nucleic acid molecules of organisms or viruses that exist in nature in the absence of human intervention. In some embodiments, a target is genomic DNA, messenger RNA, ribosomal RNA, micro-RNA, pre-micro-RNA, pro-micro-RNA, viral DNA, viral RNA or piwi-RNA. In certain embodiments, a target nucleic acid is a nucleic acid that naturally occurs in an organism or virus. In some embodiments, a target nucleic is the nucleic acid of a pathogenic organism or virus. In certain embodiments the presence or absence of a target nucleic acid in a subject is indicative that the subject has a disease or disorder or is predisposed to acquire a disease or disorder. In certain embodiments the presence or absence of a target nucleic acid in a subject is indicative that the subject will respond well or poorly to a treatment, such as a drug, to treat a disease or disorder.

The terms "polynucleotide," "nucleic acid" and "nucleic acid molecule" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. The term "recombinant" polynucleotide means a polynucleotide of genomic, cDNA, semi-synthetic, or synthetic origin which either does not occur in nature or is linked to another polynucleotide in a non-natural arrangement. The term "isolated nucleic acid" refers to a polynucleotide of natural or synthetic origin or some combination thereof, which (1) is not associated with the cell in which the "isolated nucleic acid" is found in nature, and/or (2) is operably linked to a polynucleotide to which it is not linked in nature.

A nucleic acid may also encompass single- and double-stranded DNA and RNA, as well as any and all forms of alternative nucleic acid containing modified bases, sugars, and backbones. The term "nucleic acid" thus will be understood to include, but not be limited to, single- or double-stranded DNA or RNA (and forms thereof that can be partially single-stranded or partially double-stranded), cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties. "Analogous" forms of purines and pyrimidines are well known in the art, and include, but are not limited to aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N.sup.6-methyladenine, 7-methylguanine, 5-methylaminomethyluracil, 5-methoxyaminomethyl-2-thiouracil, beta-D-mannosylqueosine, 5-methoxyuracil, 2-methylthio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, and 2,6-diaminopurine. DNA backbone analogues provided herein include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs), methylphosphonate linkages or alternating methylphosphonate and phosphodiester linkages (Strauss-Soukup, 1997, Biochemistry 36:8692-8698), and benzylphosphonate linkages, as discussed in U.S. Pat. No. 6,664,057; see also OLIGONUCLEOTIDES AND ANALOGUES, A PRACTICAL APPROACH, edited by F. Eckstein, IRL Press at Oxford University Press (1991); Antisense Strategies, Annals of the New York Academy of Sciences, Volume 600, Eds. Baserga and Denhardt (NYAS 1992); Milligan, 1993, *J. Med. Chem.* 36:1923-1937; Antisense Research and Applications (1993, CRC Press). The nucleic acids herein can be extracted from cells or synthetically prepared according to any means known to those skilled in the art; for example, the nucleic acids can be chemically synthesized or transcribed or reverse transcribed from cDNA or mRNA, among other sources.

As used herein, two nucleic acids or nucleic acid regions "correspond" to one another if they are both complementary to the same nucleic acid sequence. Two nucleic acids or nucleic acid regions are "complementary" to one another if they base-pair with each other to form a double-stranded nucleic acid molecule.

A target nucleic acids utilized herein can be any nucleic acid, for example, human nucleic acids, bacterial nucleic acids, or viral nucleic acids. A target nucleic acid sample can be, for example, a nucleic acid sample from one or more cells, tissues, or bodily fluids. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one source or different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

In some embodiments, a target nucleic acids utilized herein comprise repetitive sequence, secondary structure, and/or a high G/C content.

In certain embodiments, a target nucleic acid molecule of interest is about 100 to about 1,000,000 nucleotides (nt) in length. In some embodiments, the target is about 100 to about 1000, about 1000 to about 10,000, about 10,000 to about 100,000, or about 100,000 to about 1,000,000 nucleotides in length. In some embodiments, the target is about 100, about 200, about 300, about 400, about 500, about 600, about 700, about 800, about 900, about 1,000, about 2,000, about 3,000, about 4,000, about 5,000, about 6,000, about 7,000, about 8,000, about 9000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, or about 1,000,000 nucleotides in length. It is to be understood that the target nucleic acid may be provided in the context of a longer nucleic acid (e.g., such as a coding sequence or gene within a chromosome or a chromosome fragment).

In certain embodiments, a target of interest is linear, while in other embodiments, a target is circular (e.g., plasmid DNA, mitochondrial DNA, or plastid DNA).

Combined Primer-Target Systems

In some embodiments, provided herein are primer-target systems. A primer-target system comprises one or more nucleic acid targets, a polymerase, and one or more primers (e.g., primer duplex and/or hairpin primer duplex). The term "primer" encompasses any one of the primers or primer systems described herein (e.g., single-stranded primers, double-stranded primer duplexes, and hairpin primer duplexes). In certain embodiments, the primer-target systems described herein comprise a plurality of different primers. In some embodiments, a primer-target system can comprise at least two primers, which can be used to identify and, for example amplify, a target nucleic acid molecule. A target nucleic acid molecule may be present amongst a plurality of non-target nucleic acid molecules, for example, as a single copy or in low copy number. Any one of the primer-target systems described herein may comprises conditions similar to those used in nucleic acid amplification or sequencing reactions (e.g., similar reagents, reaction temperature, etc.).

Methods of Use

The primer systems described herein are able to discriminate a specific target from spurious targets either through a thermodynamic mechanism or through a kinetic mechanism.

In distinguishing the target from spurious targets using a thermodynamic mechanism (described below), the strand displacement reaction is run to completion and the target is distinguished from the spurious targets based on differences in equilibrium binding affinity. To distinguish the target from spurious targets using a kinetic mechanism (described below), the strand displacement reaction is stopped before reaching equilibrium, and the differential rate in reaction completion is used to distinguish the targets from spurious targets.

Thermodynamic Separation

The general strategy for both the thermodynamic and the kinetic mechanism is to use toehold exchange strand displacement reactions. In general, toehold exchange involves extending a target's complement with an additional region that is not complementary to the target, and pre-hybridizing a protector strand to this extended complement strand and a large number of bases adjacent to the extended region, but not to a single-stranded toehold region.

Figure 9A:
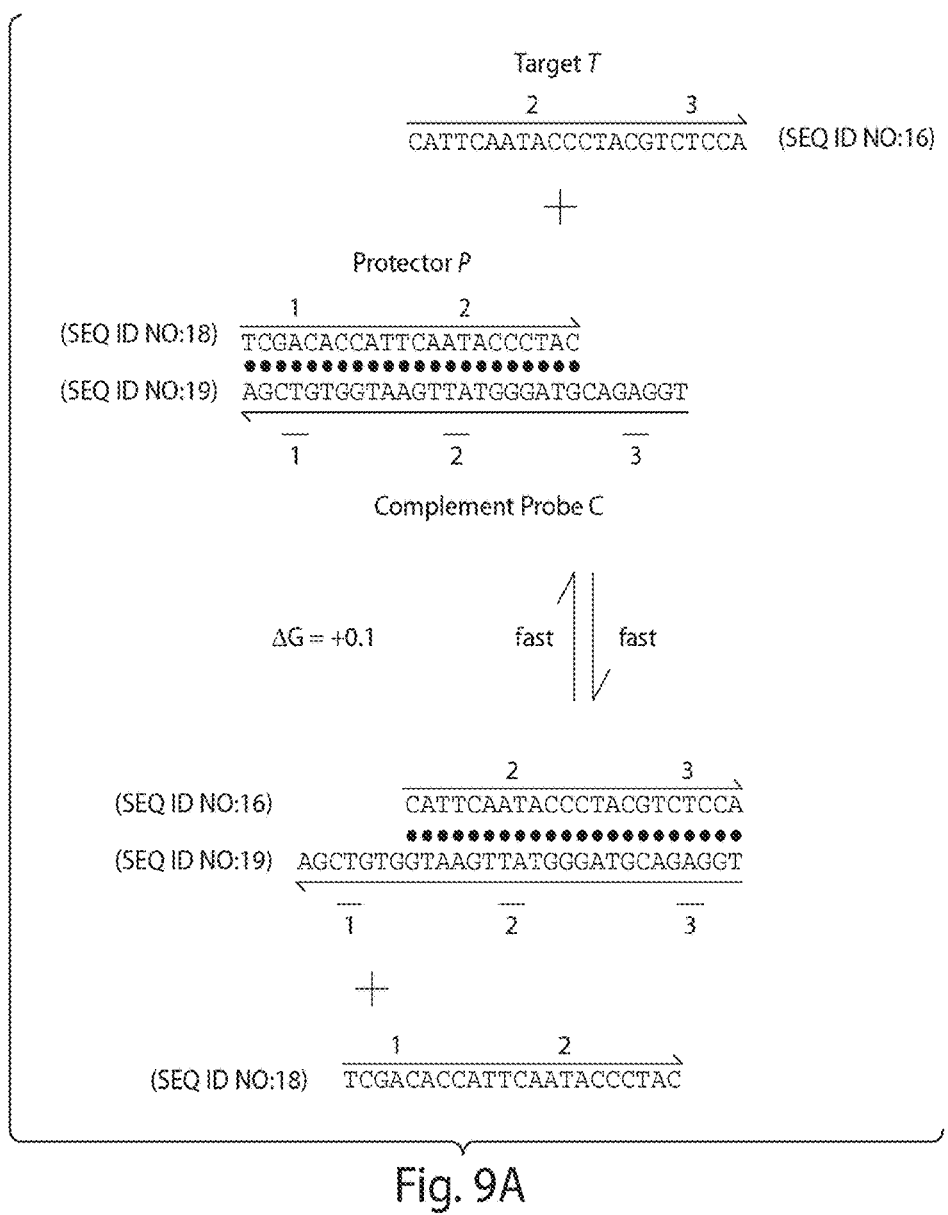
Figure 9B:
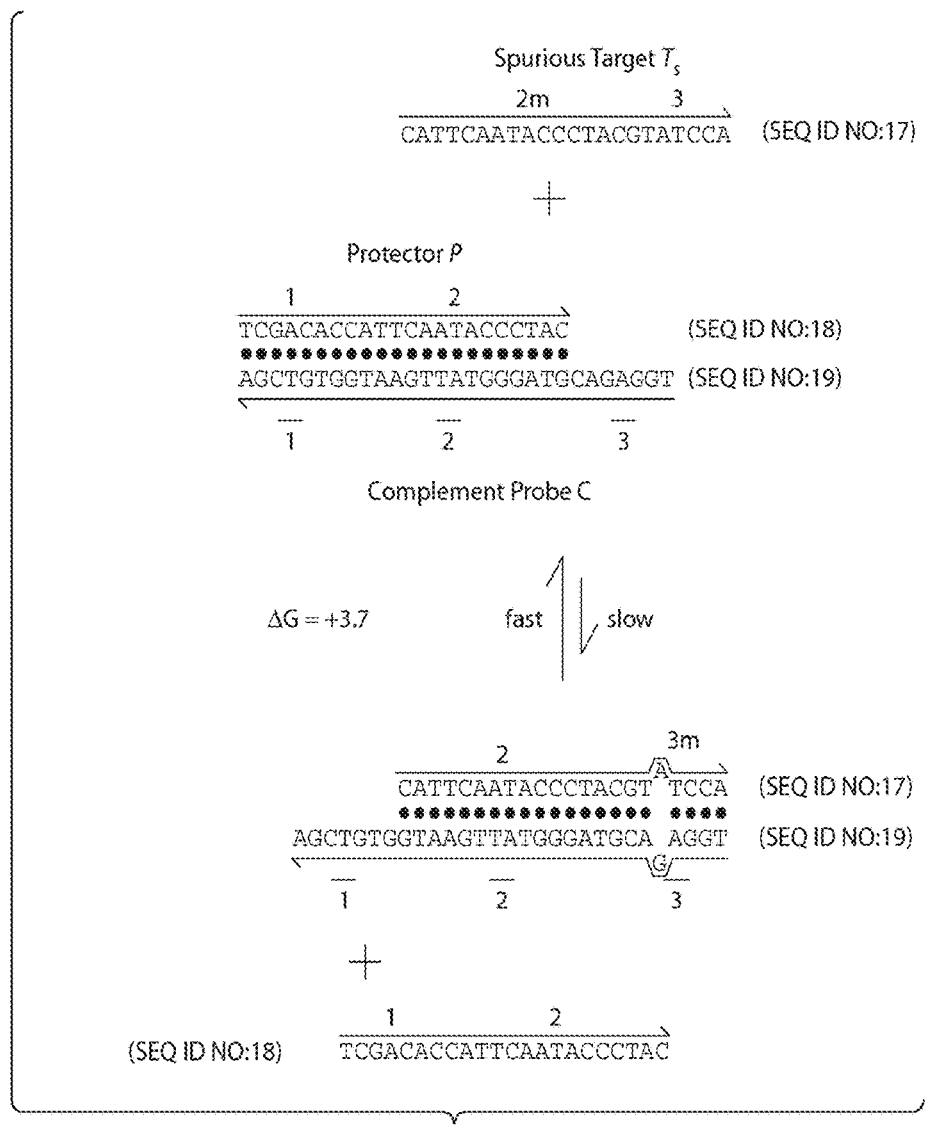

FIG. 9 depicts one implementation of toehold exchange. In this implementation, a two-stranded primer duplex system (as described above and depicted in FIG. 1A) is used to distinguish between a target nucleic acid and a spurious target. The complement branch migration region and the toehold region of the complement strand have sequences that correspond to a first target sequence and a second target sequence, respectively. A complement balance region was designed to be the same length and nucleotide base distribution as the toehold region. In this way, the standard free energy of the strand displacement reaction shown in FIG. 9A between the correct target and the protected complement is roughly $\Delta G° = 0$ kcal/mol.

The strand displacement reaction can be written as:

Target+Complement/Protector ⇌ Target/Complement+ Protector $\Delta G°$ relates to the equilibrium constant $K_{eq}$ by the following relation:

$$\Delta G° = RT \ln(K_{eq}).$$

For a reaction with $\Delta G° = 0$, the equilibrium constant ($K_{eq}$) is 1. The equilibrium constant also relates to the equilibrium; for this reaction, $K_{eq} = [TC][P]/[T][PC] = 1$. For an assay where [PC] and [P] and are in excess of [T], [TC]/[T]=1, meaning that exactly half of all target molecules are hybridized at equilibrium. In the example shown in FIG. 9A, $\Delta G° = +0.1$ kcal/mol, corresponding to a $K_{eq} = 0.85$, which means that 46% of the target molecules are hybridized at equilibrium.

The protector strand correspondingly changes the standard free energy of the strand displacement reaction with spurious targets. In the example shown in FIG. 9B, the spurious target differs from the correct target by a single base, which results in the strand displacement reaction with the same two-stranded nucleic acid primer system having a $\Delta G°$ of +3.7 kcal/mol, which corresponds to $K_{eq} = 1.9*10^{-3}$. At equilibrium, only 0.19% of the spurious target will be hybridized to the complement. Thus, the exemplary nucleic acid primer system depicted in FIG. 8 preferentially binds to its target versus a spurious target having only a single nucleotide mismatch by more than 200-fold.

Figure 10:
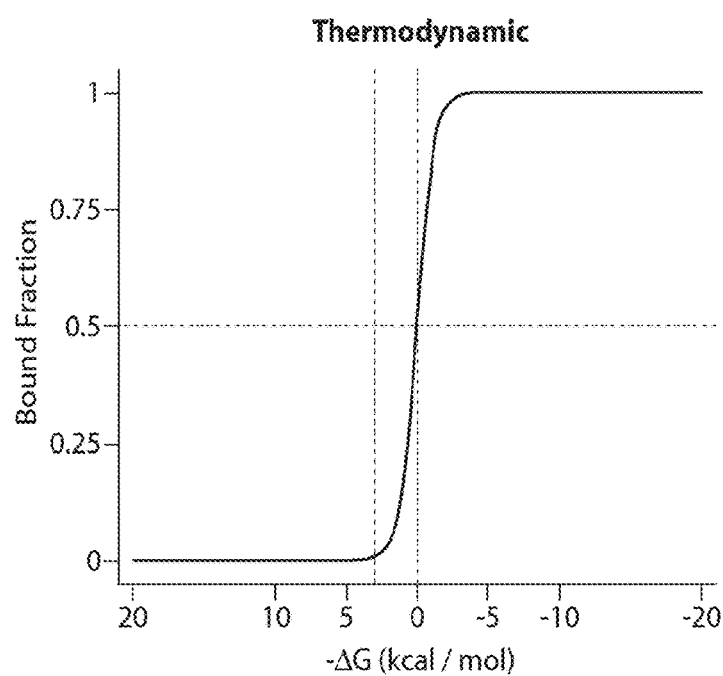
FIGS. 10, 11, 12A, 12B, 13, and 14 depict exemplary methods of using nucleic acid probe systems.

FIG. 10 is a plot of the equilibrium binding affinity as a function of the standard free energy of the reaction. When the standard free energy of the reaction is very negative (as in the case in a pure hybridization reaction), both the target and the spurious targets bind very strongly, and it is difficult to distinguish between the two, leading to false positives. On the other hand, when the standard free energy of the reaction is very positive, the primer binds to the target very weakly, leading to false negatives. Designing a primer duplex system to have a standard free energy of near zero results in an optimal discrimination between targets and spurious targets, thereby minimizing false positives and false negatives.

Kinetic Separation

Figure 11:
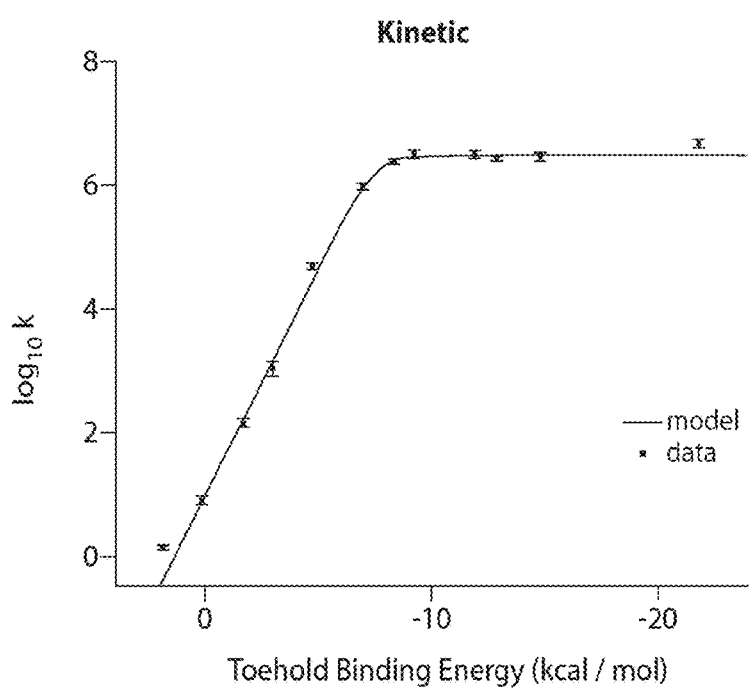

Kinetic separation relies on the differential kinetics of toehold exchange. The kinetics of the toehold exchange reaction depend on the binding strengths of the toeholds regions. Each kcal/mol of difference in toehold binding energy can affect kinetics by a factor of 5.4 (FIG. 11), so the +3.6 kcal/mol mismatch shown in FIG. 9B would yield a kinetic slowdown of 434.

Unlike in thermodynamic discrimination, kinetic discrimination occurs only when the mismatch is in the toehold region. Spurious targets differing from the correct target at a position complementary to the complement branch migration region are unlikely to yield significantly different reaction kinetics. As a consequence, methods that use the kinetic mechanism of distinguishing target from spurious target are useful in conjunction with thermodynamic separation as a means of pinpointing the locations of target/primer mismatches.

Significantly, primer duplex systems lacking complement balance regions, such as the primer systems depicted in FIG. 8, can be used in methods that exploit the kinetic mechanism to pinpoint the location of target/primer mismatches.

Microarrays

Nucleic acid microarrays are often used for high-throughput nucleic acid detection, but often are unable to distinguish between closely related nucleic acid sequences. In some embodiments, the primer duplex systems described herein can be used in nucleic acid microarrays in order to, for example, improve the specificity of microarray analysis. In some instance, microarrays assays can be performed using methods well known in the art, with the exception that the primer duplex systems described herein can be used in place of conventional nucleic acid primers.

Figure 12A:
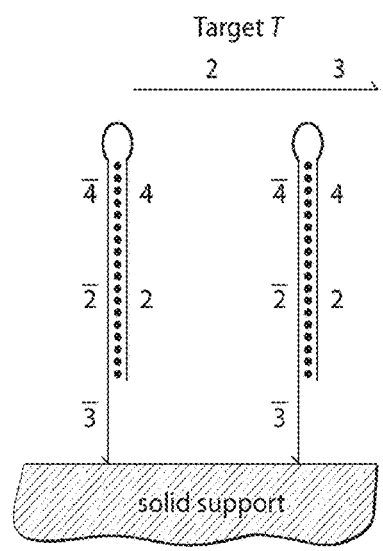
Figure 12B:
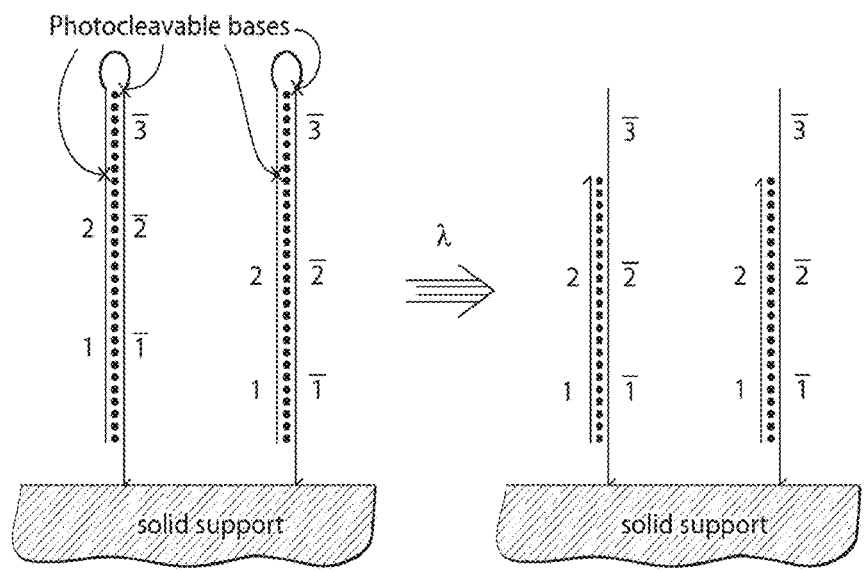

For example, as depicted in FIG. 12A, in certain embodiments, a hairpin primer duplex system from can be directly synthesized or immobilized on a microarray chip using standard techniques. In other embodiments, a two-stranded primer duplex system can be used in a nucleic acid microarray. In some embodiment, hairpin structures including two photocleavable bases at predefined positions can be synthesized as in FIG. 12A. Subsequent exposure to light cleaves the hairpin, yielding the two-stranded complexes functionalized to the array surface (FIG. 12B). Other methods, such as use of nicking or restriction enzymes, can also be used to prepare two-stranded complexes.

Nucleic Acid Synthesis Reactions, Including Amplification Reactions

Primer duplexes and systems disclosed here can be used in some embodiments to improve the specificity of a primer-based amplification reaction, including polymerase chain reaction (PCR), strand displacement amplification, or transcription mediated amplification, by substituting a primer duplex system described herein for the nucleic acid primers in a primer based amplification reaction known in the art.

Figure 13:
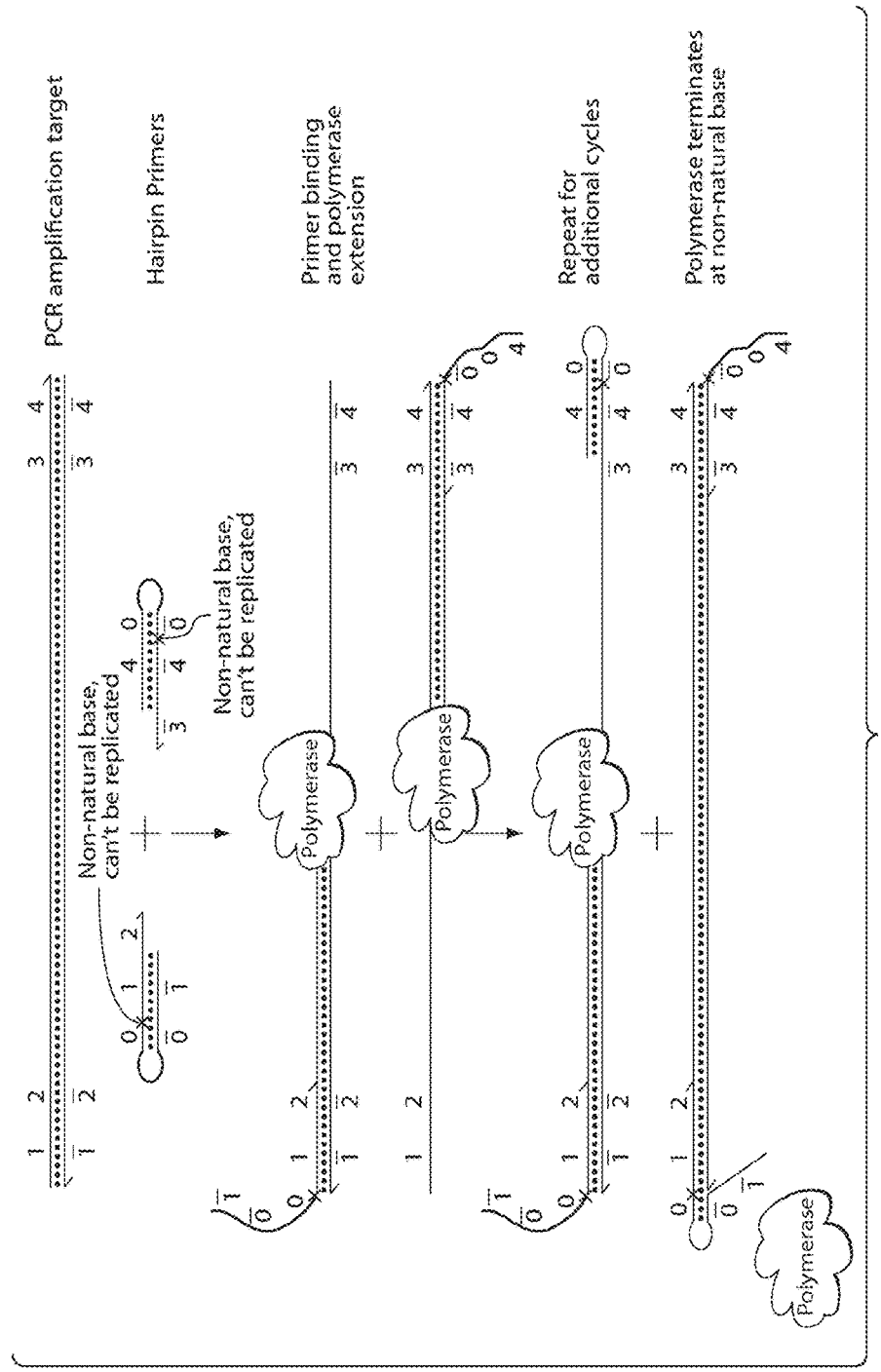

For example, as depicted in FIG. 13, by using as PCR primers the hairpin primer duplex systems of the type depicted in FIG. 4, it is possible to improve the specificity of PCR for a variety of (e.g., biotechnological) applications. In this example, a target nucleic acid sequence is amplified by forming a solution comprising a primer duplex system with the target nucleic acid and standard reagents for performing an amplification reaction and incubating the solution under conditions such that an amplification reaction occurs. In certain embodiments, non-natural bases are incorporated into a hairpin primer duplex primer systems in order to prevent replication of the hairpin itself.

In some embodiments, the primer duplexes described herein can be adapted for use in amplifying target nucleic acids that typically require amplification by any one or more of the following PCR methods: allele-specific PCR, assembly PCR, asymmetric PCR, helicase-dependent amplification, intersequence-specific PCR (ISSR), inverse PCR, ligation-mediated PCR, methylation-specific PCR (MSP), miniprimer PCR, multiplex PCR, nested PCR, overlap-extension PCR, quantitative PCR (Q-PCR), reverse transcription PCR (RT-PCR), solid phase PCR, thermal asymmetric interlaced PCR (TAIL-PCR), or touchdown PCR. In some instances, the primer duplexes and methods described herein may be used or adapted for use in any one of the foregoing PCR methods or may substitute (used instead of) any one of the foregoing PCR methods. A brief description of each of the foregoing PCR methods is presented below.

Allele-specific PCR is a diagnostic or cloning technique based on single-nucleotide polymorphisms (SNPs) (single-base differences in DNA). It typically requires prior knowledge of a DNA sequence, including differences between alleles.

Assembly PCR or polymerase cycling assembly (PCA) is an artificial synthesis of long DNA sequences by performing PCR on a pool of long oligonucleotides with short overlapping segments. The oligonucleotides alternate between sense and antisense directions, and the overlapping segments determine the order of the PCR fragments, thereby selectively producing the final long DNA product (Stemmer et al. *Gene* 164(1): 49-53 (1995)).

Asymmetric PCR preferentially amplifies one DNA strand in a double-stranded DNA target. It can be used in sequencing and hybridization probing where amplification of only one of the two complementary strands is required (Innis et al. *Proc. Natl. Acad. Sci. USA* 85(24): 9436-40 (1988)).

Helicase-dependent amplification is similar to traditional PCR, but typically uses a constant temperature rather than cycling through denaturation and annealing/extension cycles. DNA helicase, an enzyme that unwinds DNA, is used in place of thermal denaturation (Vincent et al. *EMBO Reports* 5(8): 795-800 (2004)).

Intersequence-specific PCR (ISSR) is a PCR method for DNA fingerprinting that amplifies regions between simple sequence repeats to produce a unique fingerprint of amplified fragment lengths (Zietkiewicz et al. *Genomics* 20(2): 176-83 (1994)).

Inverse PCR is commonly used to identify the flanking sequences around genomic inserts. It involves a series of DNA digestions and self-ligation, resulting in known sequences at either end of the unknown sequence (Ochman et al. *Genetics* 120 (3): 621-623 (1988)).

Ligation-mediated PCR uses small DNA linkers ligated to the DNA of interest and multiple primers annealing to the DNA linkers; it has been used for DNA sequencing, genome walking, and DNA footprinting (Mueller et al. *Science* 246(4931): 780-786 (1988)).

Methylation-specific PCR (MSP) is used to detect methylation of CpG islands in genomic DNA. DNA is first treated with sodium bisulfite, which converts unmethylated cytosine bases to uracil, which is recognized by primers as thymine.

Miniprimer PCR uses a thermostable polymerase (S-Tbr) and is used to amplify conserved DNA sequences, such as the 16S (or eukaryotic 18S) rRNA gene (Isenbarger et al. *Applied and Environmental Microbiology* 74(3): 840-9. (2008)).

Multiplex-PCR targets multiple genes at once, gaining additional information from a single test-run that otherwise would require several times the reagents and more time to perform.

Nested PCR increases the specificity of DNA amplification, by reducing background due to non-specific amplification of DNA. Two sets of primers are used in two successive PCRs. In the first reaction, one pair of primers is used to generate DNA products, which besides the intended target, may still consist of non-specifically amplified DNA fragments. The product(s) are then used in a second PCR with a set of primers whose binding sites are completely or partially different from and located 3' of each of the primers used in the first reaction.

Overlap-extension PCR or splicing by overlap extension (SOE) is a genetic engineering technique that is used to splice together two or more DNA fragments that contain complementary sequences. It is used to join DNA pieces containing genes, regulatory sequences, or mutations; the technique enables creation of specific and long DNA constructs.

Quantitative PCR (Q-PCR) is used to measure the quantity of a PCR product (commonly in real-time). It quantitatively measures starting amounts of DNA, cDNA, or RNA. Q-PCR is commonly used to determine whether a DNA sequence is present in a sample and the number of its copies in the sample.

Reverse Transcription PCR (RT-PCR) is used for amplifying DNA from RNA. Reverse transcriptase reverse transcribes RNA into cDNA, which is then amplified by PCR. RT-PCR is widely used in expression profiling, to determine the expression of a gene or to identify the sequence of an RNA transcript, including transcription start and termination sites. If the genomic DNA sequence of a gene is known, RT-PCR can be used to map the location of exons and introns in the gene. The 5' end of a gene (corresponding to the transcription start site) is typically identified by RACE-PCR (Rapid Amplification of cDNA Ends).

Solid Phase PCR encompasses multiple meanings, including polony amplification (where PCR colonies are derived in a gel matrix, for example), bridge PCR (primers are covalently linked to a solid-support surface), conventional solid phase PCR (where asymmetric PCR is applied in the presence of solid support bearing primer with sequence matching one of the aqueous primers) and enhanced solid phase PCR (where conventional solid phase PCR can be improved by employing high melting temperature ($T_m$) and nested solid support primer with optional application of a thermal 'step' to favor solid support priming).

Thermal asymmetric interlaced PCR (TAIL-PCR) is used for isolation of an unknown sequence flanking a known sequence. Within the known sequence, TAIL-PCR uses a nested pair of primers with differing annealing temperatures; a degenerate primer is used to amplify in the other direction from the unknown sequence (Liu et al. *Genomics* 25 (3): 674-81. (1995)).

Touchdown PCR (step-down PCR) is a variant of PCR that aims to reduce nonspecific background by gradually lowering the annealing temperature as PCR cycling progresses. The annealing temperature at the initial cycles is usually a few degrees (3-5° C.) above the Tm of the primers used, while at the later cycles, it is a few degrees (3-5° C.) below the primer Tm. The higher temperatures give greater specificity for primer binding, and the lower temperatures permit more efficient amplification from the specific products formed during the initial cycles.

The temperature of the reaction solutions may be sequentially cycled between a denaturing state, an annealing state, and an extension state for a predetermined number of cycles. The actual times and temperatures can be enzyme, primer, and target dependent.

For any given reaction, denaturing states can range in certain embodiments from about 75° C. to about 100° C. The annealing temperature and time can influence the specificity and efficiency of primer binding to a particular locus within a target nucleic acid and may be important for particular PCR reactions.

For any given reaction, annealing states can range in certain embodiments from about 20° C. to about 75° C. In some embodiments, the annealing state can be performed at about 20° C. to about 25° C., about 25° C. to about 30° C., about 30° C. to about 35° C., or about 35° C. to about 40° C., about 40° C. to about 45° C., about 45° C. to about 50° C. In certain embodiments, the annealing state can be performed at room temperature (e.g., 20° C. or 25° C.). In some embodiments, the annealing state can be performed at a temperature of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.

Extension temperature and time may impact the allele product yield and are understood to be an inherent property of the enzyme under study. For a given enzyme, extension states can range in certain embodiments from about 60° C. to about 75° C.

In any of the foregoing embodiments, any DNA or RNA polymerase (enzyme that catalyzes polymerization of nucleotides into a nucleic acid strand) may be utilized, including thermostable polymerases and reverse transcriptases (RTases). Examples include *Bacillus stearothermophilus* pol I, *Thermus aquaticus* (Taq) pol I, *Pyrccoccus furiosus* (Pfu), *Pyrococcus woesei* (Pwo), *Thermus flavus* (Tfl), *Thermus thermophilus* (Tth), *Thermus litoris* (Tli) and *Thermotoga maritime* (Tma). These enzymes, modified versions of these enzymes, and combination of enzymes, are commercially available from vendors including Roche, Invitrogen, Qiagen, Stratagene, and Applied Biosystems. Representative enzymes include PHUSION® (New England Biolabs, Ipswich, Mass.), Hot MasterTaq™ (Eppendorf), PHUSION® Mpx (Finnzymes), PyroStart® (Fermentas), KOD (EMD Biosciences), Z-Taq (TAKARA), and CS3AC/LA (KlenTaq, University City, Mo.).

Salts and buffers include those familiar to those skilled in the art, including those comprising $MgCl_2$, and Tris-HCl and KCl, respectively. Buffers may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphosphate (dCTP), deoxyguanosine triphosphate (dGTP), and deoxythymidine triphosphate (dTTP), and are also added to a reaction adequate amount for amplification of the target nucleic acid.

Also provided herein are methods comprising (1) hybridizing a complement strand of a primer duplex to a target nucleic acid, thereby dissociating the complement strand from its protector strand, and (2) extending the complement strand at its 3' end, in a target-complementary manner, in the presence of a polymerase.

Also provided herein are methods comprising performing a nucleic acid synthesis reaction in the presence of a target nucleic acid, a polymerase, and one or more of the primer duplexes of any one of the embodiments described herein.

A "nucleic acid synthesis reaction" refers to any reaction in which a nucleic acid is synthesized. Examples include nucleic acid amplification reactions such as polymerase chain reaction (PCR) or a variation thereof (described elsewhere herein), a transcription reaction, a reverse transcription reaction, sequencing-by-synthesis, or other primer extension reactions (see also, Lizardi et al. *Nat. Genet.* 19: 225-32 (1998), incorporated by reference).

In some instances, a method is provided that comprises (1) synthesizing a complement strand having a target-non-specific balance region, a target-specific branch migration region, and a target-specific toehold region; (2) synthesizing a protector strand having a balance region complementary to the complement strand and a branch migration region complementary to the complement strand; and (3) hybridizing the complement strand to the protector strand to form a primer duplex.

In some instances, a method is provided that comprises (1) providing a complement strand having a target-non-specific balance region, a target-specific branch migration region, and a target-specific toehold region; (2) providing a protector strand having a balance region complementary to the complement strand and a branch migration region complementary to the complement strand; and (3) combining the complement strand to the protector strand to form a primer duplex.

In some instances, a method is provided that comprises (1) providing a plurality of nucleic acid molecules comprising a target nucleic acid; (2) providing at least one primer duplex having (i) a balance region, (ii) a branch migration region complementary to the target nucleic acid, and (iii) a toehold region; and (3) combining in a single reaction the plurality of target nucleic acids, at least one primer duplex, and a polymerase under conditions suitable for nucleic acid hybridization.

Also provided herein are methods of amplifying at least one target nucleic acid of interest, comprising (1) providing a plurality of nucleic acid molecules comprising at least one target nucleic acid, (2) providing at least one primer duplex having (i) a balance region, (ii) a branch migration region, and (iii) a toehold region; and (3) combining in a single reaction the plurality of target nucleic acid molecules, at least one primer duplex, and a polymerase under conditions suitable for amplification of the at least one target nucleic acid. In certain embodiments multiple unique target nucleic acids are amplified in a single reaction or in multiple reactions, for example, in one or more multiplexed PCR amplification reaction. In some embodiments, about 10 to 100, about 100 to about 1000, about 1000 to about 10,000, or about 10,000 to about 100,000 nucleic acid targets are amplified. The number of different primer duplexes in a reaction will depend on the number of desired targets.

In some embodiments, provided herein are methods of discriminating against spurious nucleic acid molecules having one or more nucleotide changes relative to a target nucleic acid molecule, comprising (1) providing a plurality of nucleic acid molecules comprising at least one target nucleic acid, (2) providing at least one primer duplex having (i) a balance region, (ii) a branch migration region, and (iii) a toehold region; and (3) combining in a single reaction the plurality of target nucleic acid molecules, at least one primer duplex, and a polymerase under conditions suitable for amplification of the at least one target nucleic acid molecule.

Any one of the methods described herein may further comprise providing or combining in a single reaction one or more of the following reagents: buffer (e.g., KCl, MgCl$_2$, Tris-HCl), dNTPs (e.g., dATP, dCTP, dGTP, dTTP at concentrations of, e.g., about 50 to about 100 µM), polymerase (e.g., at concentrations of about 0.5-2.0 units per 50 µl reaction), and/or water. The concentration of each strand of a primer duplex in a single reaction varies depending on, for example, the concentration of target nucleic acid. In some embodiments, about 5 to about 50 pg of plasmid or viral target may be used, or about 50 ng to about 500 ng of genomic target may be used. In such instances, the concentration each primer (the first strand and the second strand) may be, for example, about 0.05 µM to about 1 µM. In particular embodiments, the concentration of each primer is about 1 nM to about 1 µM.

In any one of the embodiments described herein, a single reaction may be subject to cyclic temperature changes such that a dsDNA structure undergoes multiple rounds of denaturation, subsequent primer annealing, and polymerase-based extension, for example, similar to those conditions used for standard PCR. In some embodiments, the temperature range for a denaturation step is about 90 to about 95° C. In certain embodiments, an initial denaturation step of about 1 to about 5 minutes is required prior to cycling; the exact amount of time may depend on GC content of the nucleic acid target of interest. In certain embodiments, the denaturation step during a cycling reaction is about 15 to about 30 seconds. In some embodiments, the temperature range for an annealing step is about 50° C. to about 60° C. In some embodiments, the annealing step is about 20° C. to about 40° C. in particular embodiments, the annealing step is at room temperature (about 20° C. or about 25° C.). In certain embodiments, the annealing step during a cycling reaction is about 15 to about 30 seconds. In some embodiments, the temperature range for an extension step is about 70° C. to about 75° C. In certain embodiments, the extension step during a cycling reaction is about 45 to about 60 seconds. The temperature, time of each step, and number of cycles of a cycling reaction may depend on the length of the nucleic acid target(s) of interest as well as the polymerase being used. Longer target may require, for example, longer extension times. One example of cycling conditions for a 500 nucleotide target is set forth in Table 2.

TABLE 2

| 1 cycle | 98° C. | 2 minutes |
|---|---|---|
| 25 cycles | 98° C. | 15 seconds |
| | 30° C., 35° C., 40° C., 45° C., 50° C., 55° C., or 60° C. | 15 seconds |
| | 72° C. | 45 seconds |
| 1 cycle | 72° C. | 5 minutes |
| 1 cycle | 4° C. | indefinite |

In any one of the embodiments described herein, a single reaction (e.g., nucleic acid amplification) may proceed at room temperature (e.g., about 20° C. or about 25° C.). In certain embodiments, a single reaction proceeds at room temperature for about 1 hour.

In any one of the methods described herein, the second protector strand of a primer duplex may be provided in excess of the first complementary strand or in excess of the annealed primer duplexes. For example, in some embodiments, the second strand is provided at a concentration about 1× to about 10× (e.g., 1×, 2×, 3×, 4×, 5×, 6×, 7×, 8×, 9×, or 10×) the concentration the first strand, or about 1× to about 10× (e.g., 1×, 2×, 3×, 4×, 5×, 6×, 7×, 8×, 9×, or 10×) the concentration of the annealed primer duplex. In some embodiments, the first strand is provided at a concentration of about 0.05 µM to about 1 µM, while the second strand is provided at a concentration of about 0.10 µM to about 2 µM, or about 0.15 µM to about 3 µM, about 0.2 µM to about 4 µM, or about 0.25 µM to about 5 µM.

Any one of the methods described herein may comprise a method selected from: allele-specific PCR, assembly PCR, asymmetric PCR, helicase-dependent amplification, intersequence-specific PCR (ISSR), inverse PCR, ligation-mediated PCR, methylation-specific PCR (MSP), miniprimer PCR, multiplex PCR, nested PCR, overlap-extension PCR, quantitative PCR (Q-PCR), reverse transcription PCR (RT-PCR), solid phase PCR, thermal asymmetric interlaced PCR (TAIL-PCR), and touchdown PCR.

In any one of the methods described herein, the yield of amplified nucleic acid target may be about 30% to about 100%. In some embodiments, the yield is at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or at least 100%.

In any one of the methods described herein, the amplified nucleic acid product may be purified. Nucleic acid purification methods are well-known to those of skill in the art and include, phenol extraction, guanidinium isothiocyanate, alcohol precipitation, DEAE (ion exchange), size exclusion chromatography (SEC), cesium chloride, extraction from agarose, silica, and other column-based purification methods.

In any one of the methods described herein, a purified amplified target nucleic acid may be about 30% to about 100% pure. In some embodiments, the purity is at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100% pure.

Imaging

Figure 14:
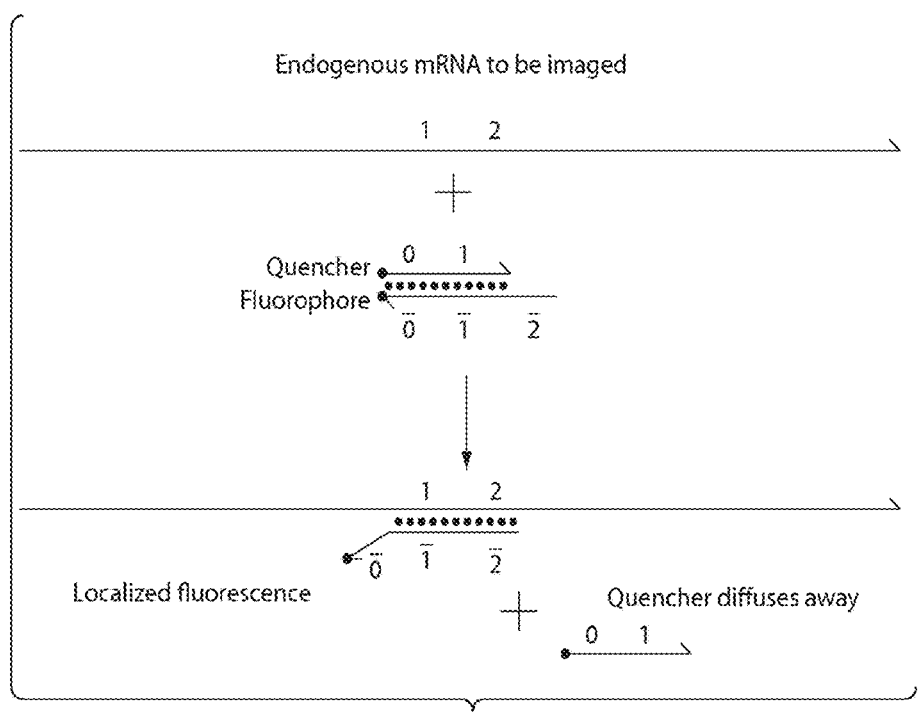

The primer duplexes and systems described herein can also be used to improve the specificity of in situ imaging assays. Nonspecific interactions between biological RNAs and fluorophore-labeled primers are frequently a source of background noise. Thus, as depicted in FIG. 14, the use fluorophore-labeled nucleic acid primer systems described herein in the place of conventional primers, in some embodiments, greatly improves the performance of existing in situ imaging techniques. Notably, by labeling the complement strand or domain with a fluorophore and the protector strand or domain with a quencher, the primer duplex system will only produce a detectable signal when it is bound to the target.

Single Nucleotide Polymorphism (SNP) Detection

The accurate detection of the location and identity of single nucleotide polymorphisms (SNPs) is of great interest for both research and therapeutic purposes. The kinetic discrimination methods described herein are therefore useful for the convenient identification SNPs.

Kits

Provided herein are kits comprising (1) at least one complement strand having a balance region, a branch migration region, and a toehold region, and (2) at least one protector strand having a balance region and a branch migration region.

Provided herein are kits comprising at least one primer duplex comprising (1) at least one complement strand or region having a balance region, a branch migration region, and a toehold region, and (2) at least one protector strand or region having a balance region and a branch migration region.

Any one of the kits described herein may further comprise a polymerase. Any one of the kits provided herein may further comprise one or more agent selected from buffer (e.g., KCl, MgCl$_2$, Tris-HCl), dNTPs (e.g., dATP, dCTP, dGTP, dTTP), and water. Any one of the kits provided herein may comprise protector strand is molar excess of the primer. Any one of the kits provided herein may further comprise instructions or directions for obtaining instructions (e.g., from a website) for using the components of the kits. Any one of the kits provided herein may further comprise at least one reaction tube, well, chamber, or the like.

Any one of the primers or primer systems described herein may be provided in the form of a kit or comprised within a kit.

EXAMPLES

In accordance with the invention, the above limitations of PCR, transcription, and reverse transcription can be overcome through the use of highly specific primer duplexes. The experiments described herein demonstrate that primer duplexes can reliably discriminate against targets with single-base changes (FIG. 16) for both DNA and RNA targets and primers (FIG. 17). The correct target hybridizes to the 7/5 primers with roughly 50% yield, but even a large excess (200×) of targets with a single-base change is insufficient to significantly hybridize. Primer duplexes were designed and tested for multiple different targets, and each primer duplex achieved high discrimination factors versus single-nucleotide changes (FIG. 17). Quantitatively, the median discrimination in hybridization yield to a spurious target with a single-nucleotide change is 26.

Figure 18A:
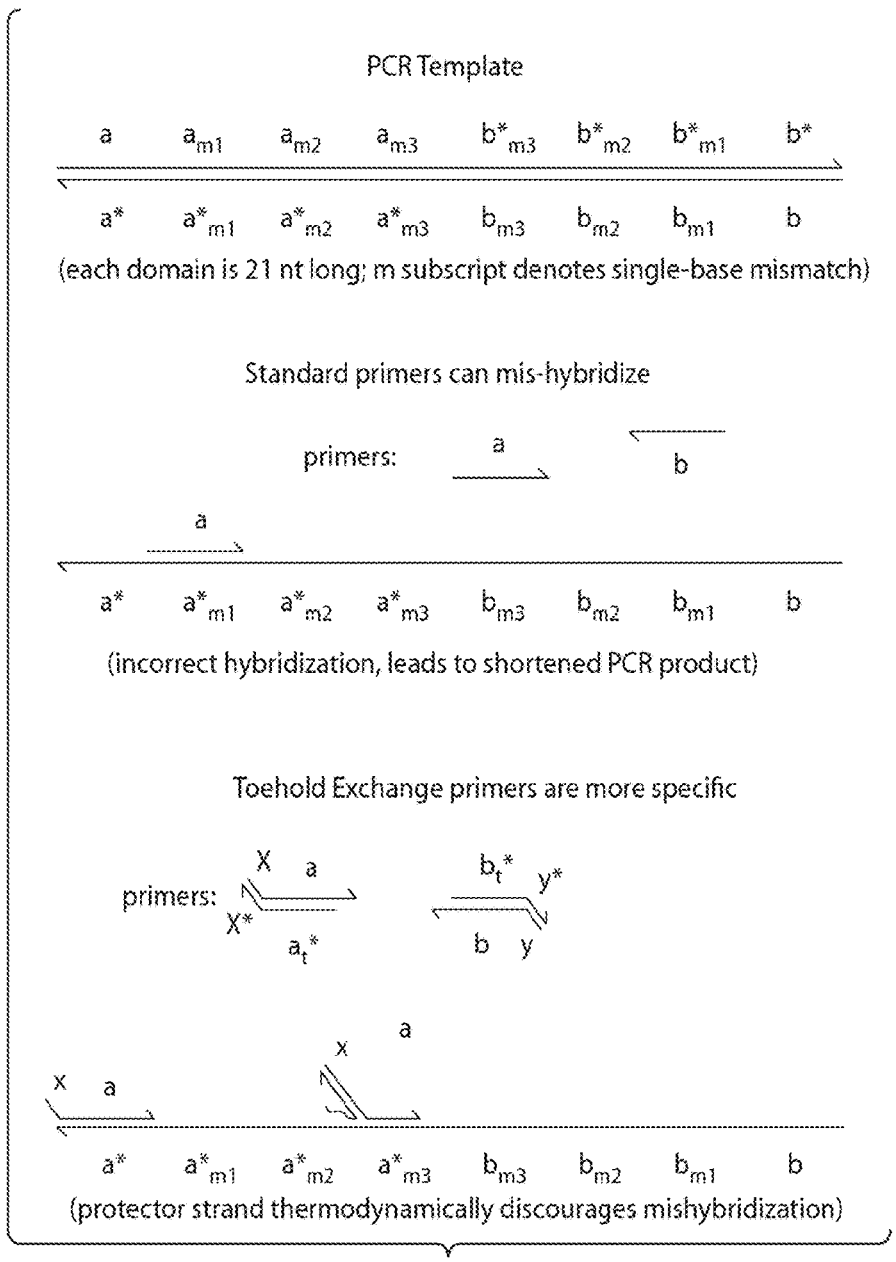
FIGS. 18A-18B show experimental results using duplex primers to improve the PCR yield of a quasi-repetitive target.
Figure 18B:
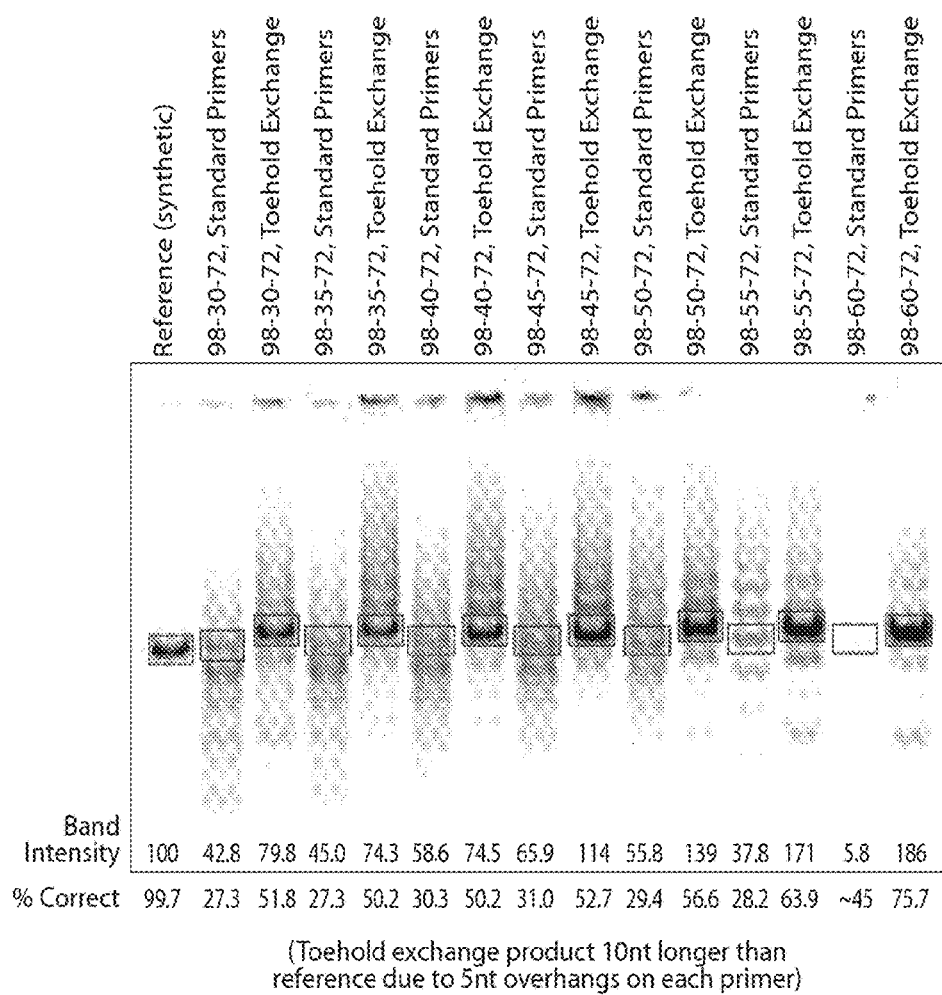

The primer duplexes were used for PCR in a proof-of-principle demonstration (FIGS. 18A and 18B). A semi-repetitive target nucleic acid was designed, which is difficult to amplify by traditional PCR (PCR without the use of the instant primer duplexes). The yield of standard 21 nucleotide primers and the primer duplexes were calculated. Many different thermal cycling schedules were determined in order to investigate the range of function. Based on the length and nucleotide content of the primer duplexes, standard PCR condition would predict that the annealing temperature of the primers would 55° C. Surprisingly, as an example, even under conditions most unfavorable for primer duplex annealing (35° C. and 40° C.), the fraction (50.2%) of correct-length product amplified using the primer duplexes was higher than the fraction (31.0%) of correct-length product amplified using standard primers under their most favorable PCR conditions (45° C.). Furthermore, in this particular experiment, the primer duplexes were arbitrarily designed (7 nucleotide toehold region and 5 nucleotide balance region), and were not optimized for PCR yield performance. Thus, it is likely that even higher PCR specificity can be achieved through optimization of the instant primer duplexes.

Figure 15A:
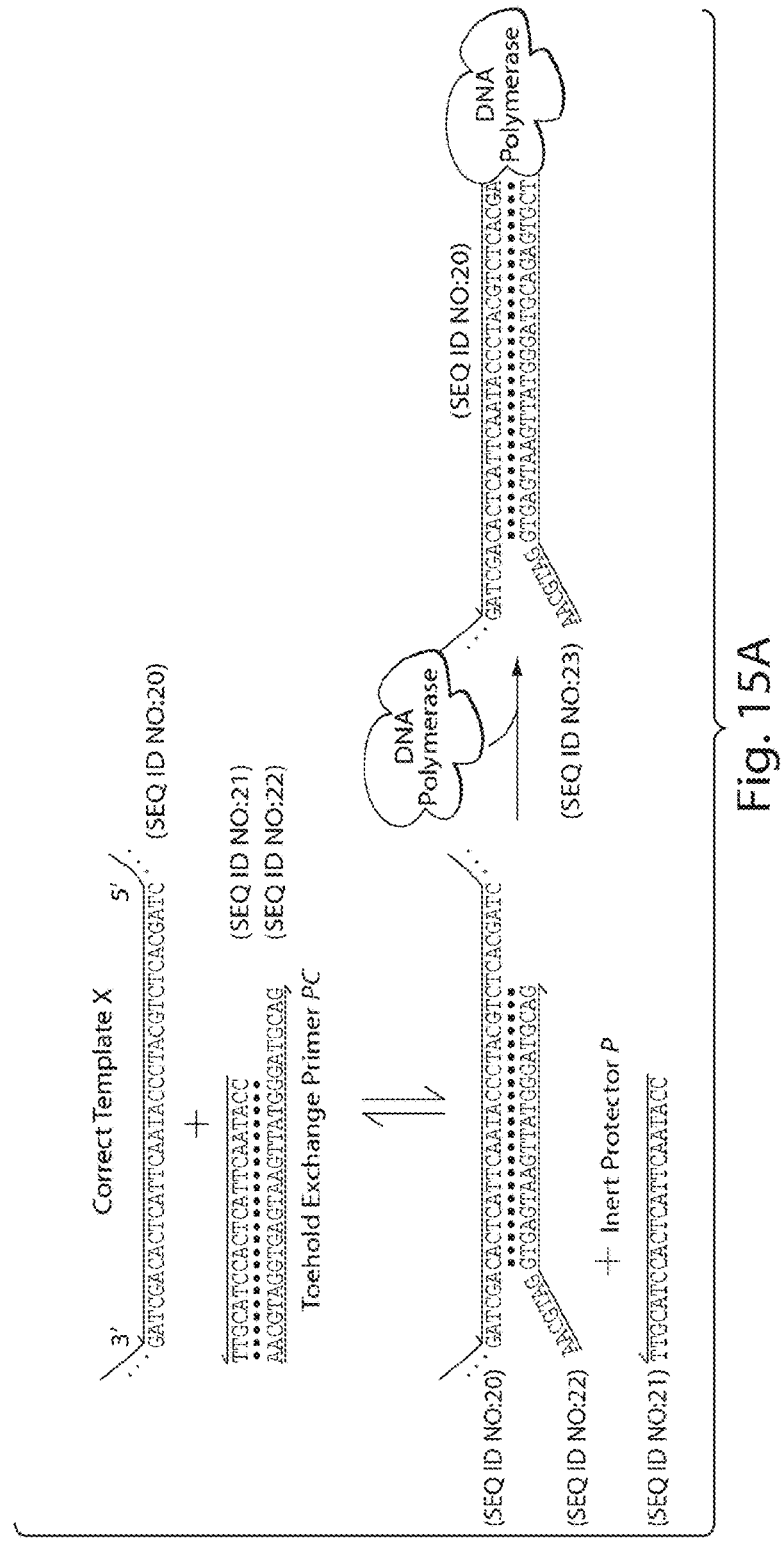
FIGS. 15A and 15B depict highly specific polymerase chain reaction (PCR) using the primer duplexes provided herein.
Figure 15B:
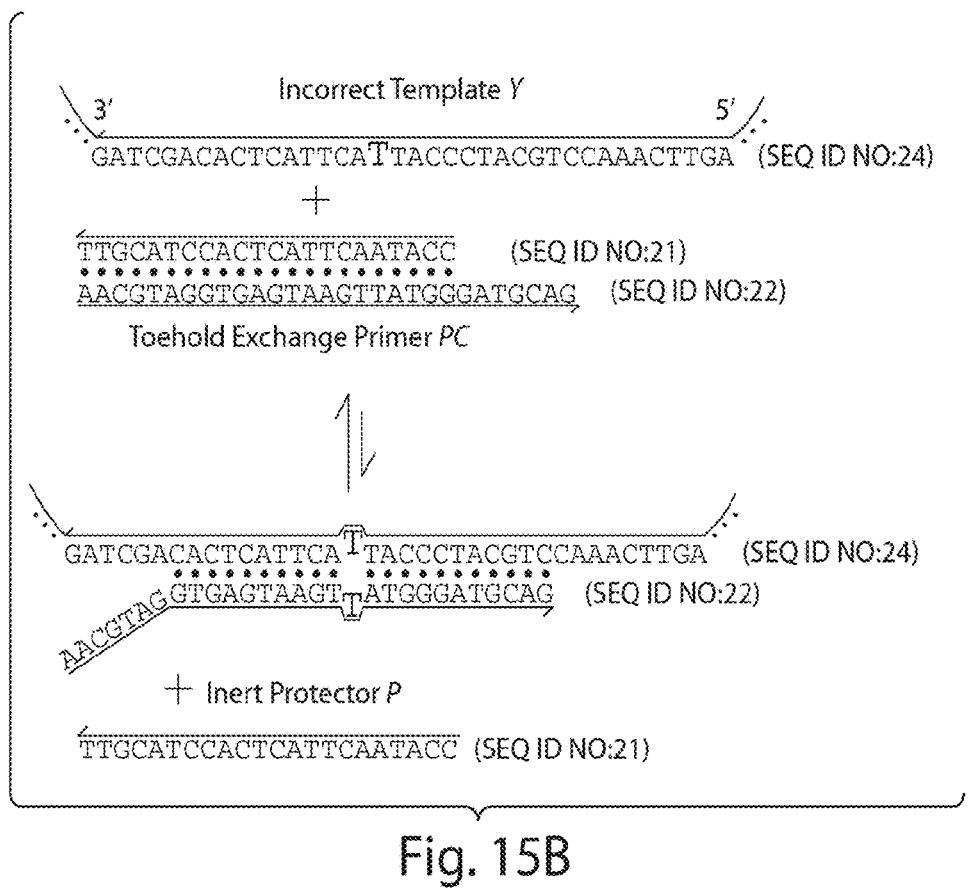
Figure 16A:
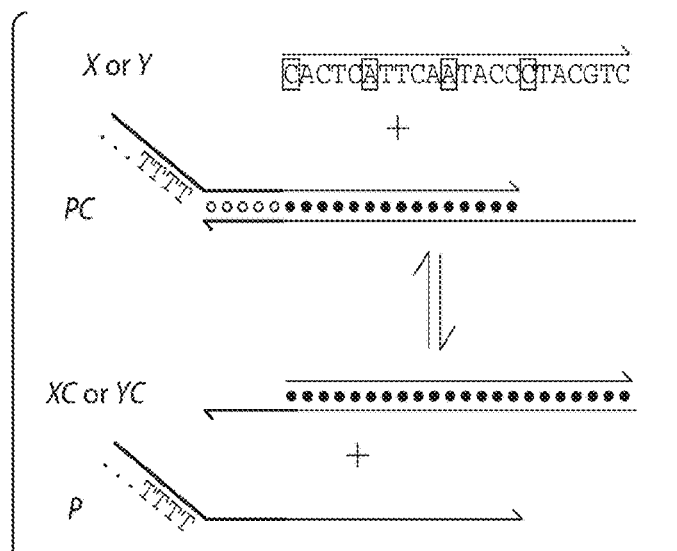
FIGS. 16A-16E show experimental demonstrations of primer hybridization with single nucleotide discrimination.
Figure 16B:
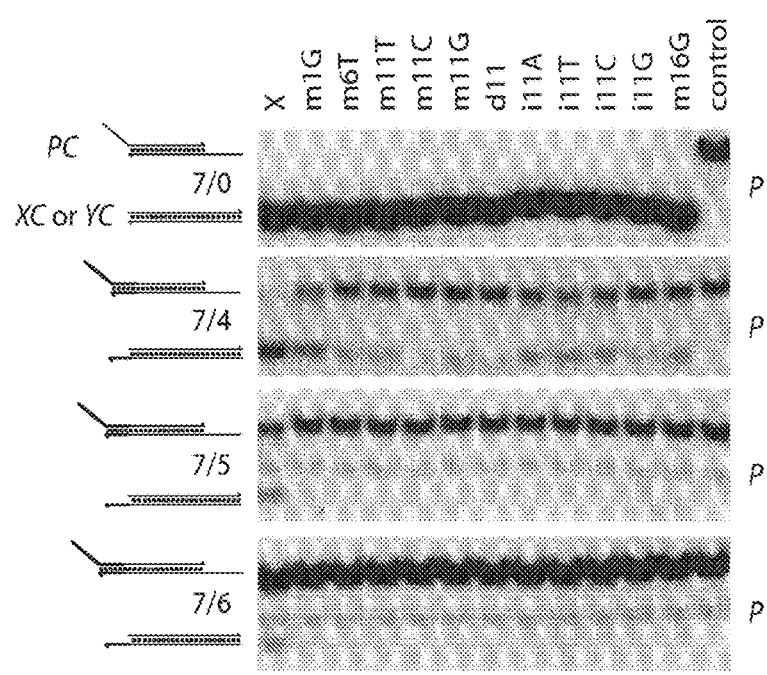
Figure 16C:
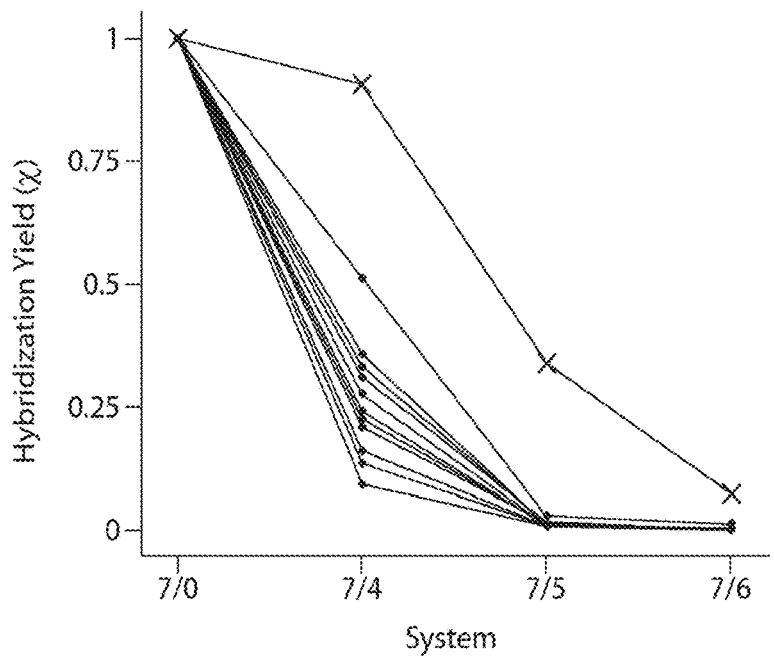
Figure 16D:
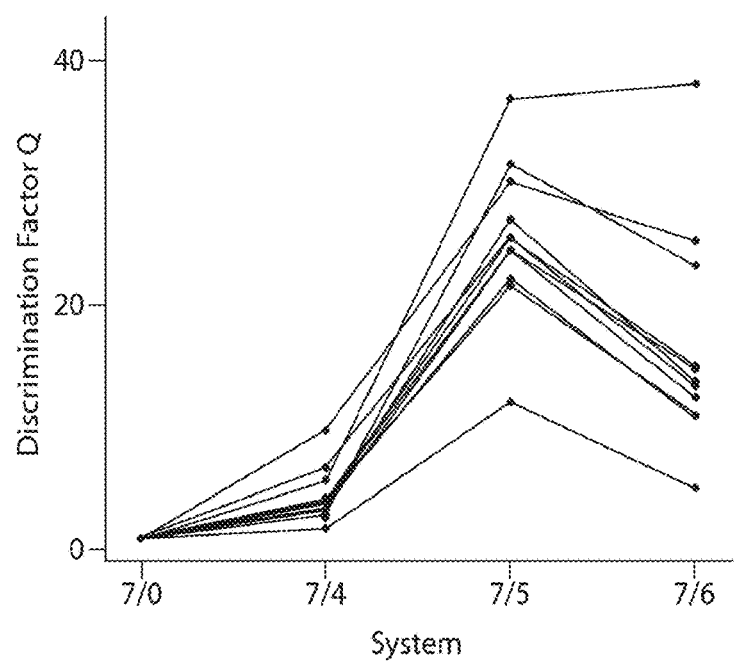
Figure 16E:
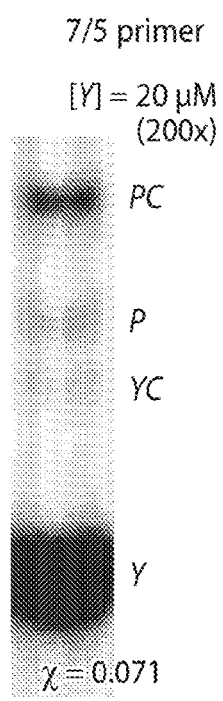
Figure 17A:
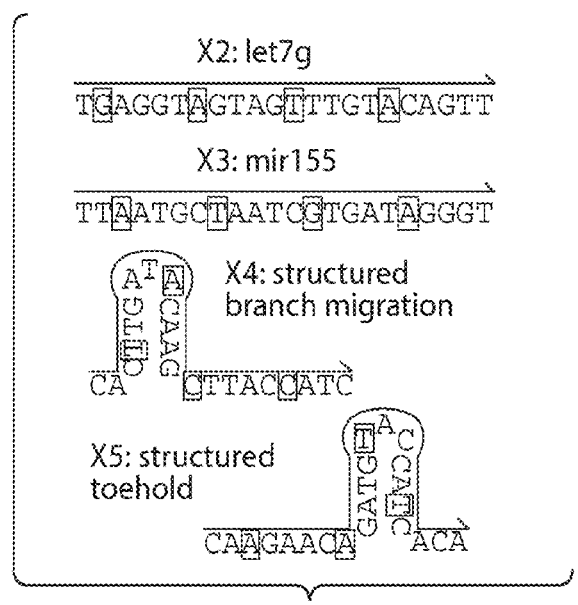
FIGS. 17A-17D show additional experimental results and statistics on the single-base discrimination abilities of primer duplexes.
Figure 17B:
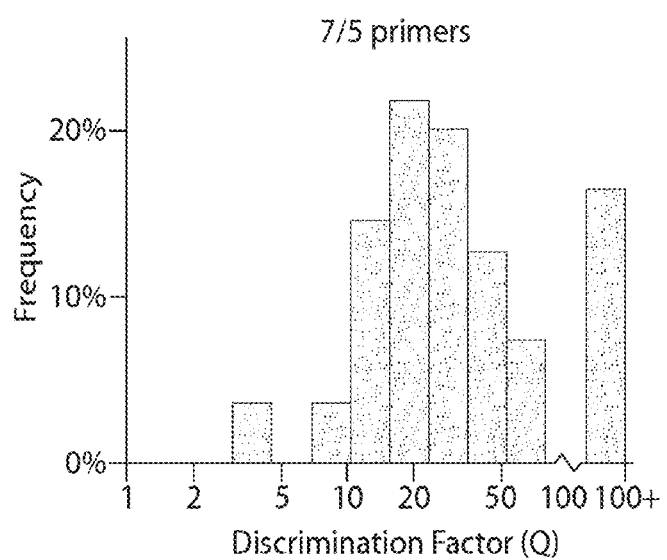
Figure 17C:
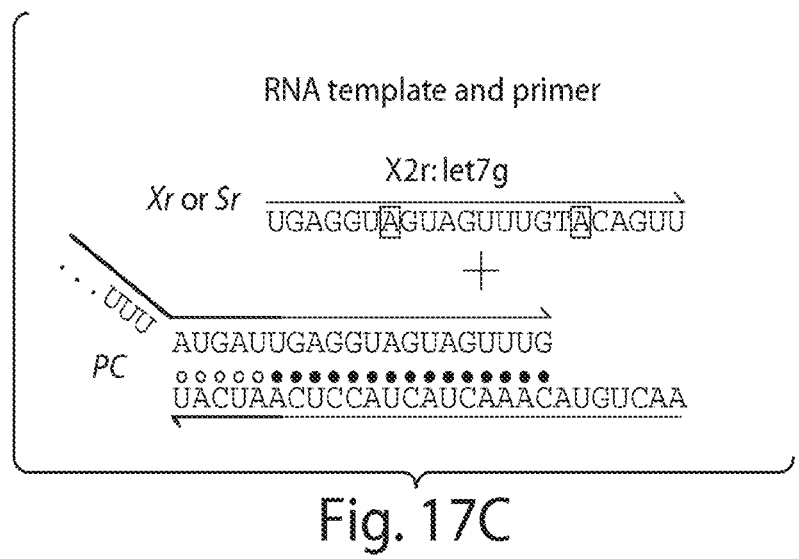
Figure 17D:
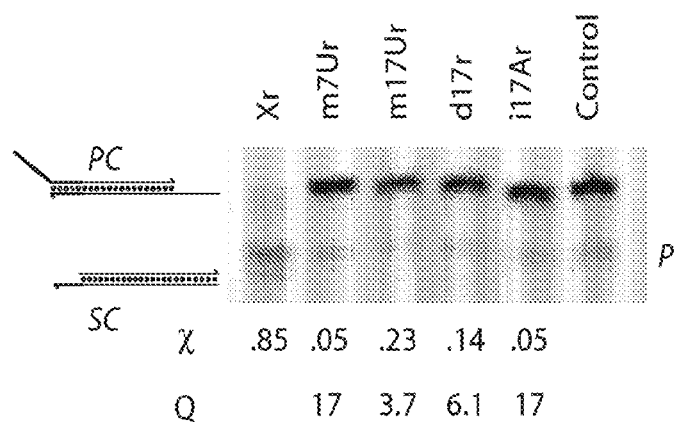

FIG. 15 shows highly specific PCR using the primer duplexes provided herein. In FIG. 5A, the primer "PC" is comprised of a complement strand "C" and a protector strand "P". When PC binds to the intended target at the correct position "X", the single-stranded protector oligonucleotide "P" is released as an inert waste product, and the primed target is elongated by the DNA polymerase. In FIG. 5B, when the primer PC binds to an unintended target or to the correct target at an incorrect position (in either case, denoted "Y"), the displacement of the protector from the complementary strand "C" is thermodynamically unfavorable, and kinetically quick to reverse. Consequently, off-target amplification (e.g., amplification of Y rather than X) is expected to be significantly reduced.

FIG. 16. shows an experimental demonstration of primer hybridization with single nucleotide discrimination. In FIG. 16A, short synthetic DNA target "X" or spurious target "Y" is reacted with the primer. (The poly-T tail on the protector strand "P" serves to distinguish products from reactants on a gel.) Shown in red boxes are the positions of single-base changes for spurious target Y. FIG. 16B shows native polyacrylamide gel results. The primer "PC" was prepared at a 2:1 ratio of protector P to complement C, and annealed at 1 μM concentration of PC. Either the correct or spurious targets were added to achieve final concentrations of 200 nM target (X or Y), 100 nM PC, and 100 nM P. In some embodiments, a reaction may have an excess of the protector (P) primer. For example, in some embodiments, the protector strand is provided at a concentration of about 1× to about 10× (e.g., 1×, 2×, 3×, 4×, 5×, 6×, 7×, 8×, 9×, or 10×) of the complement strand. All reactions proceeded at room temperature (25° C.) for 1 hour. As an example, the designation "7/4" denotes a primer that possesses 7 nucleotides of single-stranded nucleotides (as a 3' overhang) to initiate hybridization to the target, and the protector spontaneously dissociates 4 nucleotides to be released. FIG. 16C is a plot of hybridization yields inferred from data shown in FIG. 16B. Shown as plot "X" is the hybridization of the primer to the correct target X, while the remaining "dotted" plots show the hybridization to the spurious targets Y. The 7/4, 7/5 and 7/6 primers all discriminate in their hybridization yields (χ) between the correct and the spurious targets. The 7/0 target does not. In FIG. 16D, the discrimination factor (Q) is a quantitative measurement of the specificity of the primer, and is calculated as the hybridization yield (χ) of the correct target divided by the hybridization yield (χ) of the spurious target. In 16E, there is little hybridization of the 7/5 primer to a spurious target Y even when such target is present in large excess (i.e., 200-fold).

FIG. 17. shows additional experimental results and statistics on the single-base discrimination abilities of primer duplexes. FIG. 17A shows that four additional targets and sets of primers were constructed and tested: two based on naturally occurring microRNA sequences, and two designed to intentionally possess significant secondary structure. FIG. 17B shows a histogram of the discrimination factors (Q) achieved by the 7/5 primers for each target. Due to limitations of the gel scanner, it was not possible to reliably measure discrimination factors above 100, and these were all grouped as "100+." FIG. 17C show RNA target and primer. The target sequence is a synthetic RNA oligonucleotide with sequence identical to the human let7g microRNA. FIG. 17D shows native PAGE results. The PC primer was prepared at a 2:1 ratio of protector P to complement C, and annealed at 3 μM concentration. Either the correct or spurious targets were added to achieve final concentrations of 2 μM X or Y, 1 μM PC, and 1 μM P. The correct target successfully binds to the primer; the hybridization yield of targets with single-nucleotide mismatches is low.

FIG. 18 shows experimental results using duplex primers to improve the PCR yield of a quasi-repetitive target. FIG. 18A shows a quasi-repetitive PCR target (168 nt) that traditional PCR primers struggle to amplify with high yield. Here, a* is the correct target for X1. The remaining sites labeled a*m1 (which is X1-m17G), a*m2 (which is X1-m9T), and a*m3 (which is X1-m11G) are not the correct targets. Similarly, b* is the correct target for X2, and b*m1 (which is X2-m3T), b*m2 (which is X2-m11C), and b*m3 (which is X2-m18T) are not the correct targets. Thus, the outer-most binding sites are the perfect binding sites for the primers, but there are also 3 additional single-base mismatch primer binding sites between the perfect sites. The primer duplexes bind by 7 nucleotides to the target, and the protector must spontaneously dissociate 5 nucleotides to be released. The primer duplex was designed so that its 3' end cannot be extended by the polymerase. The toehold region of the complement strand was designed at the 3' end, instead of the 5' end as in previous designs. In FIG. 18B, primer duplexes show significantly higher yield of correct length product, as compared to standard primers. Each lane is labeled with the primers used as well as the temperature cycling schedule (e.g., "98-40-72" indicates denaturation at 98° C., annealing at 40° C., and elongation at 72° C.). The left-most lane shows the synthetic oligonucleotide reference. The lower numbers labeled "% Correct" indicate the relative intensity of band corresponding to the correct length product compared to the integrated intensity of all bands in the lane. The primer duplex PCR product appears as 10 nucleotides longer than the reference and the standard PCR product because of the 5 nucleotide of overhangs (toehold region) on each primer.

EQUIVALENTS

Those skilled in the art will recognize or be able to ascertain using no more than routine experimentation many equivalents to the specific embodiments described herein.

The articles "a" and "an" are used herein to refer to one or to more than one (i.e., to at least one) of the grammatical object of the article. By way of example, "an element" means one element or more than one element.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, certain embodiments of the invention or aspects of the invention consist, or consist essentially of, such elements and/or features. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

As used herein, the term "about" generally may refer to any value within a range of 10% of the recited value. In some instance, however, "about" may encompasses a range of 20% of the recited value.

In addition, it is to be understood that any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the methods of the invention can be excluded from any one or more claims, for any reason, whether or not related to the existence of prior art. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Each of the foregoing patents, patent applications and references is hereby incorporated by reference, particularly for the teaching referenced herein.

REFERENCES

[1] Petersen, M. & Wengel, J. LNA: a versatile tool for therapeutics and genomics. Trends Biotechnol. 21, 74-81, (2003).
[2] Krueger, A. T. & Kool, E. T. Redesigning the Architecture of the Base Pair: Toward Biochemical and Biological Function of New Genetic Sets. Chem. Biol. 16, 242-248 (2009).
[3] Lizardi, P. M. et al. Mutation detection and single-molecule counting using isothermal rolling-circle amplification. Nat. Genet. 19, 225-232 (1998).
[4] Saiki, R. K., Gelfand, D. H., Stoffel, S., Scharf, S. J., Higuchi, R., Horn, G. T., Mullis, K. B. & Erlich, H. A. Primer-directed enzymatic amplification of DNA with a thermostable DNA polymerase. Science 239, 487-491 (1988).
[5] Zhang, D. Y., Chen, X. & Yin, P. Optimizing Nucleic Acid Hybridization Specificity. submitted (2011).

The invention claimed is:

1. A single-stranded primer that partially self-hybridizes to form
   (1) a double-stranded target-non-specific region,
   (2) a double-stranded target-specific region,
   (3) a single-stranded target-specific region, and
   (4) a hairpin loop region,
   wherein the double-stranded target-non-specific region has a concentration-adjusted standard free energy that is within 10% of the concentration-adjusted standard free energy for the single-stranded target-specific region bound to a perfectly complementary region of a target nucleic acid, wherein the sequence of region (1) is not perfectly complementary to and does not bind to the target nucleic acid, and wherein the sequences of regions (2) and (3) are complementary to and bind to the target nucleic acid.

2. The single-stranded primer of claim 1, wherein the double-stranded target non-specific region is about 4-21 nucleotide base pairs in length.

3. The single-stranded primer of claim 1, wherein the single-stranded target-specific region is about 4-20 nucleotides in length.

4. The single-stranded primer of claim 1, wherein the hairpin loop region is 4-30 nucleotides in length.

5. The single-stranded primer of claim 1, wherein the single-stranded primer is comprised of deoxyribonucleic acid (DNA).

6. The single-stranded primer of claim 1, wherein the single-stranded primer is comprised of ribonucleic acid (RNA).

7. A method of performing a multiplexed nucleic acid amplification reaction comprising amplifying multiple unique nucleic acid molecules using the primer of claim 1.

8. A method comprising
   contacting the single-stranded primer of claim 1 to a sample, and detecting hybridization of the primer to a target in the sample.

9. A method comprising performing a nucleic acid synthesis reaction in the presence of a nucleic acid target, a polymerase, and at least one single-stranded primer of claim 1.

10. A kit comprising
    at least one single-stranded primer of claim 1, and
    at least one nucleic acid synthesis reagent.

11. A single-stranded deoxyribonucleic acid primer that partially self-hybridizes to form
    (1) a double-stranded target-non-specific region having a length of 4-21 nucleotides, (2) a double-stranded target-specific region,
(3) a single-stranded target-specific region having a length of 4-20 nucleotides, and
(4) a hairpin loop region having a length of 4-30 nucleotides,
wherein the double-stranded target-non-specific region has a concentration-adjusted standard free energy that is within 10% of the concentration-adjusted standard free energy for the single-stranded target-specific region bound to a perfectly complementary region of a target nucleic acid, wherein the sequence of region (1) is not perfectly complementary to and does not bind to the target nucleic acid, and wherein the sequences of regions (2) and (3) are complementary to and bind to the target nucleic acid.

12. The single-stranded primer of claim 11, wherein the single-stranded primer is comprised of deoxyribonucleic acid (DNA).

13. The single-stranded primer of claim 11, wherein the single-stranded primer is comprised of ribonucleic acid (RNA).

14. A method of performing a multiplexed nucleic acid amplification reaction comprising amplifying multiple unique nucleic acid molecules using the primer of claim 11.

15. A system comprising a nucleic acid target, a polymerase, and a single-stranded primer that partially self-hybridizes to form (1) a double-stranded target-non-specific region,
(2) a double-stranded target-specific region,
(3) a single-stranded target-specific region, and
(4) a hairpin loop region, wherein the double-stranded target-non-specific region has a concentration-adjusted standard free energy that is within 10% of the concentration-adjusted standard free energy for the single-stranded target-specific region bound to a perfectly complementary region of a target nucleic acid, wherein the sequence of region (1) is not perfectly complementary to and does not bind to the target nucleic acid, and wherein the sequences of regions (2) and (3) are complementary to and bind to the target nucleic acid.

16. The system of claim 15, wherein the double-stranded target non-specific region is about 4-21 nucleotide base pairs in length.

17. The system of claim 15, wherein the single-stranded target-specific region is about 4-20 nucleotides in length.

18. The system of claim 15, wherein the hairpin loop region is 4-30nucleotides in length.

19. The system of claim 15, wherein the single-stranded primer is comprised of deoxyribonucleic acid (DNA).

20. The system of claim 15, wherein the single-stranded primer is comprised of ribonucleic acid (RNA).

21. The system of claim 15 further comprising a nucleic acid target.

* * * * *